United States Patent
Popejoy et al.

(10) Patent No.: US 11,464,504 B2
(45) Date of Patent: Oct. 11, 2022

(54) LATERAL ACCESS BRIDGES, SHIMS AND LIGHTING INCLUDING ROD LIGHTING

(71) Applicant: Stryker European Operations Holdings LLC, Kalamazoo, MI (US)

(72) Inventors: Spencer Popejoy, Ringwood, NJ (US); Charles L. Bush, Jr., Wayne, NJ (US); Steven F. Krause, Oakland, NJ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 143 days.

(21) Appl. No.: 16/639,385

(22) PCT Filed: Aug. 17, 2018

(86) PCT No.: PCT/US2018/000344
§ 371 (c)(1),
(2) Date: Feb. 14, 2020

(87) PCT Pub. No.: WO2019/036048
PCT Pub. Date: Feb. 21, 2019

(65) Prior Publication Data
US 2020/0253592 A1 Aug. 13, 2020

Related U.S. Application Data

(60) Provisional application No. 62/650,579, filed on Mar. 30, 2018, provisional application No. 62/546,796, filed on Aug. 17, 2017.

(51) Int. Cl.
*A61B 17/02* (2006.01)
*A61B 90/30* (2016.01)
*A61B 17/00* (2006.01)

(52) U.S. Cl.
CPC .............. *A61B 17/02* (2013.01); *A61B 90/30* (2016.02); *A61B 2017/00473* (2013.01);
(Continued)

(58) Field of Classification Search
CPC ..... A61B 17/02; A61B 17/0206; A61B 90/30; A61B 2090/309; A61B 2017/00473;
(Continued)

(56) References Cited

U.S. PATENT DOCUMENTS

| 3,749,088 A | 7/1973 | Kohlmann |
| 3,807,393 A | 4/1974 | McDonald |

(Continued)

FOREIGN PATENT DOCUMENTS

| WO | 2004077922 A2 | 9/2004 |
| WO | 2018039228 A1 | 3/2018 |

(Continued)

OTHER PUBLICATIONS

ER-SPEC, Single-Use Vaginal Speculum with Integrated LED Light Source, OBP Medical Inc, Mar. 15, 2017.

(Continued)

*Primary Examiner* — Jessica Weiss
(74) *Attorney, Agent, or Firm* — Lerner, David, Littenberg, Krumholz & Mentlik, LLP

(57) ABSTRACT

In one embodiment, a system (20, 30) includes a retractor (100, 100A, 1113) with a plurality of rods (120, 120A-1-124A-1, 180, 220, 320, 420, 1111A-E) that are cylindrical over part of their length, a light source (230, 330), and a fiber optic cable (229, 329), where at least one rod includes a body with an opening (122, 182, 222, 322) therein. The opening extends from an upper surface (122A, 181B, 222A, 322A) of the rod, through an interior of the rod, and then to a side surface (122B, 182D, 222B, 322B) of the rod located between ends of the rod. The opening is sized so that at least a single monofilament fiber optic cable is disposable therethrough. The system is adapted so that any number of rods (Continued)

may include a fiber optic cable disposed therein and so that the cable may be easily removed or inserted from the rod during use of the retractor.

20 Claims, 34 Drawing Sheets

(52) U.S. Cl.
CPC ............ *A61B 2017/00734* (2013.01); *A61B 2017/00862* (2013.01); *A61B 2017/00907* (2013.01); *A61B 2017/0256* (2013.01); *A61B 2090/309* (2016.02)

(58) Field of Classification Search
CPC .......... A61B 2017/00734; A61B 2017/00862; A61B 2017/00907; A61B 2017/0256; A61B 1/32
USPC .................................................. 600/201–249
See application file for complete search history.

(56) References Cited

U.S. PATENT DOCUMENTS

| | | | |
|---|---|---|---|
| 3,965,890 A | 6/1976 | Gauthier | |
| 4,010,741 A | 3/1977 | Gauthier | |
| 4,616,635 A | 10/1986 | Caspar et al. | |
| 5,928,139 A | 7/1999 | Koros et al. | |
| 6,466,817 B1 | 10/2002 | Kaula et al. | |
| 6,564,078 B1 | 5/2003 | Marino et al. | |
| 6,760,616 B2 | 7/2004 | Hoey et al. | |
| 6,846,287 B2 | 1/2005 | Bonadio et al. | |
| 7,150,714 B2 | 12/2006 | Myles | |
| 7,207,949 B2 | 4/2007 | Miles et al. | |
| 7,223,233 B2 | 5/2007 | Branch et al. | |
| 7,491,168 B2 | 2/2009 | Raymond et al. | |
| 7,582,058 B1 | 9/2009 | Miles et al. | |
| 7,686,492 B2 * | 3/2010 | Vayser .................... | A61C 1/088 362/572 |
| 7,691,057 B2 | 4/2010 | Miles et al. | |
| 7,758,501 B2 | 7/2010 | Frasier et al. | |
| 7,785,253 B1 | 8/2010 | Arambula et al. | |
| 7,874,982 B2 | 1/2011 | Selover et al. | |
| 7,891,801 B2 | 2/2011 | Nakajima | |
| 7,892,173 B2 | 2/2011 | Miles et al. | |
| 7,905,840 B2 | 3/2011 | Pimenta et al. | |
| 7,918,891 B1 | 4/2011 | Curran et al. | |
| 7,920,922 B2 | 4/2011 | Gharib et al. | |
| 7,976,463 B2 | 7/2011 | Dewey et al. | |
| 7,981,029 B2 | 7/2011 | Branch et al. | |
| 8,062,217 B2 | 11/2011 | Boucher et al. | |
| 8,105,236 B2 | 1/2012 | Malandain et al. | |
| 8,137,284 B2 | 3/2012 | Miles et al. | |
| 8,157,728 B2 | 4/2012 | Danna et al. | |
| 8,192,356 B2 | 6/2012 | Miles et al. | |
| 8,206,293 B2 | 6/2012 | Regies et al. | |
| 8,317,693 B2 | 11/2012 | Grey et al. | |
| 8,430,813 B2 | 4/2013 | Selover et al. | |
| 8,449,463 B2 | 5/2013 | Nunley et al. | |
| 8,523,768 B2 | 9/2013 | Miles et al. | |
| 8,548,579 B2 | 10/2013 | Gharib et al. | |
| 8,568,317 B1 | 10/2013 | Gharib et al. | |
| 8,608,652 B2 | 12/2013 | Voegele et al. | |
| 8,702,600 B2 | 4/2014 | Perrow | |
| 8,753,270 B2 | 6/2014 | Miles et al. | |
| 8,801,608 B2 | 8/2014 | Hardenbrook | |
| 8,808,172 B2 | 8/2014 | Manzanares | |
| 8,900,137 B1 | 12/2014 | Lovell et al. | |
| 8,915,846 B2 | 12/2014 | Miles et al. | |
| 8,942,801 B2 | 1/2015 | Miles et al. | |
| 8,956,283 B2 | 2/2015 | Miles et al. | |
| 8,968,363 B2 | 3/2015 | Weiman et al. | |
| 8,992,558 B2 | 3/2015 | Stone et al. | |
| 9,044,280 B1 | 6/2015 | Arambula et al. | |
| 9,050,146 B2 | 6/2015 | Woolley et al. | |
| 9,066,701 B1 | 6/2015 | Finley et al. | |
| 9,125,587 B2 | 9/2015 | Hawkins et al. | |
| 9,138,217 B2 | 9/2015 | Smith et al. | |
| 9,204,871 B2 | 12/2015 | Miles et al. | |
| 9,259,144 B2 | 2/2016 | Smith et al. | |
| 9,265,493 B2 | 2/2016 | Miles et al. | |
| 9,271,709 B2 | 3/2016 | Grey et al. | |
| 9,351,718 B1 | 5/2016 | Arambula et al. | |
| 9,380,932 B1 * | 7/2016 | Lynn .................... | A61B 1/0684 |
| 9,480,855 B2 | 11/2016 | DiMauro et al. | |
| 9,486,133 B2 | 11/2016 | Coleman et al. | |
| 9,572,560 B2 | 2/2017 | Mast et al. | |
| 9,610,071 B2 | 4/2017 | Miles et al. | |
| 9,610,130 B2 | 4/2017 | Vayser et al. | |
| 9,615,818 B2 | 4/2017 | Baudouin et al. | |
| 9,655,505 B1 * | 5/2017 | Gharib ............... | A61B 17/0293 |
| 9,750,490 B2 | 9/2017 | Miles et al. | |
| 9,795,370 B2 | 10/2017 | O'Connell et al. | |
| 9,795,371 B2 | 10/2017 | Miles et al. | |
| 9,820,729 B2 | 11/2017 | Miles et al. | |
| 10,172,515 B2 | 1/2019 | Coleman et al. | |
| 2005/0277812 A1 | 12/2005 | Myles | |
| 2006/0224045 A1 | 10/2006 | Whipple et al. | |
| 2006/0256575 A1 * | 11/2006 | Vayser .................... | A61B 1/303 362/573 |
| 2007/0060795 A1 * | 3/2007 | Vayser ............... | A61B 17/0206 600/245 |
| 2008/0319432 A1 | 12/2008 | Ely et al. | |
| 2009/0097236 A1 * | 4/2009 | Miller ...................... | A61B 1/32 362/119 |
| 2009/0221879 A1 | 9/2009 | Gorek | |
| 2012/0041272 A1 | 2/2012 | Dietze, Jr. et al. | |
| 2014/0323811 A1 * | 10/2014 | DeSantis ................... | A61B 1/07 600/213 |
| 2015/0051448 A1 | 2/2015 | Hunt et al. | |
| 2015/0088020 A1 | 3/2015 | Dreisbach et al. | |
| 2015/0088030 A1 | 3/2015 | Taylor | |
| 2015/0230749 A1 | 8/2015 | Gharib et al. | |
| 2015/0230787 A1 | 8/2015 | Friedrich et al. | |
| 2016/0015467 A1 * | 1/2016 | Vayser ..................... | G09B 5/06 600/245 |
| 2016/0038012 A1 * | 2/2016 | McMahon ........... | A61B 1/0669 600/210 |
| 2016/0051242 A1 | 2/2016 | Predick et al. | |
| 2016/0157953 A1 * | 6/2016 | Grey ...................... | A61B 1/267 600/249 |
| 2016/0192922 A1 | 7/2016 | Friedrich et al. | |
| 2016/0361052 A1 | 12/2016 | Reimels | |
| 2017/0215856 A1 | 8/2017 | Martinelli et al. | |
| 2017/0312045 A1 * | 11/2017 | McGuire ................ | A61B 90/35 |
| 2018/0336474 A1 * | 11/2018 | Vayser ................. | G02B 6/0001 600/245 |
| 2019/0053826 A1 * | 2/2019 | Bush, Jr ............. | A61B 17/0206 |

FOREIGN PATENT DOCUMENTS

| | | |
|---|---|---|
| WO | 2019036036 A1 | 2/2019 |
| WO | 2019036039 A2 | 2/2019 |

OTHER PUBLICATIONS

International Search Report and Written Opinion for PCT/US2018/000344, dated Jan. 3, 2019.
International Search Report and Written Opinion for PCT/US2018/000344, dated Mar. 4, 2019.
KleenSpec® 790 Series, Cordless Illumination System for the 590 Series Vaginal Speculum, Welch Allyn, Advancing Frontline Care., Instructions Manual pp. 1-32, published 2012.
ONETRAC, Single-Use Cordless Retractor with Integrated LED Light Source, OBP Medical Inc, Mar. 15, 2017.
SURE-SCOPE, Single-Use Laryngoscope with Integrated LED Light Source, OBP Medical Inc, Mar. 15, 2017.

* cited by examiner

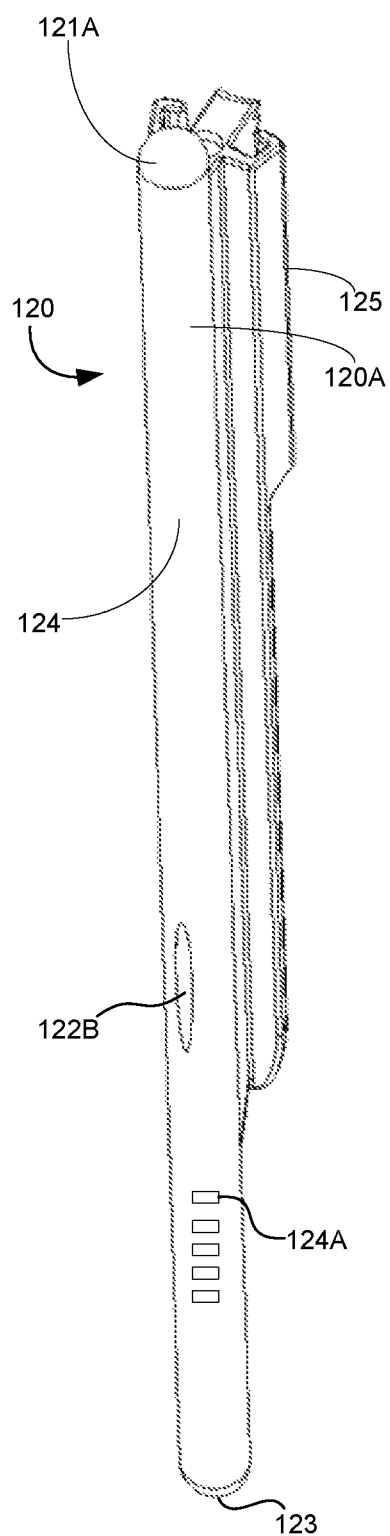
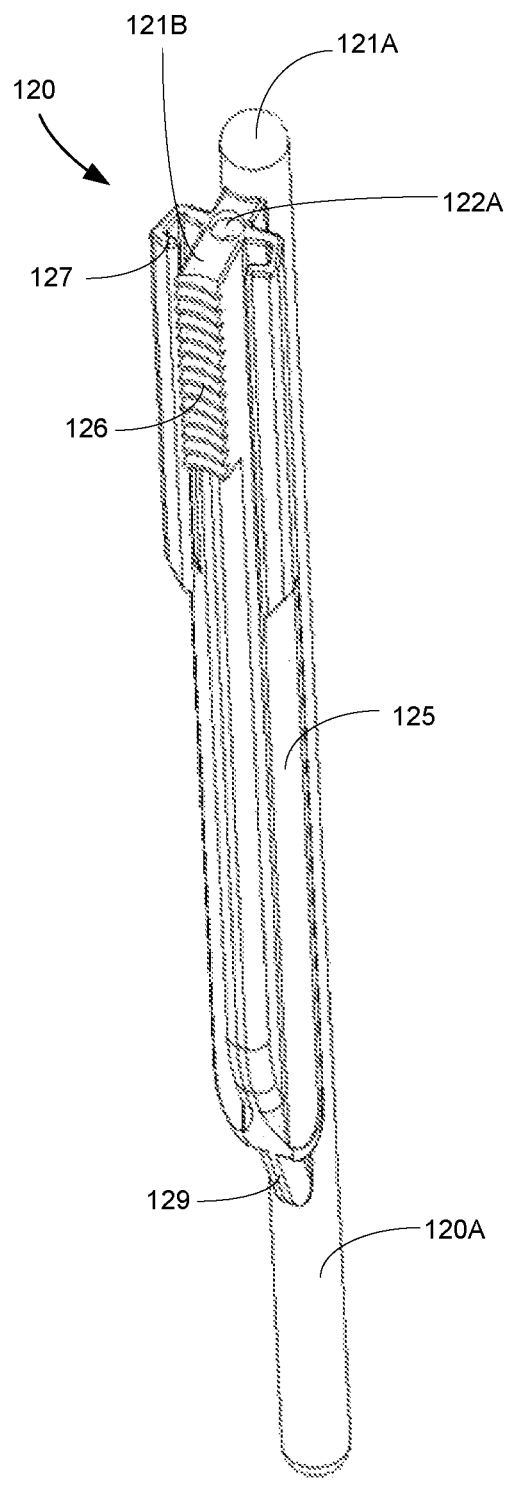
FIG. 3
FIG. 4

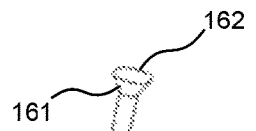
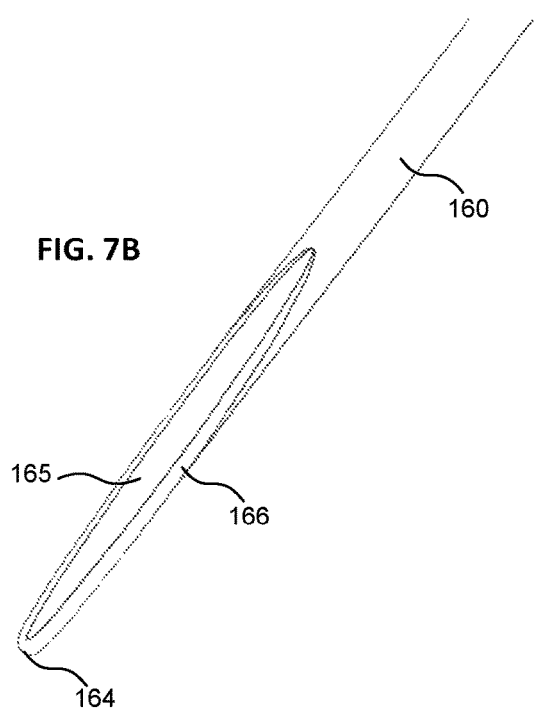
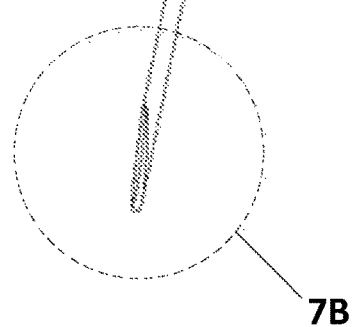
FIG. 7A
FIG. 7B

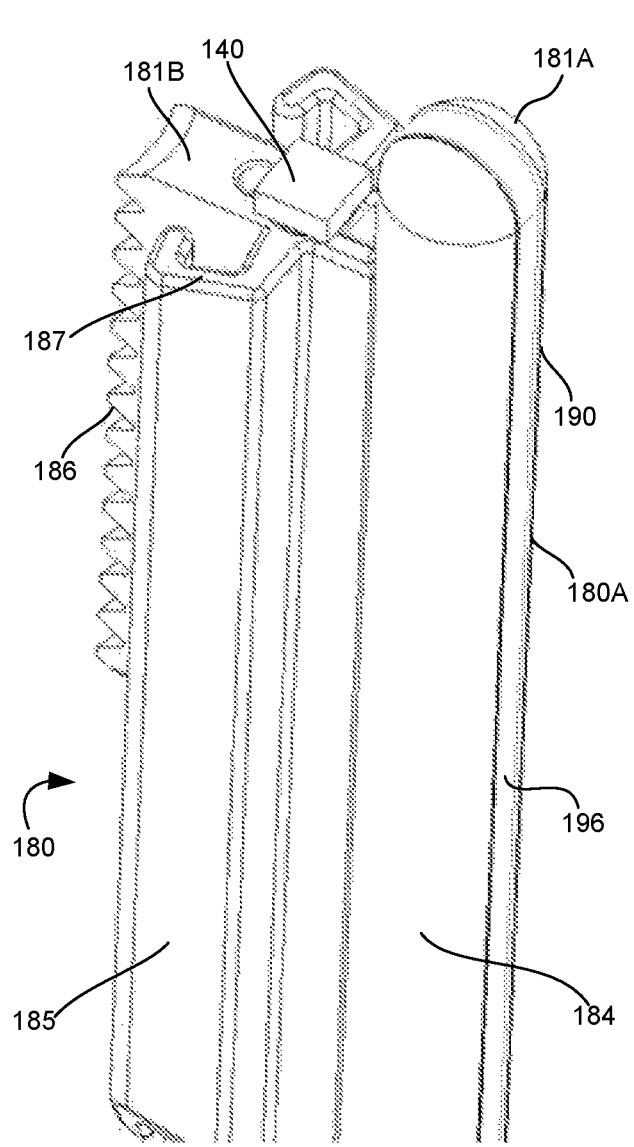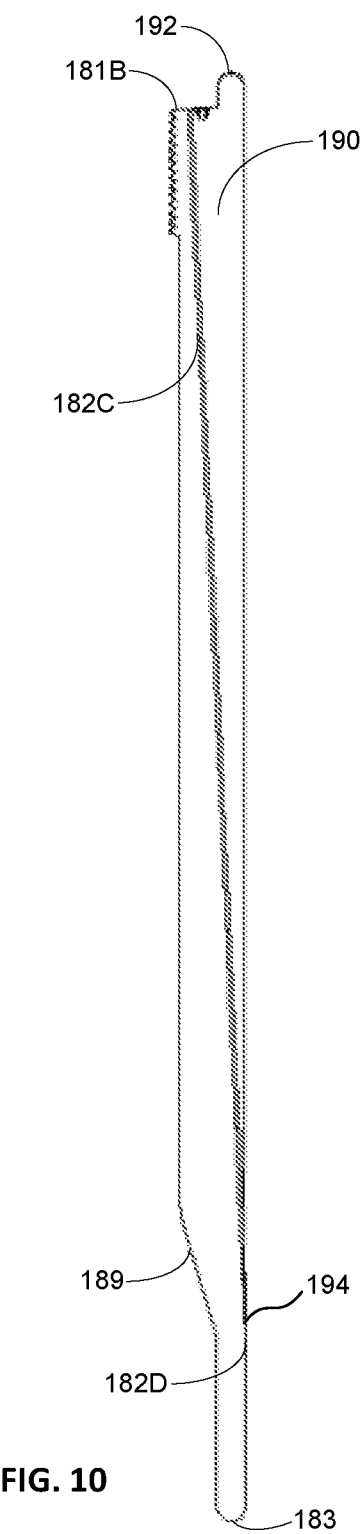
FIG. 9
FIG. 10

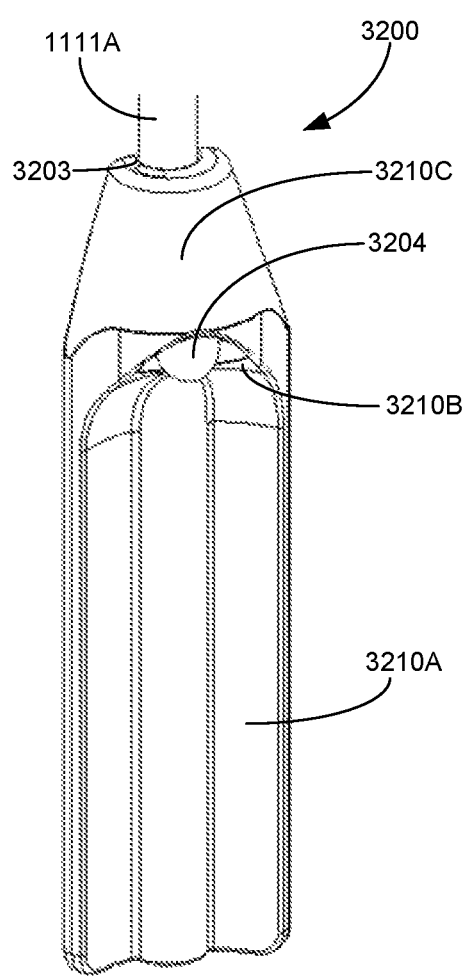
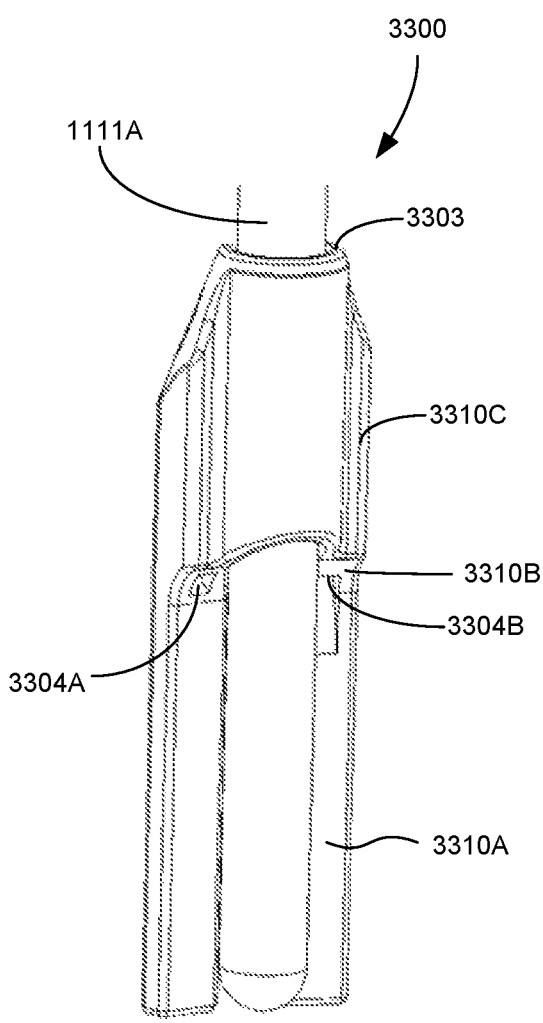
FIG. 56
FIG. 57

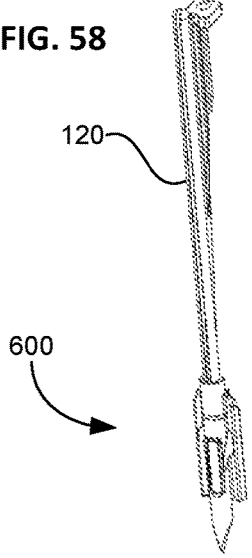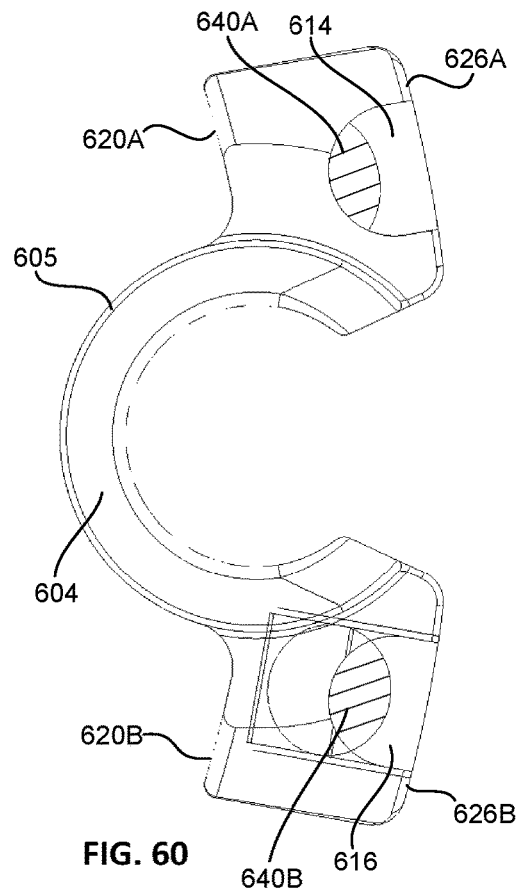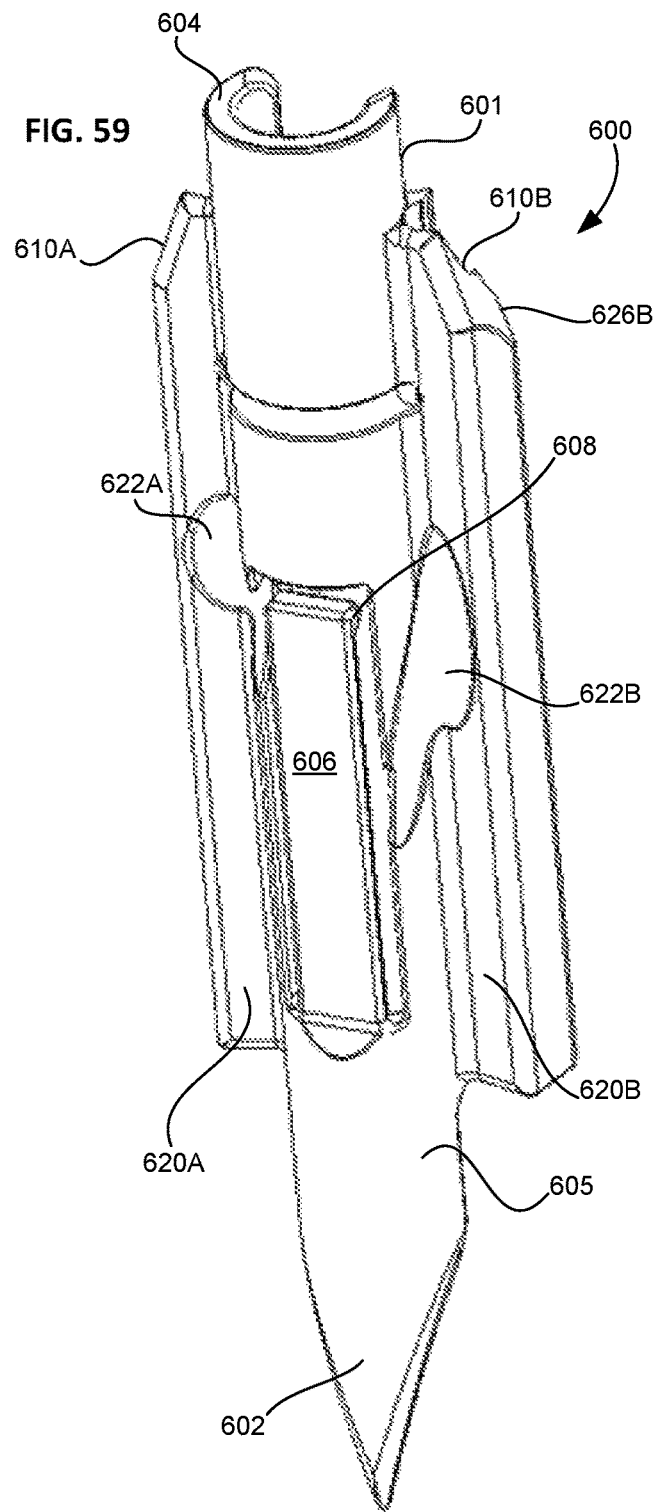
FIG. 58
FIG. 59
FIG. 60

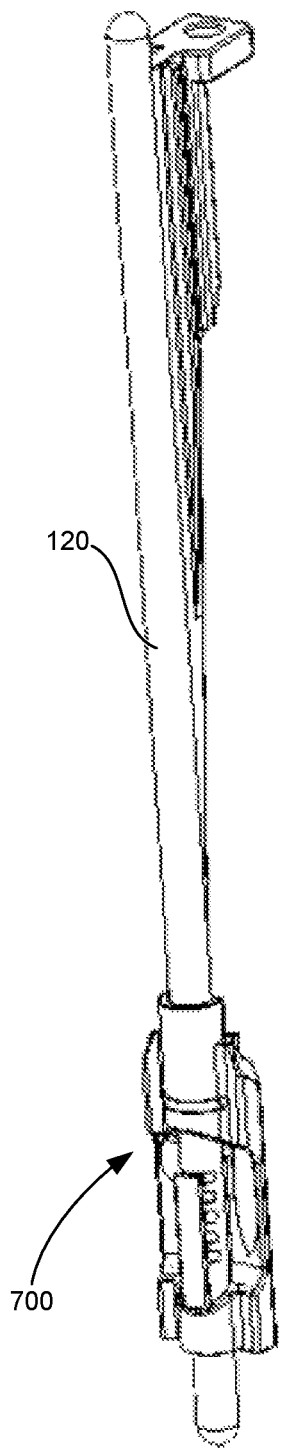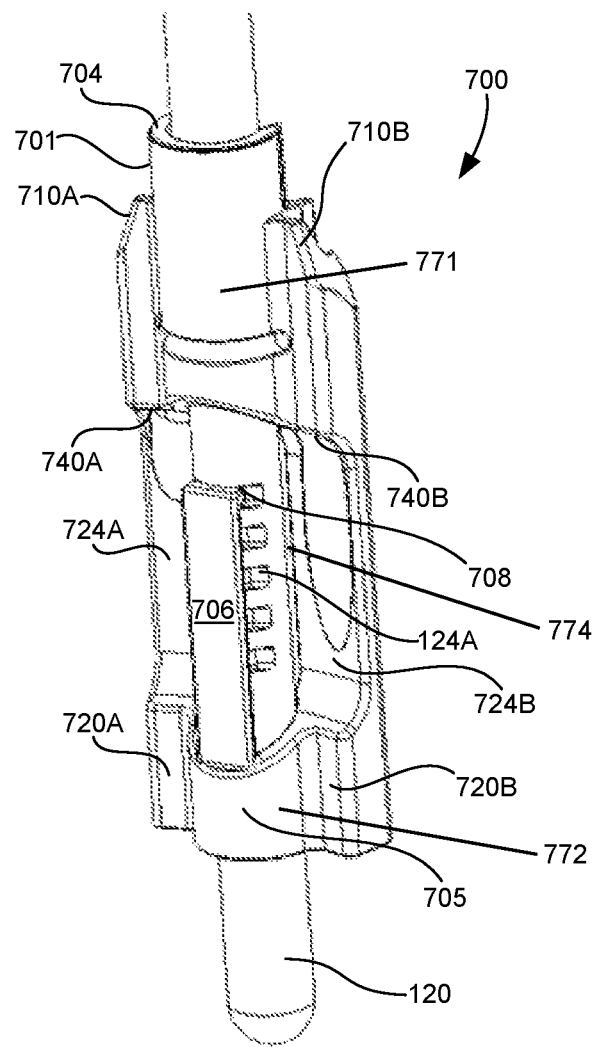
FIG. 61
FIG. 62

US 11,464,504 B2

LATERAL ACCESS BRIDGES, SHIMS AND LIGHTING INCLUDING ROD LIGHTING

CROSS-REFERENCE TO RELATED APPLICATIONS

The present application is a national phase entry under 35 U.S.C. § 371 of International Application No. PCT/US2018/000344 filed on Aug. 17, 2018, which claims the benefit of U.S. Provisional Patent Application No. 62/546,796, filed on Aug. 17, 2017, and U.S. Provisional Patent Application No. 62/650,579, filed on Mar. 30, 2018, the disclosures of which are hereby incorporated by reference herein in their entirety. Additionally, the disclosure of commonly owned WO2018/039228, filed Aug. 22, 2017 (the '228 Publication) and the disclosures of commonly owned U.S. Provisional Patent Application Nos. 62/546,841 ("the '841 Application"), 62/546,780 ("the '780 Application), and 62/546,847 ("the '847 Application") are also hereby incorporated by reference herein in their entirety.

BACKGROUND OF THE INVENTION

Performing spinal surgery on a patient in a minimally invasive manner has reduced the extent of interference with organs of the patient and thus has reduced risks normally associated with surgery. For instance, lateral approaches have been found to be advantageous in that a portal to access a surgical site may be larger than with other approaches, thus allowing for a larger implant to be used, which experience over time has shown tends to improve the overall outcome of a procedure. However, performing an operation through a small surgical portal during such procedures still presents challenges for surgeons. For example, such surgical portals within the patient should only remain open for a short period of time, otherwise, the well being of the patient may be compromised. This can be problematic given that additional time and effort is often necessary to introduce light into the typically dark portal. Other challenges include that light reaching the portal is often inefficient due to the distance it must travel.

At present, fiber optic lighting is a common technology used to provide lighting in minimally invasive spinal procedures by using a high powered light-box which is positioned away from the operating table and feeds the fiber optic terminating light source through long fiber optic cables and multiple connections. Often these arrangements require attachment of cables to a table or other surface near a retractor or, if desired to place onto a surface of the retractor itself, such cables consume valuable space within the surgical portal and make it difficult to avoid contact with such cables during a procedure. One example of a fiber optic lighting application involves attaching a fiber optic lighting cable to a frame of a retractor that holds the surgical portal open, and directing a light emitting end of the cable into the portal. In another approach to lighting a surgical portal, a surgeon may wear a headlamp with a light emitting device attached to direct light into the portal. The latter approach may be undesirable due to its encumbering the wearer and due to even more lost efficiency from other fiber optic approaches, as light must travel from a head of the wearer to a surgical portal. Still further examples involve placement of other light emanating tools into the surgical portal after it is opened with a retraction device.

Additionally, the extra procedural steps required with known approaches to lighting during spinal surgery add clutter into the operating theater, either inside the surgical portal, in the area surrounding it, or both, and can use up a significant portion of the window of time under which the surgeon may safely operate.

Other problems with contemporary techniques of minimally invasive surgery include tissue creep when a portal is opened. In particular, blades of existing retractors often are positioned with large gaps in between when in an expanded state. In such circumstances, tissue may creep in between the blades and into an open space created by retraction of the blades, thus reducing a size of the working volume. Moreover, even when additional stabilizing structures such as rings are used to preserve the opening through the tissue, such structures often consume a significant amount of physical space within the surgical portal, making the working volume for the surgeon smaller than it would be otherwise.

Accordingly, there is a need to improve techniques for lighting a surgical portal in a body of a patient to minimize obstructions due to lighting and to simplify and reduce the time necessary to successfully perform surgeries. Solutions that improve lighting while also improving the stability of a surgical portal and maintenance of access to the surgical portal, such as through the reduction of tissue creep, are also desirable.

BRIEF SUMMARY OF THE INVENTION

The various aspects of the present disclosure provide improvements to address the above deficiencies related to minimally invasive surgery. These solutions include, but are not limited to, improved lighting in a working surgical portal used to perform surgery and improved maintenance of a size and shape of such surgical portal.

In one aspect, the present disclosure relates to a system including rod structures adapted for attachment to a tissue retractor and associated elements to provide lighting that emanates from the rods. In one embodiment, the system includes a total of five rods, two or three of which include a hole therethrough that extends from a top surface of the rod to a side surface. Inserts in the form of light pipes are also included and are inserted into the hole of rods structured to house such light pipes. Each rod with a light pipe inserted therein includes a light emitting diode ("LED") attached thereon so that light generated by the LED is transmitted through the light pipe and out of the side of the rod. The system further comprises a battery along with connections to provide power to each of the LEDs. In a variant of this embodiment, the rods adapted for lighting have an internal slot instead of a hole, the slot sized for insertion of a light bar therein. This variant is otherwise the same as that described above.

In another embodiment, a system includes a total of five rods where two or three are lighting rods configured for attachment to a retractor that include physical pockets recessed in a side surface along their length. For each of these rods, an LED is attached within a respective pocket. Here, a battery is connected to each LED and thus supplies power so that the LEDs may light up during use, such as when the rods are retracted to create a surgical portal, i.e., working portal, during surgery. Alternatively, wall power or another AC source may be used in conjunction with a transformer to convert incoming current to DC, thereby powering the LEDs.

These and other embodiments of the present disclosure provide higher efficiency lighting than approaches where a light source is external to a surgical portal. The inclusion of LED lighting generates less heat than other forms of light. Further, polymer-based fiber optic cables for delivery of light to the surgical portal are also advantageous in that such structure transmits a minimal amount of heat compared with other carriers of light. And, because power may be supplied by a battery, the power source has a smaller footprint outside of the working portal than other power sources, such as a light-box. LEDs for generation of light also require minimal space and battery power removes the risk of electrical shock with a wall outlet. Similarly, shorter, smaller wires limit if not altogether remove tripping hazards between an operating table and equipment tables. In addition to the above, when lighting is integrated into working portal elements, e.g., rods, less space within the portal is used compared to current approaches.

In another aspect, the present disclosure relates to a rod for placement in a surgical portal, the rod including a body, an opening in the body, an insert and a light source. In one embodiment, the insert is made of a light transmitting material with dimensions corresponding to those of the opening and is disposed in the opening and the light source is positioned relative to the body so that when light emanates from the light source, such light travels through the insert and out of the body.

In some embodiments, the opening in the body extends between a top surface of the body and a side surface of the body. In other embodiments, the opening in the body is a hole and the insert is a light pipe having a rounded shape. In some variants of those embodiments, the light pipe includes a stepped surface at one end, the stepped surface having a radius consistent with a radius of a cylindrical surface of the body. In other variants, the hole is linear with a first axis therethrough, the first axis being less than 30 degrees from a longitudinal axis of the body.

In some embodiments, the opening in the body is a slot and the insert is a light bar having a tapered dimension along its length with a width corresponding to a width of the slot. In a variant, the slot extends from the top surface of the body to a side surface of the body in a continuous manner, a portion on the side surface extending over a majority of a length of the rod. In still other embodiments, the light source is a light emitting diode. In others, the light transmitting material is clear acrylic, clear polycarbonate, clear PMMA or clear glass fiber.

In another aspect, the present disclosure relates to a system for lighting a working portal during surgery. In one embodiment, the system includes a retractor, first, second and third rods attached to the retractor, a power source, and a connection between the power source and the light source. One or more of the first, second and third rods is a lighting rod and includes an insert disposed within a body of the rod, the insert being made of a light transmitting material and a light source. The light source is positioned relative to the insert so that light is transmitted through the insert.

In some embodiments, the retractor includes a total of five rods and two or three of the five rods are lighting rods. In other embodiments, a total number of lighting rods is less than a total number of rods including the lighting rods. In still further embodiments, the body of the lighting rod also includes an opening defined by an interior surface of the rod and the insert has dimensions corresponding to those of the opening. In a variant, the opening in the rod is a hole and the insert is a light pipe having a rounded shape. In another variant, the opening in the rod is a slot and the insert is a light bar having a tapered dimension along its length with a width corresponding to a width of the slot.

In some embodiments, the connection between the power source and the light source is wireless and the rods with inserts disposed therein include receiving power coils configured to receive power from the power source. In still other embodiments, the light source is a light emitting diode. In others, the light transmitting material is clear acrylic, clear polycarbonate, clear PMMA or clear glass fiber.

In another aspect, the present disclosure relates to a system for lighting a working portal during surgery and includes a retractor, first, second and third rods attached to the retractor, a power source and a connection between the power source and the light source. One or more of the first, second and third rods includes a pocket defined by a recess in a side surface of the rod and a light source disposed in the pocket. The rods of the system are adjustable from a first position to a second position such that the rods are further apart from one another in the second position. In this arrangement, the light source emanates from a surface of the rod.

In some embodiments, the light source is a light emitting diode. In a variant, the light emitting diode faces inward toward a center between the first, second and third rods. In another embodiment, the connection between the power source and the light source is wireless and the rods with a light source disposed thereon include receiving power coils configured to receive power from the power source.

In yet another aspect, the present disclosure relates to a tissue retaining device sized for attachment to a rod of a retractor. The tissue retaining device includes a body and a light emitting diode attached to the body. The body includes a central portion and a wing. The central portion has an inner surface matching a portion of a rod perimeter such that the central portion is configured to clip onto the rod. The central portion also includes a bending clip with a protrusion facing an interior of the central portion that is elastically deformable. The wing is adjacent to the central portion and has a curved surface such that a side in common with an open side of the central portion has a convex surface.

In some embodiments, the body includes a leading end and a trailing end, the leading end terminating in a pointed tip. In other embodiments, the central portion includes a length from a trailing end to a leading end, and the central portion is divided into first and second parts such that the first and second parts are held in position with respect to each other by the wing. In a variant, the bending clip is entirely in between the first and second parts. In another embodiment, the bending clip is defined by a cutout on an outer surface of the central portion.

In another aspect, the present disclosure relates to a kit that includes a package. In one embodiment, the package includes a rod configured for use with a retractor, a light pipe or light bar sized to fit within an opening in the rod, and a light emitting diode. In some embodiments, the kit also includes a battery and wiring configured to transmit power from the battery to the light emitting diode.

In another aspect, the present disclosure relates to a method of lighting a working portal. In one embodiment, the method involves placing a retractor with a plurality of rods attached thereto into a body of a patient; retracting the plurality of rods to create a surgical portal, and activating a power source connected to a first rod of the plurality of rods. The activation of the power source causes power to be transmitted from the power source to a lighting source attached to the first rod through a connection between the power source and the lighting source. Upon activation of the power source, the power received by the lighting source causes lighting source to emit light. In some embodiments, the activation of lighting is automatic based on the retraction of the plurality of rods.

In yet another aspect, the present disclosure relates to a method of assembling a lighting rod. In one embodiment, the method involves inserting a light pipe or a light bar into an opening within a rod configured for use with a retractor and positioning a light emitting diode on the rod so that light emanating from the light emitting diode travels through the light pipe or light bar.

In some embodiments, the method also includes attaching the rod to an arm of a retractor. In other embodiments, the method includes connecting the light emitting diode to a power source. In still further embodiments, the connection is wireless. In other embodiments, the method includes attaching a light emitting diode onto a surface of the rod.

In one aspect, the present disclosure relates to a system for maintenance of a surgical portal in a body of a patient. In one embodiment, the system includes two or more rods adapted for use with a retractor assembly and a bridge structure including a panel and a securement structure engaged with the panel. The securement structure is sized such that at least one rod of the two or more rods is releasably received therein. The system operates so that the bridge structure, when engaged to at least one rod, is disposed on one side of the at least one rod and is movable along a length of the at least one rod. The panel of the bridge structure is of a thickness and is made of a material with a capacity to withstand loads from tissue bearing on a surface of the panel.

In one embodiment, the panel is at least partially curved in a direction orthogonal to a direction of the at least one rod. In another embodiment, the securement structure is a clip in the form of a C-shaped channel. In yet another embodiment, the bridge structure is sized to engage with two of the two or more rods positioned at a distance from one another.

In one embodiment, the securement structure is disposed on a second surface of the panel of the bridge structure, the second surface being concave. In a variant, the bridge structure includes a second securement structure disposed on the first surface of the panel, the first surface being opposite the second surface. In yet another variant, the bridge structure includes a second securement structure disposed on the second surface, the first securement structure and the second securement structure being spaced apart from one another. The first and second securement structures may be disposed at a common location on a length of the panel so that when the at least one rod is engaged with the first support structure and extends over the length of the bridge, the at least one rod does not contact the second support structure.

In one embodiment, the bridge structure includes a skirt panel positioned adjacent to the panel that is rotatable relative to the panel. The skirt panel is capable of rotating about an axis extending between the skirt panel and the panel. In another embodiment, the bridge structure includes a spring element configured so that a width of the panel changes in conjunction with expansion or compression of the spring element. In yet another embodiment, the system includes a light emitting device disposed on the bridge structure. In another embodiment, the panel of the bridge structure includes a second surface opposite the first surface and the first surface exhibits less friction than the second surface.

In another aspect, the present disclosure relates to a bridge structure configured for use with rods associated with a retractor assembly. In one embodiment, the bridge structure includes a panel, a light emitting device and a power cell. The panel includes a body with a cavity therein and a groove on a first surface of the body. The light emitting device is disposed on a second surface of the body and the power cell is disposed in the cavity of the body. The groove on the panel is configured for releasable engagement with a rod of the retractor assembly so that the bridge structure is slidable over the rod when the bridge is engaged to the rod. Additionally, the light emitting device is configured to emit light based on a closed circuit with the power cell.

In some embodiments, the bridge structure includes a feature to control the emission of light. In one embodiment, the bridge structure includes a button on the groove of the first surface. The button is configured to operate as a switch connected to the light emitting device so that upon depression, the light emitting device emits light and upon release, the light emitting device does not emit light. In another embodiment, the bridge structure includes an electrical barrier on the body of the panel. The electrical barrier is configured to cause the light emitting device to emit light upon its removal from the body.

In another embodiment, the second surface of the body is opposite the first surface, the second surface including a tapering portion configured to redirect light from the light emitting device based on a slope of the taper. In a variant, the second surface is made of a transparent material. In yet another embodiment, the bridge structure includes wiring to connect the power cell with the light emitting device. The bridge structure and the wiring are sized so that the wiring is entirely disposed within the body of the panel. In yet another embodiment, a fixation post is attached to the panel. The fixation post is configured for engagement with a soft tissue surface.

In yet another aspect, the present disclosure relates to a method of preparing a patient for implant placement. In one embodiment, the method involves the following steps: advancing three or more rods into an incision in a body of the patient; retracting at least one rod relative to another rod to increase a cross-sectional area of a portal in the body of the patient; engaging a bridge structure to at least one of the three or more rods, a shape of the bridge structure approximately corresponding to a portion of a perimeter of the portal; advancing the bridge structure over the at least one rod so that the bridge structure retracts tissue at a perimeter of the portal, and preventing tissue from entering into the portal. When the bridge structure is fully advanced to a desired position, it may be entirely outside of the cross sectional area of the portal as measured between a point on each of the three or more rods closest to a center of the portal.

In one embodiment, the method also includes a step of rotating a skirt panel of the bridge structure relative to an upper panel of the bridge structure above the skirt panel following advancement of the bridge structure into the portal. The rotation causes the skirt panel to apply pressure to tissue adjacent to the portal. In another embodiment, the method also includes a step of compressing the bridge structure to decrease a width of the bridge structure prior to engaging the bridge structure with two of the three or more rods and then releasing the bridge structure between the two rods so that the bridge structure is engaged to each rod and a pressure is applied from the bridge structure to each rod.

In yet another embodiment, the method also involves securing a probe of an endoscope with the bridge structure prior to engaging the bridge structure with at least one of the three or more rods. In a variant, the probe is secured to a first side of the bridge structure and the at least one of the three or more rods is secured to a second side of the bridge structure. In another embodiment, the engaging step is performed outside of the body of the patient. In yet another embodiment, the bridge structure includes a switch on a surface of a securement structure configured for engagement to the one of the three or more rods. The switch is positioned so that when the bridge structure is engaged to at least one of the three or more rods, a light emitting device connected to the switch and secured to the bridge structure turns on. In one embodiment, the engaging step involves engagement of two securement structures disposed on the bridge structure with two respective rods of the three or more rods. In one embodiment, after engagement but prior to advancement, the bridge structure is rotated about one of the three or more rods with which it is engaged to bring a surface of bridge structure in contact with a second rod adjacent to the rod about which the bridge is rotated.

BRIEF DESCRIPTION OF THE DRAWINGS

A more complete appreciation of the subject matter of the present disclosure and of the various advantages thereof can be realized by reference to the following detailed description in which reference is made to the accompanying drawings in which:

FIG. 3 is a perspective view of a lighting rod without an optic element inserted according to one embodiment of the disclosure.

FIG. 4 is another perspective view of the rod of FIG. 3.

FIG. 7A is a perspective view of the light pipe of FIG. 6.

FIG. 7B is a close up perspective view of the distal end of the light pipe of FIG. 7A.

FIG. 9 is a close up perspective view of a proximal end of a rod with a light bar disposed therein according to one embodiment of the disclosure.

FIG. 10 is a cross sectional view of the rod illustrated in FIG. 9.

FIGS. 35-17 are side, top, and perspective views, respectively depicting the use of the rotating panel bridge of FIGS. 30-31.

FIG. 56 is a perspective view of a lighting bridge according to one embodiment of the disclosure.

FIG. 57 is a perspective view of a lighting bridge according to one embodiment of the disclosure.

FIG. 58 is a perspective view of a shim attached to a rod according to one embodiment of the disclosure.

FIG. 59 is a close up perspective view of the shim of FIG. 58.

FIG. 60 is a top view of the shim of FIG. 58.

FIG. 61 is a perspective view of a bridge attached to a rod according to one embodiment of the disclosure.

FIG. 62 is a close up perspective view of the bridge of FIG. 61.

DETAILED DESCRIPTION

Figure 1:
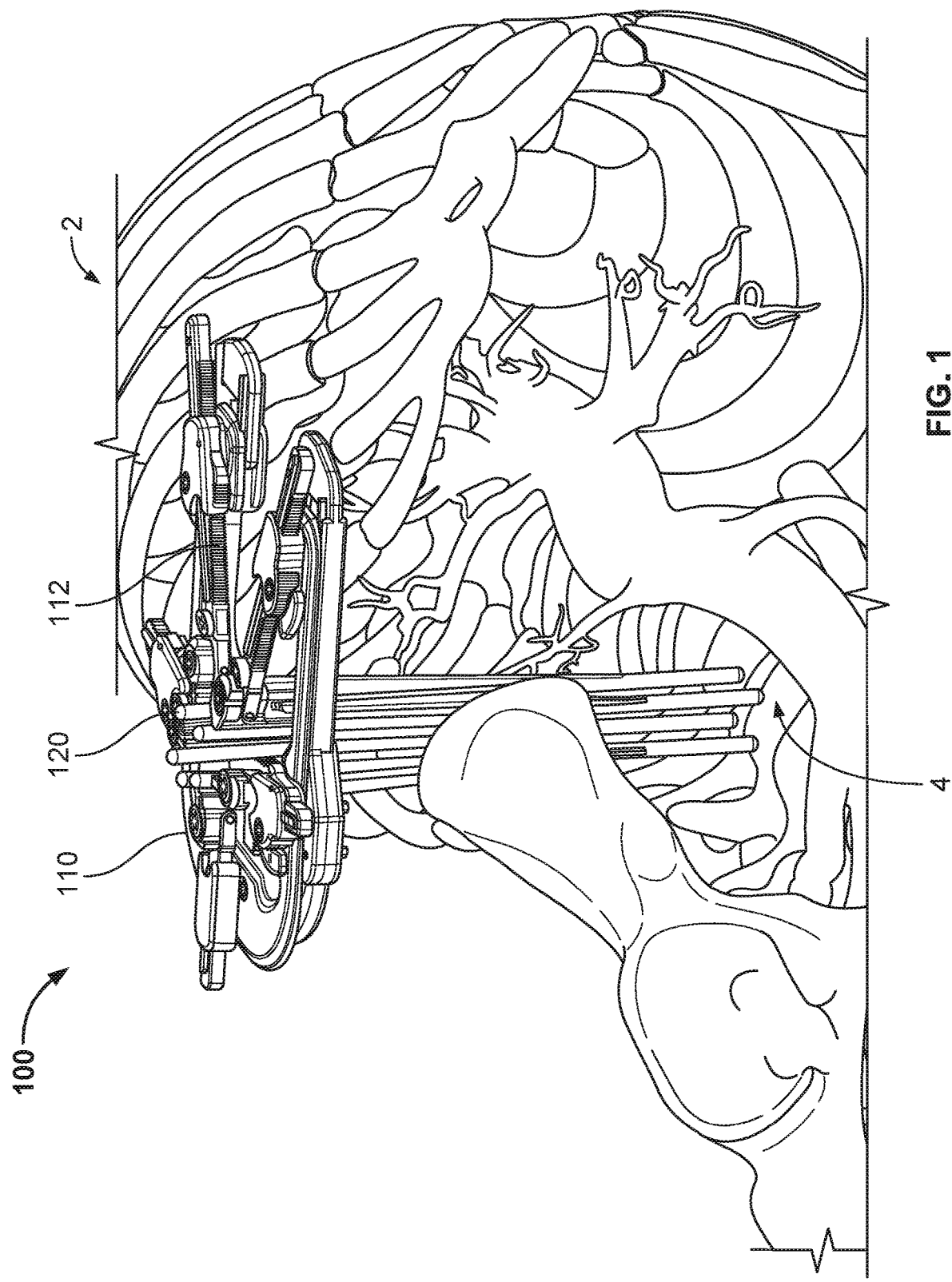
FIG. 1 is a perspective view of a retractor with rods secured thereto, shown schematically positioned within a human body.

The present disclosure describes various apparatuses, devices, systems, kits and methods to improve operating conditions when performing a surgery requiring the creation of a surgical portal in a patient. The technologies described in this application may be employed in many areas of the body and have particular import where minimally invasive surgery is advantageous. Examples of target anatomy include the cervix, the thoracic cavity, the abdomen for anterior laparoscopy, MIS laparotomy or anatomy within the retroperitoneal space, among other procedures, anatomy targeted in cardiac procedures and elements of the nervous system including the brain, cerebrovascular system and the spine. The spine is referenced throughout the application, although it should be appreciated that the concepts described herein are in no way limited to the spine. Approaches to the spine may be lateral, anterior, anterior-lateral, posterior, posterior-lateral or posterior midline. The spine may be accessed for any number of reasons, including treatment of spinal conditions such as disc herniation, implantation of motion preservation devices, total replacement of a disc and implantation of interbody devices, along with many other procedures. Examples of interbody device implantation procedures include lateral lumbar interbody fusion (LLIF), oblique lumbar interbody fusion (OLIF), posterior lumbar interbody fusion (PLIF), anterior lumbar interbody fusion (ALIF), transforaminal lumbar interbody fusion (TLIF), and posterolateral lumbar fusion (PF). Notwithstanding the versatility of the technology described herein, it should be appreciated that the described apparatuses, devices, systems, kits and methods are particularly advantageous when employed in a lateral trans-psoas or anterior to psoas approach to the spine. To provide a clear illustration of the various concepts of this disclosure, the embodiments herein are described in the context of a lateral trans-psoas approach unless otherwise noted.

In the procedures contemplated herein, a retractor is used to create a surgical portal to operate on a patient. Generally, such procedures involve positioning of the retractor, such as the retractor shown in FIG. 1, over the patient, inserting rods of the retractor into the patient and then retracting the rods. Rods with lighting elements, shims or bridges with lighting, among other devices and their methods of application, may be inserted to provide lighting for the surgical portal to aid in visualization during the performance of surgery. To be clear, a surgical portal as described throughout this disclosure is a working volume within a patient undergoing surgery, and in the context of procedures using a retractor with retractable rods, represents a working volume generally interior to and between the retracted rods. By providing lighting on elements already intended to be positioned within the surgical portal, space within the portal is preserved and valuable time is saved through removal of the need to include standalone lighting elements.

Throughout this specification, reference is made to the inclusion of rods adapted for lighting and attached to a retractor, such as retractor 100 shown in FIG. 1. As depicted in FIG. 1, retractor 100 includes a frame 110 with five arms 112, each arm 112 having a rod 120 secured thereto. As background regarding the function of the rods referenced throughout the specification, prior to positioning within a patient 2, rods 120 are initially closed upon one another to minimize a volume occupied by such rods. Once rods are in position in the body, such as is shown in FIG. 1 where the rods are proximal to spine 4, the rods are positioned for the creation of a surgical portal. Through actuation of arms 112, either independently or jointly, rods 120 are retracted to create a surgical portal in the body of the patient. For example, arm 112 is ratcheted so that it moves toward frame 110, simultaneously drawing rod 120 toward frame. Of course, retractor 100 is merely exemplary and the rods as described throughout the disclosure may be adapted or otherwise modified to attach and operate with other retraction structures. For example, the rods may be modified for use with the retractors described in the '228 Publication. Another exemplary retractor system is that shown in FIG. 18, which is similar to that disclosed in the '228 Publication. Retractor system 1100 is supported by a rigid arm 1112 and includes a retractor frame 1113 with a plurality of distractible rods 1111A-E attached thereto. To access a surgical site, a path or portal 20 is created in a body of a patient, spreading apart tissue 14. To create such a portal, rods 1111A-E are inserted into the body in the closed position (not shown). Then, in one approach, the rods are moved to a distracted position (best shown in FIG. 18) using sequential dilation, a process whereby a series of elements are inserted one over the other to increase portal 20 size by displacing tissue 14. One variant of such a process is described in the '847 Application. Of course, other methods may be utilized to distract the rods in accordance with the present disclosure, such as those described in U.S. Pat. No. 8,992,558, the disclosure of which is hereby incorporated by reference herein.

However, it should be understood that the present application has applicability to retractors having more traditional blade structures. Indeed, the adjustable concepts employed in the rods shown and discussed in the present application could be applied to bladed structures as well.

Rod Lighting

With a background regarding the tools used in the creation of a surgical portal in a minimally invasive surgery now established, we turn to the various aspects of the disclosure. One aspect of the present disclosure relates to a system for lighting a surgical portal that includes rod structures such as those shown in FIG. 1 designed to direct light into a surgical portal in a patient to improve lighting in the portal. The systems of this aspect also Include one or more lighting elements along with a power source to supply power to the lighting elements.

Figure 2A:
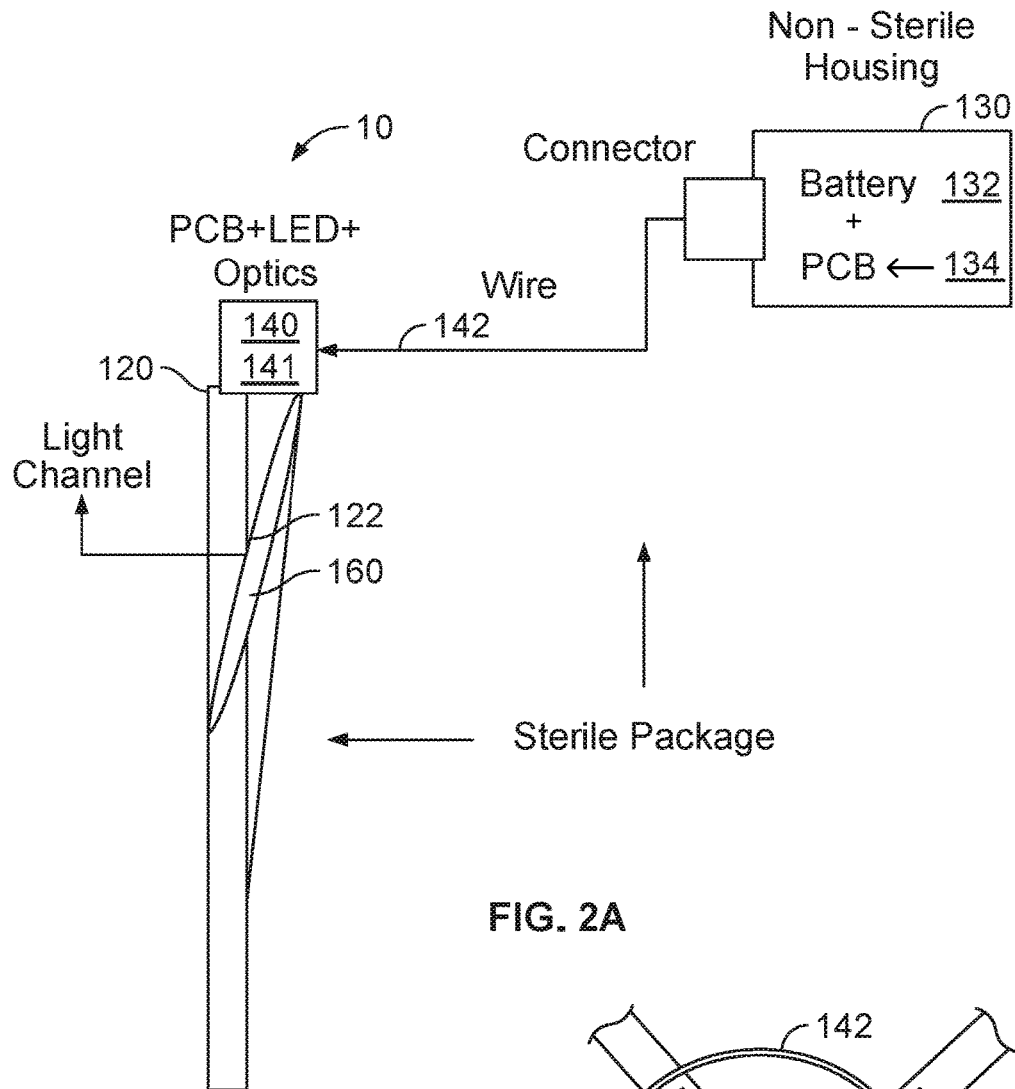
FIG. 2A is a schematic of one embodiment of a system including a rod, a lighting source, and a source of power.
Figure 2B:
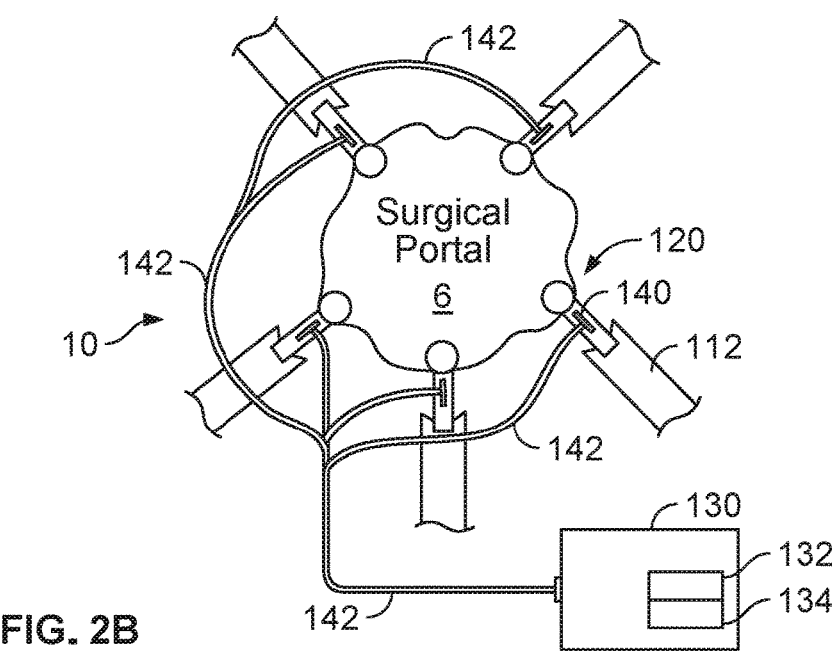
FIG. 2B is a top view of the system of FIG. 2A attached to rods of a retractor.

In one embodiment, a system for providing lighting in a surgical portal is shown in FIG. 2B. This system 10 includes a retractor with arms (shown, for example, in FIG. 1) along with rods 120 attached to respective arms. For purposes of illustration, rods 120 may be attached to a retractor 100 as shown in FIG. 1. As depicted, each rod 120 (five total) is configured as a lighting rod 120 with an optic material 160 inserted therein, both of which are described in greater detail below. A light emitting diode, hereafter referred to as an LED 140, is secured to a surface of each rod 120 (FIG. 2A) and is provided with external power via wire 142, such as a copper wire, from a battery cell 132 within an external unit 130 (FIGS. 2A and 2B). Alternatively, LED 140 may be included as part of system 10 without being physically attached to rod 120. The external unit 130 with battery cell 132 therein is sterilized using a technique such as autoclave steaming or gamma irradiation to preserve a safe environment within the operating theater. As depicted, external unit 130 includes battery 132 and a protection circuit board ("PCB") 134. PCB 134 controls transmission of power from the battery to the LEDs and protects battery 132 from overcharging or overdischarging. Through this arrangement, power may be supplied to the LEDs on the respective rods. Control of power to the LEDs may be toggled with switches or it may toggled automatically based on the satisfaction of particular conditions identified prior to surgery.

Figures 5, 6:
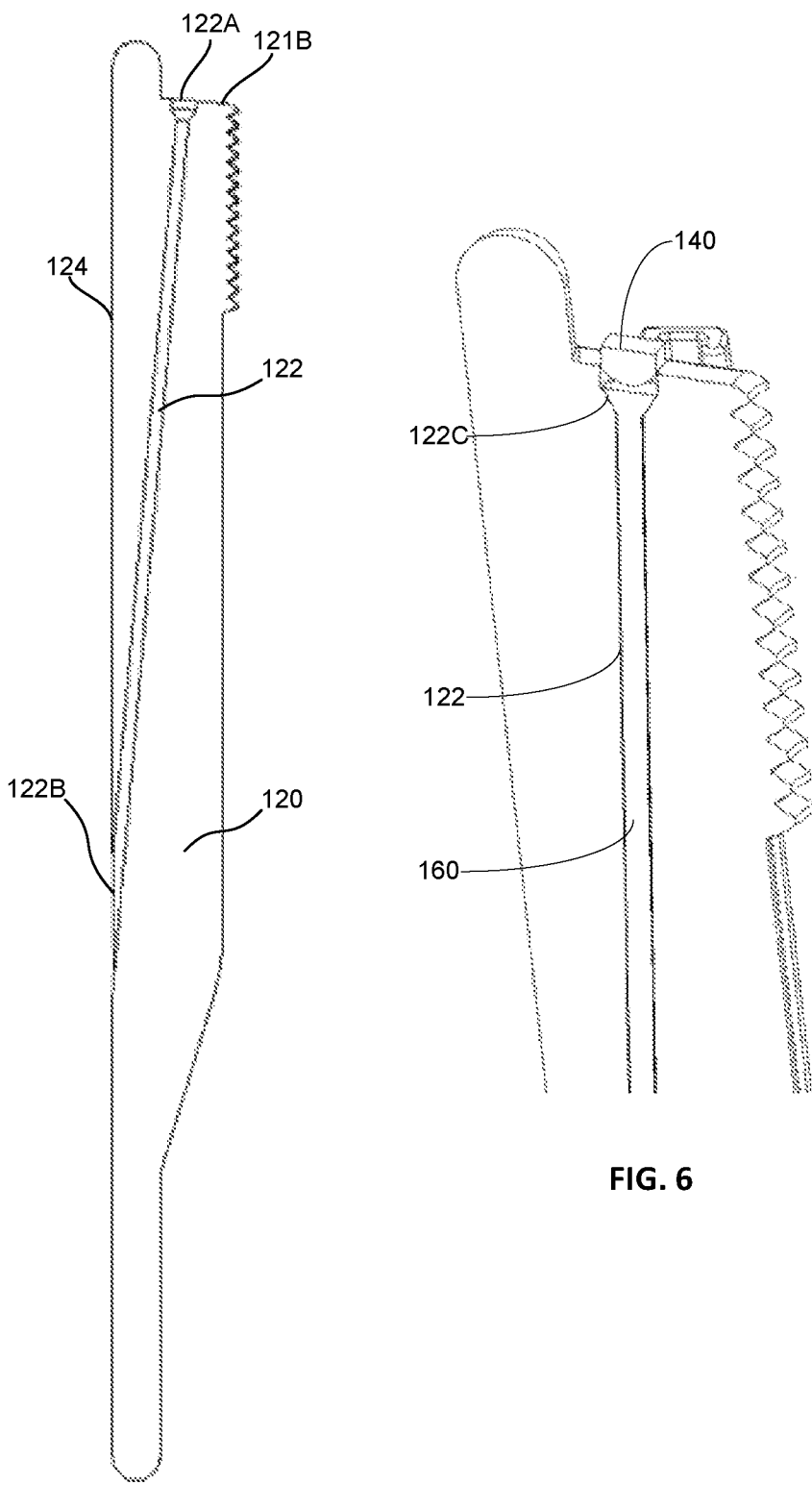
FIG. 5 is a full cross sectional view of the rod of FIG. 3.
FIG. 6 is a close up cross-sectional view of the top portion of the rod of FIG. 3 with a light pipe disposed therein.

Turning now to the specific characteristics of LEDs 140, a position of LEDs 140 in system 10 is on an upper surface of rod 120 as shown in FIGS. 2A-B and in FIGS. 6 and 9. LEDs 140 as depicted in FIG. 2A have a color temperature and brightness desirable for a particular application and are sized to fit on top of rod 120 as shown in FIG. 2A and FIGS. 6 and 9, for example. In one example of LED attachment to the rod, LED 140 is mounted on PCB 141, which in turn is attached to rod 120. The PCB itself may be a hard board, i.e., green variety, or a flexible board with heat dissipation components. LED 140 may also include an optic lens chosen to direct light as desired from the LED into a light pipe or light bar in the rod. Particular features of the LEDs may be varied in many respects as will be described in greater detail below. The use of LEDs for lighting is advantageous in that it provides a cooler light with less heat than traditional forms of light. Further, because the lighting is positioned very close to the surgical site, it is highly efficient. Moreover, LEDs use less power for the same output when compared to other forms of lighting.

System 10 is configured so that LED 140 illuminates when it is supplied with power from battery 132. To light an area adjacent to rod 120, such as a surgical portal 6 created during surgery and bound by a plurality of rods (e.g., FIG. 2B), rod 120 is structured so that light emanating from LED 140 travels through the optic material of the rod, here, light pipe 160, and emanates from an end of light pipe on a lateral side of the rod. This is described in greater detail below but for illustration, a path of light through light pipe 160 is shown in FIGS. 5 and 6. Light pipe 160 is made of a clear engineered polymer structure. Alternatively, light pipe 160 may be made of other light transmitting materials.

Turning now to lighting rods 120 of system 10 and complementary optic structures in the form of light pipes 160, details of these elements are shown in FIGS. 3-7. Rod 120 includes a portal defining portion 120A having a cylindrical shape and extending from a top end 121A to a bottom end 123 of the rod, each end having a hemispherical tip. When attached to retractor 100, top end 121A is attached to arm 112 of retractor 100, while bottom end 123 is adjacent to a surgical site that is the subject of the operation. Thus, where surgery is directed to an intervertebral region of the spine, bottom end 123 of the rod will be the location on the rod closest to such region. Attached to the cylindrical portion 120A is arm engagement portion 125. As shown in FIG. 4 for example, arm engagement portion 125 extends from a top surface 121B to a tapered end 129 tapering to a cylindrical surface 124 of rod 120. Arm engagement portion 125 also includes teeth 126 and two slots 127. These features provide for adjustable securement of the rod to a retractor such as retractor 100 shown in FIG. 1. Thus, as noted above, top surface 121B is immediately adjacent to an arm of retractor 100 when secured to the retractor. Arm 112 includes protrusions corresponding to slots 127 to engage arm 112 to rod 120, while teeth 126 allow rod 120 to be adjusted in a direction of its length and relative to a position of arm 112, in increments corresponding to teeth 126. Cylindrical surface 124 of rod 120 as depicted in FIG. 3, also optionally includes notches 124A. Inclusion of notches 124A allows a shim or bridge slid onto the rod to be fixed at a desired depth of the rod, as described in greater detail below. Rod may be made of any material with sufficient stiffness to counteract tissue forces borne on retractor rods or blades, including metallic materials such as stainless steel, aluminum or titanium, for example. Other materials, such as polymers, may also be used. Inclusion of polymers in whole or in part in the rod allows for use of the rod as an insulator when the rod is structured for neuromonitoring.

Within top surface 121B of arm engagement portion 125 is an opening into an internal passageway extending through the combination of arm engagement portion 125 and cylindrical portion 120A. This internal passageway is in the form of a hole 122, and extends from a first opening 122A in top surface 123B through to a second opening 122B on cylindrical surface 124 on a side of rod 120, as shown in FIG. 3. The hole is interior to the rod so that hole is entirely defined by a circumferential interior surface within the rod. The trajectory of hole 122 is shown in cross-section in FIG. 5, and is at a shallow angle relative to a length of the rod. As depicted, an angle between an axis through hole 122 and an axis through rod is less than thirty degrees, but can be many different angles. Hole 122 is sized and positioned so that light generated at a light source at a top surface corresponding to top surface 121B travels and otherwise passes through hole 122 and out of cylindrical surface 124 at second opening 122B. To direct light through hole 122, a light pipe 160 is positioned within hole 122. Light pipe 160 is held in position within hole 122 as shown in FIG. 6 through a slip fit or a press fit. Other forms of securement of the light pipe within the rod are also contemplated. A position of hole 122 within rod 120 is designed to maximize a quantity of light exiting the rod and entering the surgical portal.

Light pipe 160 is made of a clear engineered polymer designed for optics. Examples of specific light transmitting materials that may be used for light pipe include clear acrylic, clear polycarbonate, clear polymethyl methacrylate ("PMMA") and glass fiber. Alternatively, other light transmitting materials may be used. Light pipe 160 is generally cylindrical in shape as shown in FIG. 7A and extends from a first end 162 to a second end 164. A position of light pipe in the rod and its size and material are all chosen so that the light pipe captures a maximum amount of light from the light source, e.g., LED, and directs it through pipe 160 to an opposite end, where it exits the pipe. At first end 162 is a knob shaped tip 161 as shown in FIG. 7A. Tip 161 is sized to sit within a funnel shaped surface 122C within hole 122, as shown in FIGS. 5 and 6. Thus, when light pipe 160 is disposed in rod 120, it remains held in place relative to rod 120. Toward second end 164, light pipe 160 tapers as shown in FIG. 7B. The taper of light pipe 160 includes an angled surface 165 with a radius of curvature matching that of surface 124 on rod 120. In this manner, when light pipe 160 is secured within rod 120, the second end of light pipe 160 exposed through second opening 122B in surface 124 is generally flush with surface 124. Surrounding angled surface 165 is beveled surface 166, dimensioned to reduce sharp edges on light pipe 160 to reduce danger to users and to minimize the risk of unnecessary cutting either of tools or bodily tissue during surgery.

Figure 8A:
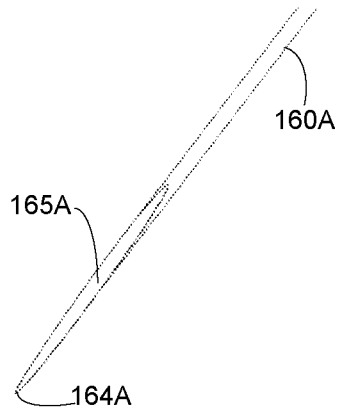
FIGS. 8A-8E are close up perspective views of light pipe distal ends according to separate embodiments of the disclosure.
Figure 8D:
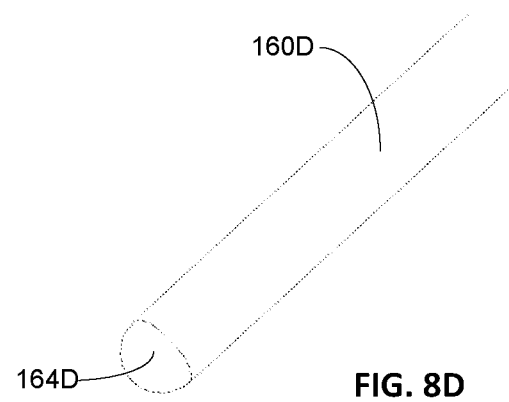
Figure 8B:
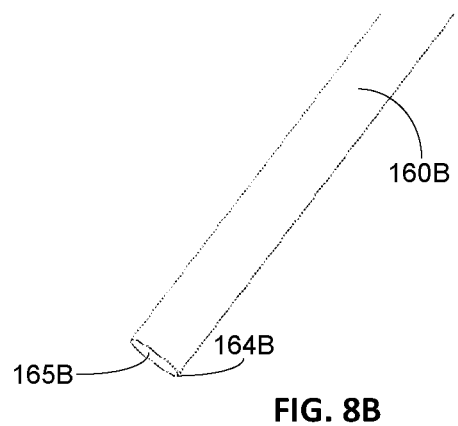
Figure 8C:
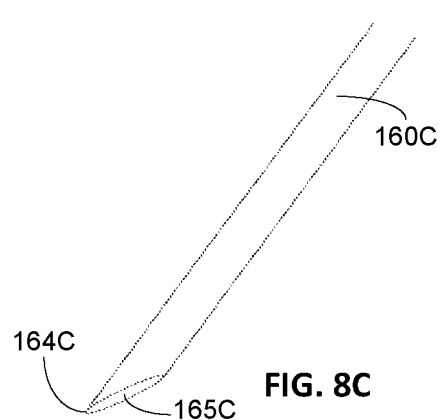
Figure 8E:
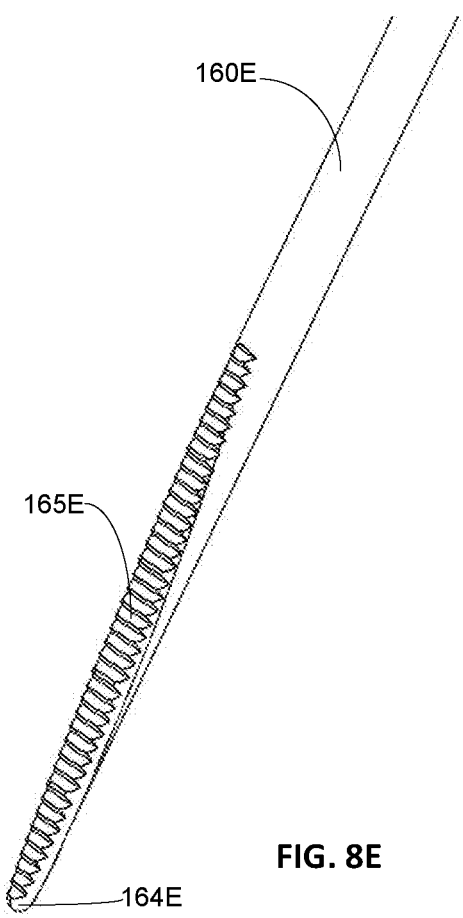

The light pipe used with rod 120 may be varied in many ways, such as those shown in FIGS. 8A-8E. Light pipe 160A shown in FIG. 8A is cylindrical and is similar to light pipe 160, although angled surface 165A immediately abuts the cylindrical surface of the light pipe. Light pipe 160B shown in FIG. 8B is cylindrical throughout and includes a flat end 165B normal to a length of the pipe. Such variant may be desirable where economic expediency is paramount. Light pipe 160C shown in FIG. 8C includes a back cut surface 165C. In this variant, light pipe 160C disposed within rod 120 directs light from the pipe into a wall of the surgical portal. In this manner, light reflects off of the wall of the surgical portal back into the portal. This path of travel for light entering the portal may provide for greater distribution of light within the portal. Light pipe 160D shown in FIG. 8D includes a hemispherical end surface 164D providing spread and distributed light into the portal. Finally, light pipe 160E shown in FIG. 8E includes a series of teeth, or steps 165E, toward distal tip 164E. Stepped surface 165 is curved with a radius in common with radius of surface 124 of rod 120 to create a flush surface when light pipe 160E is disposed within rod 120. Steps of stepped surface 165E are equally spaced as shown. However, spacing may also vary with distance from a first end of pipe 160E. This light surface, curved and stepped and also sometimes referred to as an optic surface, is designed to maximize light intensity and direct it over a working volume of the surgical portal. In further variants, a surface treatment may be used on stepped surface 165E. One surface treatment may involve roughening the surface of the light pipe or bar, the roughening performed to direct light into the surgical portal. Through the customization of step spacing, angles of the surfaces forming the steps, surface treatment, and the material itself, controlled micro mirrors may be created at the optic surface to tailor a direction of the light pathway.

Advantages of system 10 are numerous. The incorporation of lighting in the rods attached to a retractor is advantageous because it eliminates the need for a separate tool, equipment or device to provide lighting during surgery and it prevents clutter in the surgical portal. Other advantages include increased efficiency of lighting as the light source is on the rod itself in the form of an LED. The use of LEDs also generates less heat, reducing risk associated with high temperatures in the surgical field. Moreover, the use of a battery LED combination requires less input power and takes up less physical space than a light-box, for example. Yet another advantage is that an external battery may be connected to lighting rods with minimal wiring, in both size and quantity, thus reducing tripping hazards in the operating area including around various tables. There are also fewer wires in the sense that no wall socket connection is required with a battery, thus removing the risk of electrical shock. System 10 is also advantageous in that the rods are compatible with neuromonitoring elements and thus can be modified to perform neuromonitoring as described below. This is particularly helpful in lateral trans-psoas procedures where the proximity to nerves when creating or working within a surgical portal presents a serious risk. Another advantage is that temperatures in the patient undergoing surgery while light is generated are not excessive and in any event are lower than those when a light-box is used.

Figure 11:
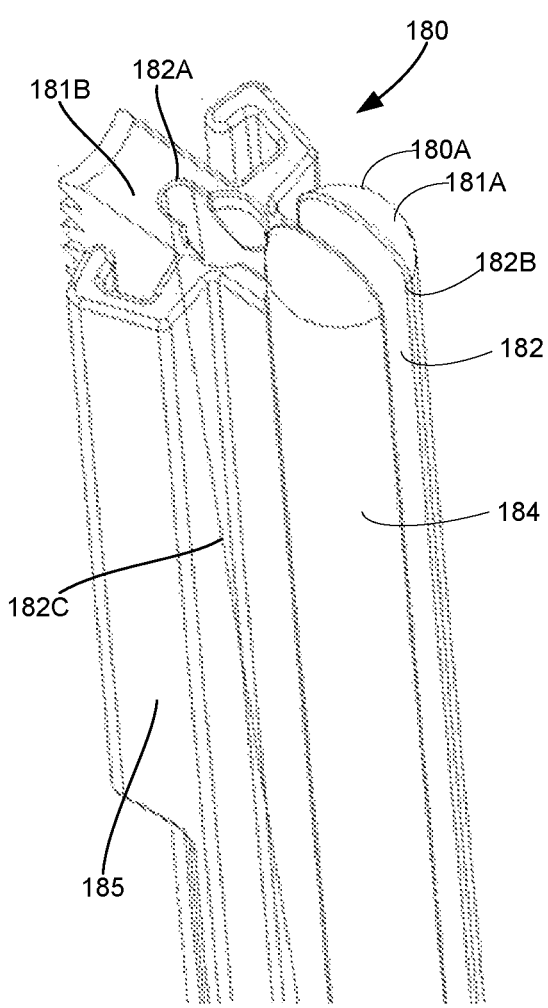
FIG. 11 is a close up perspective view of the proximal end of the rod of FIG. 9 without a light bar.

In a variant, system 10 may include rods 180, as shown in FIGS. 9-12, instead of rods 120. Each rod 180 includes a portal defining portion 180A having a cylindrical shape and surface 184, and an arm engagement portion 185. As depicted, exterior surfaces of rod 180 are generally similar to those of rod 120. Arm engagement portion 185 includes a top surface 181B extending to a tapered end 189 and is secured to cylindrical portion 180A on one side as shown in FIG. 9. In a manner similar to rod 120, arm engagement portion 185 includes teeth 186 and slots 187. Although the aforementioned outer features are similar to those of rod 120, instead of hole 122 within the rod, rod 180 includes slot 182, as best shown in FIG. 11. Slot 182 is defined by parallel interior walls, i.e., interior surfaces, extending through the portal defining portion 180A, i.e., cylindrical element, and part of arm engagement portion 185 of the rod. Slot 182 is bound laterally by a semicircular end surface 182A within arm engagement portion 185 at one end, and extends to an opening on cylindrical surface 182B at an opposite end. Slot 182 extends inwardly into rod 180 from surfaces 181A, 181B, and tapers via surface 182C becoming narrower toward bottom end 183 of rod 180 and eventually terminating at a location 182D. This is shown in FIG. 10 where light bar 190 is disposed in slot 182. The tapering interior edge is identified by reference numeral 182C, as shown for example, in FIG. 11. Although tapering interior edge is depicted as being semicircular in profile, such edge is not limited in that respect and may be defined by other profiles.

Figure 12:
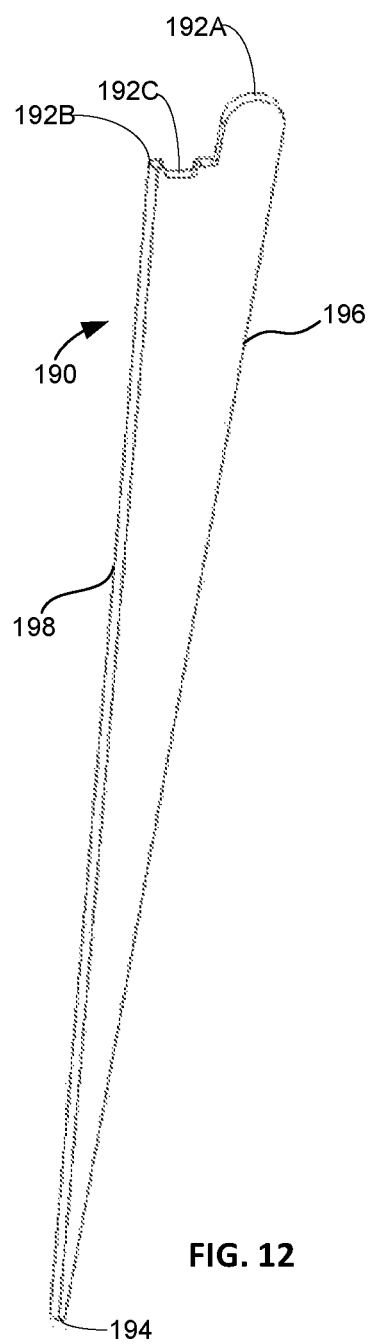
FIG. 12 is a perspective view of the light rod illustrated in FIG. 9.

Disposed within slot 182 is light bar 190, as shown separated from the rod in FIG. 12 and disposed within rod 180 in FIGS. 9 and 10. Light bar 190 includes a first end 192A, 192B and a second end 194 and is sized to correspond to a slot volume between top surface 181A, 181B of rod 180, tapering interior edge 183C, and a surface 184 of cylindrical portion 180A. Between first and second ends 192A-B and 194, respectively, light bar 190 includes a curved edge 198 on one side and an edge 196, on an opposite side, as shown in FIG. 12. Curved edge 198 is sized to nest in tapering interior end surface 182C along its length while edge 196 approximately matches a width of slot 182 on a surface 184 of cylindrical portion 180A between opening on cylindrical surface 182B and location 182D (FIGS. 10-11). Similarly, first end includes a curved tip 192A approximately matching dome shaped top end 181A of portal defining portion 180A of rod 180. For the remainder of first end 192 of light bar 190, a surface corresponds to top surface 181B of arm engagement portion 185, although includes a notch 192C aligned with a recess in top surface 181B. Notch 192C provides additional room on top surface 181B so that an LED or other accessories may be securely attached therein. The additional space created by the notch also minimizes the projection of the LED into the space above the rod. Additionally, the recess created by the notch allows an LED disposed therein to be positioned to direct a maximum amount of light into a light pipe or fiber optic cable(s) in the accompanying rod, thereby maximizing light transmission into the surgical portal.

A combined structure of rod 180 with light bar 190 held therein is configured so that a light source input into light bar 190, i.e., from an LED, distributes light through a length of light bar 190. In the embodiment shown in FIGS. 9-12, light bar 190 is configured so that light emanates through edge 196. This provides a source of light from the rod over a significant portion of a length of rod 180 without obstructing the surgical portal space on a side of the portal defining portion 180A facing inward when attached to a retractor.

Lighting system 10, including components such as the rod structures, light pipes or bars disposed therein, their combination, or the light source, e.g., LEDs, may be varied in many ways. For instance, the system may include a retractor with a total of two or more rods attached thereto. Additionally, any portion of the total number of retractor rods may be configured for lighting. For example, where a retractor includes five rods attached thereto, only two or three of the five rods may be designed with an optic material insert and LED. In another example where a retractor includes seven rods, one rod, six rods, or any number in between may be configured as lighting rods. Rods not configured for lighting may have solid structures securable to an arm of a retractor without adaption for the insertion of optic material inserts, such as light pipes or light bars.

A specific structure of each rod may also be varied. For instance, a portal defining portion of the rod defining a portal size and shape when such rod is retracted with other rods of a retractor, e.g., having a cylindrical shape in rods 120A, 180A, may instead have an oval, elliptical, rectangular, or other polygonal cross-sectional shape. Other possibilities include a cross-sectional shape having some curved faces and some cornered edges. For any of these rod shapes, a size or shape of the cross-section of the portal defining portion may vary over the length of the rod. Similarly, the portal defining portion may have a tapering characteristic, becoming smaller in cross-sectional size moving away from an end connected to the retractor. The portal defining portion of the rod may also vary in any manner contemplated in the '228 Publication. Consistent with these examples, an end surface of the portal defining portion may be any shape and is not limited to the dome shaped structures depicted. In one example, a distal tip of the rod is pointed and may function as an anchor. In other examples, the rod may have a width and/or diameter, or a length, to suit a particular application. For instance, a diameter of portal defining portions 120A, 180A of rods 120, 180, may be 4 mm. Similar principles apply to a length of the rods, and rods may have a length ranging from 80 mm to 200 mm. This applies to any portal defining portion of a rod as described above or otherwise contemplated in this disclosure. Rods may also be as described in the '841 Application. It should also be noted that within a plurality of rods included with a retractor, each rod may have a different hole and/or slot with corresponding clear polymer structure. In this manner, the lighting structure in each rod may be customized and may vary.

Turning to variants of the arm engagement portion of the rod, although FIGS. 3-12 illustrate rods with an arm engagement portion designed for securement of the rod to the retractor of FIG. 1, such structure may vary in any number of ways to accommodate a particular retractor structure used with the rod. In some examples, the arm engagement portion of the rod is sized and shaped so that the rod in which it forms a part is compatible with the retractors described in the '228 Publication. In other examples, the arm engagement portion may have a width wider or narrower than a corresponding portal defining portion of rod, it may extend a distance greater or lesser from portal defining portion than the arm attachment portions of FIGS. 3-12, and it may have any other shape to accommodate attachment to an arm or other actuation element of a retractor. A feature common to the arm engagement portion of the rods contemplated herein is its ability to be secured to a retractor and also that it provides sufficient dimensions and an open internal volume so that a light pipe or light bar with geometry sufficient to distribute necessary light during a surgical procedure may be held therein.

The hole or slot within the rod and the respective light pipe or light bar sized to be disposed in the slot may be varied in many ways. Beginning with the hole in the rod for the light pipe, a length of the hole as a fraction of the rod length may vary from that shown in FIG. 5, or similarly for slot in FIG. 10. If the length of the hole in the rod is shorter and the hole terminates higher on the portal defining portion than the hole shown in FIG. 5, then a length of the hole is at a steeper angle relative to a length of the rod than that shown in FIG. 5. Of course, if the opening of the hole on the top surface of the rod is closer to the portal defining portion than the hole in the rod of FIG. 5, then such angle will be shallower accordingly. These variations may be applied in any number of ways to vary the length and trajectory of the hole in the rod, and accordingly, the path of light through a light pipe disposed therein.

Similar principles apply to variants of a slot within a rod designed to house a light bar. For example, the tapering interior end surface defining an inner dimension of slot may be shallower or steeper than the tapering interior end surface shown in FIG. 11. In further examples, the hole may extend between any two surfaces of the rod. For example, the hole may extend from a rear side surface to a bottom surface of the rod. In other examples where the rod includes many surfaces, the hole may terminate over multiple surfaces at one or both ends. In other examples, a diameter of the hole may be larger or smaller than that shown in FIGS. 3-6. In other examples, the hole may have a non-circular cross-section or may include a taper toward an end remote from the top end of the rod. In still further examples, a rod may be configured to have more than one hole extending from a top end of the rod and exiting from a side surface of portal defining portion. Where there is more than one hole, such holes may be parallel or non-parallel. Non-parallel holes may be intersecting within the rod. In one example, a first hole extends through a central axis of a cylindrical portion of the rod, while a second hole is diagonal extending from a top surface of the rod to a surgical portal facing surface of the rod, crossing the first hole. In all of the above variations, a light pipe or pipes are sized to fit within a hole or holes of the rod. In any of these examples, an end of light pipe may have features as described in other embodiments herein. For example, light pipe may have an angled end surface at one end.

With regard to rods having a slot, a maximum dimension of the slot within the rod at the top surface between the arm engagement portion and the portal defining portion may be less or greater than that shown in FIG. 1. A thickness of the slot, measured between parallel interior walls of the rod, may be larger or smaller than that shown in FIG. 11. The thickness may also vary between an end of the slot on the arm engagement portion and an open end of the slot on the portal defining portion. Such variation in thickness may take the form of a tapering thickness. A slope of tapering interior edge surface may also vary from that shown in FIG. 10. These variations may provide for a light bar having a larger or smaller overall length (measured parallel to a length of rod) relative to the length of the rod than that shown in FIG. 10. Similar to the variants of the hole described above, the slot may extend between any two surfaces of the rod or more than two surfaces in some instances. An outer dimension of light bar, sized to fit within the slot of the rod, may be any shape sufficient to fit securely within the slot. For example, if a top end of portal defining portion of rod is not dome shaped, but rather has a flat end surface, then a corresponding top surface of light bar may be flat as well to create a flush surface when light bar is disposed in rod. In another example, a rod may include a slot and a hole separated and positioned behind it within a body of the rod. In such a configuration, the rod may house both a light bar and a light pipe.

Although the specific embodiments described include light pipes and light bars, it is contemplated that other shapes of a clear engineered polymer designed for optics may be used and disposed within rods structured for use with a retractor. A shape of the clear engineered polymer allowing for the direction of light from a top surface of the rod to a lateral surface of the rod located in at least one location on a length of the rod serves a function of providing light into a working volume adjacent to the rod during use.

Turning now to the LEDs included as part of the system, such LEDs may be as small as 1 mm and may be attached to a rod, a retractor frame, or to any other element of the system. In other examples, the LED may sit within a structure of the system without physical attachment, or may otherwise be positioned in any manner provided that light may be directed from the LED into the surgical portal. In other examples, the LED may be built internally into a light pipe or a light bar and positioned relative to the light pipe or light bar structure so that light is directed toward the surgical portal when the light pipe or bar is in position within a complementary rod. In still further examples, the light pipe or bar may occupy only a lower portion of an opening in the rod, and the LED may be disposed on top of the light pipe or bar as it rests internally in the rod. In such arrangements, wiring from a power source may be directed through an upper portion of the opening to the LED. The LEDs may have a color temperature within a wide range of possible color temperatures. Furthermore, LED 140 may be configured to have an adjustable color temperature. This provides surgeons with the option to tailor the color of light directed to the surgical site. For example, a yellow, lower color temperature may be desirable or conversely a blue, higher color temperature may be desired. In many instances, a surgeon may wish to adjust lighting in view of the lighting in the room where the surgery is taking place. In some of those instances, lighting may be adjusted to emphasize certain tissue within the surgical portal or to even the lighting within the portal. Adjustment may be desirable based on individual preferences and/or the condition of the patient undergoing surgery.

Where a retractor is attached to rods including a combined total of two or more LEDs, tailoring of a position and LED type for each LED may be used to create a desired lighting effect. For example, when LEDs are appropriately arranged on the rods of the retractor, particular combinations of LEDs within a group of LEDs may be activated to tailor the color temperature of the light within the portal. To provide a wide range of potential color temperatures, the group of LEDs may include individual LEDs covering a wide variety of color temperatures. In specific examples, where a retractor includes five rods, all five may have at least one LED, while three each have five LEDs, and of the three that each have five, each of those may have different combinations of red, yellow and blue LEDs. In another specific example, a lighting effect for a single rod arrangement may be varied through techniques that provide adjustable color temperature. One way this is achieved is through individual control of LEDs on the rods, so that having different combinations of LEDs activated yields a different lighting effect.

Red blue and green ("RGB") LEDs can also be used in place of traditional LEDs with the rods as described herein. RGB LED's include individually adjustable red, green, and blue light. RGB LEDs can similarly be incorporated onto or within rods and be adjusted to change color temperature. The color of RGB LEDs is adjustable using accompanying switches. To illustrate how a desired color is obtained with an RGB LED, one example involves production of a white light by applying low current, i.e., 10 mA, to each of the red, blue and green LEDs. In another example, production of a blue light involves applying a 10 mA current to the red LED and a 60 mA current to the blue and green LEDs. The change in current changes the wavelength value of the LED light, thus changing the perception of the light itself when viewed within the surgical portal. In the same manner that individual rods within a set of rods attached to a retractor may vary from one another, each rod may have LEDs tailored for a particular purpose than another rod on the same retractor.

Individual LEDs and RGB LEDs are also configured so that brightness is adjustable. For example, if a color temperature chosen during surgery is 3000 Kelvin, the brightness in lumens can be adjusted for that color temperature, for example, from 1000 lumens to 1200 lumens. One type of structure contemplated to provide adjustable brightness of LEDs involves the use of a potentiometer and resistors. In particular, each LED is accompanied by an LED battery switch, fixed position resistors, resistive circuits and a potentiometer. The potentiometer provides a means for a user to adjust the resistance in the circuit, thus controlling the brightness of the LED. One example of such a structure is a series potentiometer with a resistance range between 0-1000 k Ohms. The series potentiometer is specified for operation at 2.95-3.0 Volts and is powered by a 3V CR2 Lithium-ion battery. The potentiometer or an adjustable selection of fixed resistors are connected in series with the LED and battery to limit current to the LED. In other examples, one of ordinary skill will appreciate that other methods to control resistance to the current or even voltage may be used to control brightness of the LEDs. LEDs with adjustable brightness allow lighting to be used in a manner that can dramatically increase the lifespan of the LEDs. In one example, LEDs with adjustable brightness may continue to emit light over a period of days. It is contemplated that the above described features of LED lights may be applied to all embodiments incorporating LEDs as described herein. In any one of the above embodiments, one or more LEDs may be included within or otherwise as part of the light pipe or light bar. In this manner, it is possible to have a lighted rod without an externally attached LED.

Figure 13:
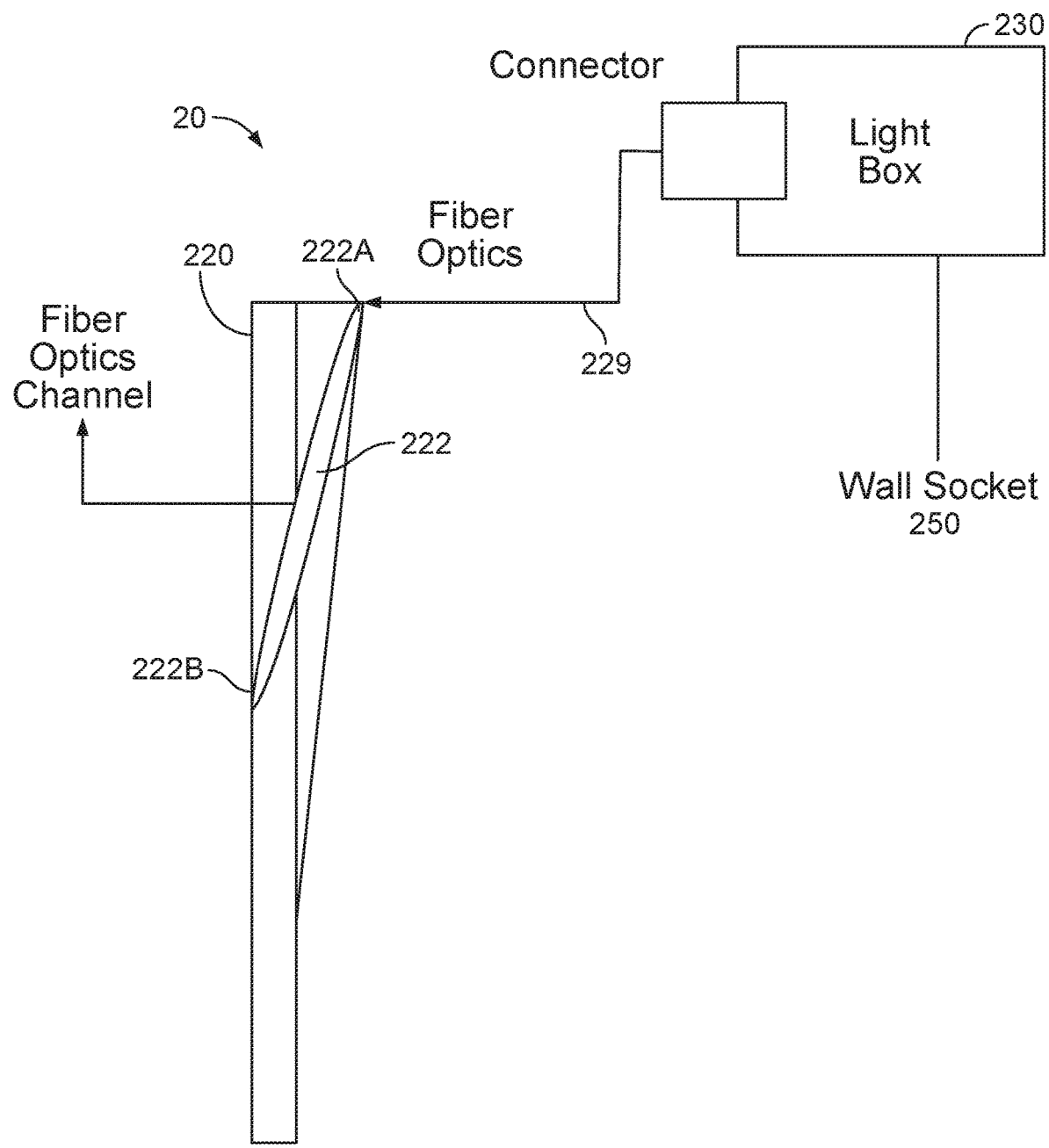
FIGS. 13-15 are schematics of separate embodiments of a system including a rod, a lighting source, and a source of power.

In another embodiment, a lighting system may be as shown in FIG. 13. Although rods of system 20 are not shown as attached to a retractor, similar principles apply as those described for system 10 for attachment to the retractor. In system 20, the light source providing light to a surgical portal is a light-box 230 which obtains power through the electrical grid via a connection to a wall socket 250. A fiber optic cable 229, or cables, connect light-box 230 to rod 220 configured for lighting. Light-box 230 is positioned at a distance from a retractor holding rod 220, for example, on a nearby table, so cable 229 is sized to have sufficient length to traverse a distance between the stationary location of light-box 230 and the position of the retractor as set for surgery. In some examples, light-box may be located three meters away from the retractor. As shown in FIG. 13, rod 220 includes a fiber optic channel 222 to direct light from an entry opening 222A where the rod receives fiber optics 229 to an exit location 222B toward a lower end of rod 220. The fiber optic cables may be in the form of a bundle with multiple individual cables or may be a single cable or bar. Each cable may include a single fiber or a plurality of fibers. The type and quantity of fibers used is largely a matter of design choice which may be made based on considerations including available space in the rod hole or options that simplify installation. Rods sized for placement of fiber optic cables are versatile in that such rods may also be repurposed for the placement of a light pipe therein. Advantages of system 20 include that it can be preassembled prior to surgery, that it is compatible with neuromonitoring, that temperature within the patient is not excessive during use because the light source is at a distance from the patient, and its low cost.

In variants of the system, a structure of rod 220 may be any contemplated by this disclosure to be employed with system 20. For example, system 20 may supply light via a fiber optic cable 229 to rod 180 with light bar 190 disposed therein. In this example, light emanates from an end of fiber optic cable and then travels through light bar 190. Light-box 230 may include fiber optic connections to any number of rods secured to a retractor. For example, if the retractor holds five rods, the lighting system 20 shown in FIG. 13 may be provided for one, two, three, four or five rods. Where more than one rod is configured for lighting, each rod may be supplied with light by separate fiber optic cables all connected to a single light-box. In other examples, multiple light boxes may be used as deemed desirable.

Figure 14:
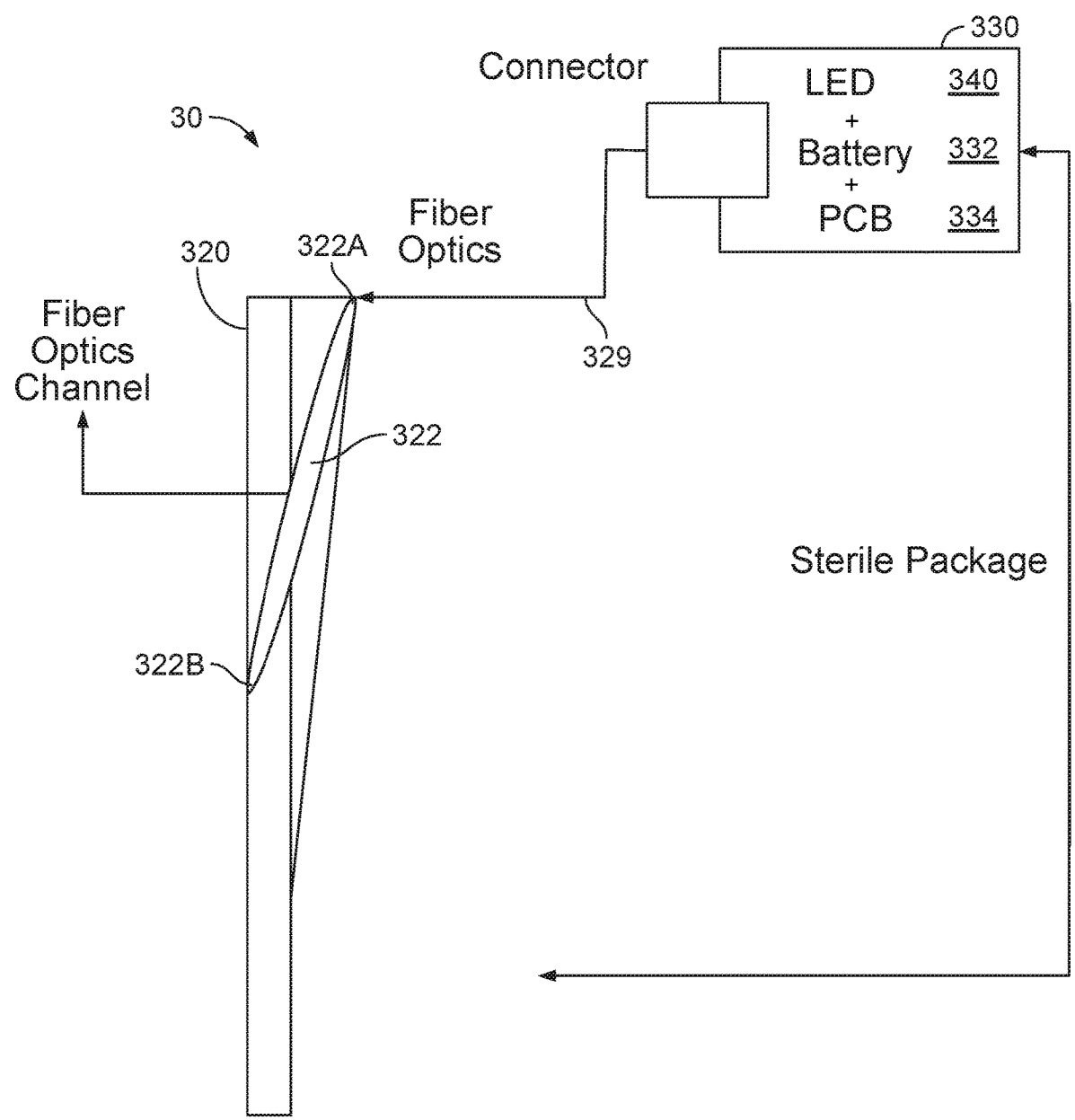

Another embodiment of a lighting system is shown in FIG. 14 in the form of lighting system 30. As with lighting system 20, lighting system 30 includes a fiber optic cable 329 to connect a light source 330 to a rod 320 or rods of a retractor, although here, the light source is an external unit 330 with an LED 340, battery 332 and PCB 334 disposed therein. Battery 332 powers LED 340 and system 30 provides light into a channel 322 in the rod through distribution of light through the fiber optic cable 329. In some examples, the fiber optic cable is a monofilament. Cable 329 may be attached to a top of rod 320 or may be inserted within channel 322 so that the distal end of cable 329 is at exit location 322B. External unit 330 is typically placed within approximately 1 m from the location of the retractor during surgery. As with system 20, external unit 330 of system 30 may include fiber optic connections to one rod 320 as shown, or any number of rods secured to a retractor, so that any number of rods may be configured to emit light from the light source. Advantages of this system are similar to those of system 20.

Figure 15:
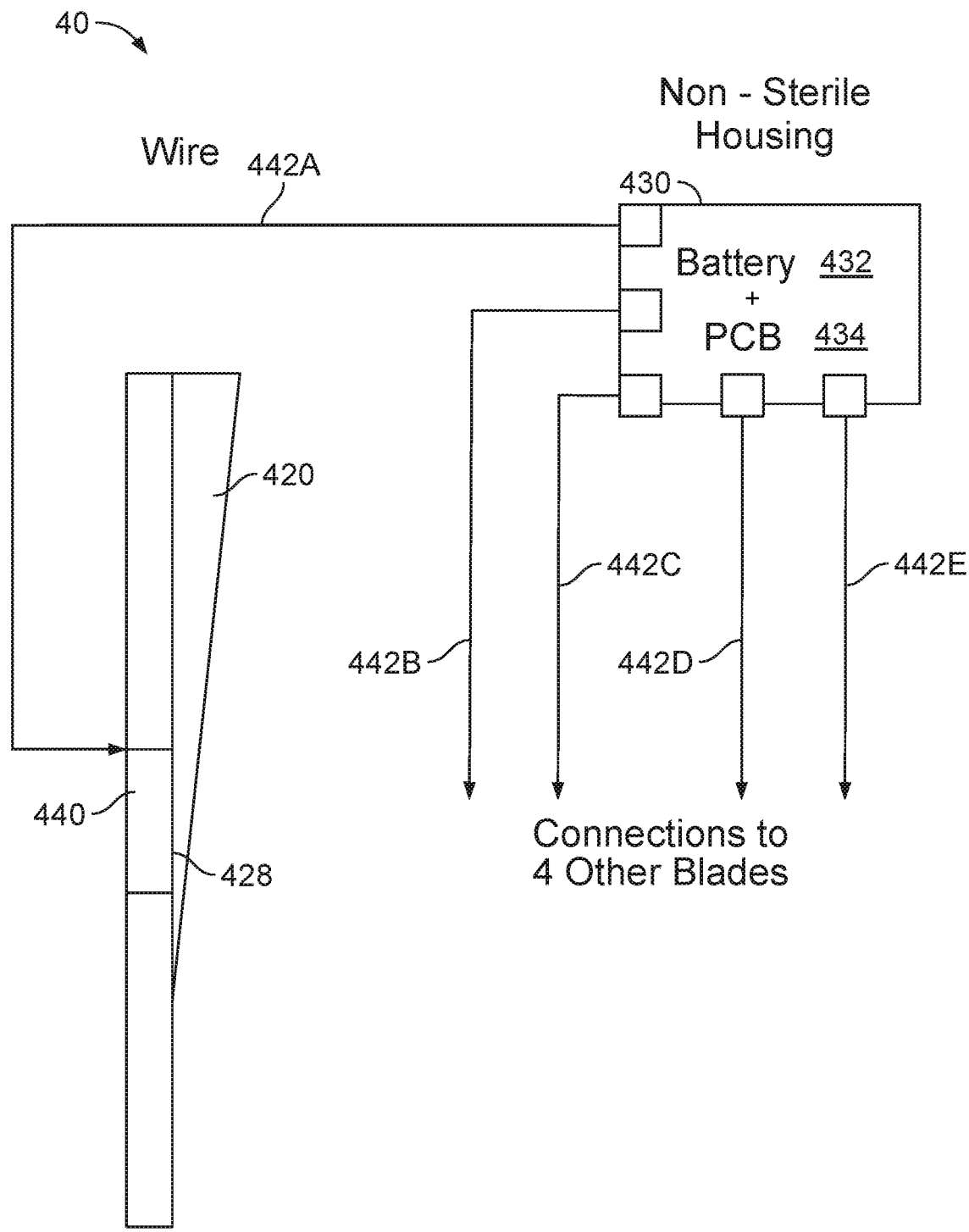

In another embodiment, lighting system 40 is as shown in FIG. 15. In this system, the source of light is an LED 440 disposed within the rod itself. In particular, rod 420 includes a pocket 428 sized for disposal of LED 440 therein. Securement of the LED may be by any means known to those of skill in the art, such as with an adhesive. Positioning of the LED on the rod is advantageous in that the efficiency of lighting is greatly improved as a distance the light must travel is minimal. In FIG. 15, the pocket is oriented to face inward toward a center of a group of rods attached to a retractor. As depicted, power for LED 440 is provided by an external unit 430. External unit 430 includes a battery 432 and a PCB 434. Battery 432 supplies power to LED 440 via wire 442. In one example, wire 442 extends from LED on rod 420, over a side surface of rod 420 to a top surface of rod, before continuing to external unit 430. This ensures that the wire 442 does not obstruct a portal held open by rod 420 and other rods, and that it will not be damaged by tools or other objects due to being loose within the surgical portal. An advantage of this system is that with the light source, i.e., LED positioned along the length of the rod, the efficiency of the light from the LED is very high, particularly compared with systems where a light source is several meters away from the patient.

As with other lighting systems described in this disclosure, system 40 is configured for securement to multiple rods attached to a retractor. As shown in FIG. 15, external unit 430 includes wire connections 442A-E to each of five rods, such as the five rod retractor shown in FIG. 1. In this arrangement, each rod connected to the external unit through a wire connection includes an LED disposed therein. Alternatively, in other arrangements, only some of the rods include features for lighting such as those present in rods 420. In some variants, any one rod may include two or more LEDs disposed thereon to create a desired lighting effect. Thus, for example, a retractor with five rods secured thereto may include two rods each having two LEDs disposed in respective pockets on a lateral face of the respective rods, while the other rods include no LEDs. It is contemplated herein that any combination of the above features may be used to produce a desired lighting effect. The LEDs of system 40 may be tailored in any way such as those described above for system 10.

In any of the embodiments contemplated herein incorporating fiber optic cables, it should be appreciated that any one of or combination of glass fiber and polymer fiber may be used. These can be used in conjunction with any power source or any light source. Further, it should be appreciated that the systems of the present disclosure are not limited to fiber optic materials, LEDs or light boxes for light sources. Indeed, valuable considerations when selecting materials include, among others, an efficiency of a material in transmitting light and its capacity to transmit heat.

In the context of light transmission, attenuation of light, or its loss of efficiency, is known as optical loss (i.e., power loss) and is measured in dB per unit of distance. Efficiency may provide insight into the comparative performance of otherwise different materials. Operational parameters for attenuation of light transmitting materials used may vary depending on the wavelength (nm) of a light source and indeed on other properties of the materials. In one example, bearing in mind that the visible light spectrum is between approximately 390 nm and 700 nm, a 700 nm fiber optic light source may have an attenuation of up to 10 dB/km. Expected operational temperatures may also drive light transmission material selection. Specifically for fiber optics, glass fiber may be chosen over plastic fiber where higher temperatures are expected, as safe operating temperatures are generally higher for glass fiber. In one example, glass fiber is used at temperatures up to 482° C., while plastic fiber is only used up to 70° C. In still further examples, a combination of glass and polymer fiber optic cables may be used to obtain a desired compromise between a transmitted amount of light (more from glass fibers) and heat (less heat with polymer fibers due to reduced transmission of infrared light). Thus, light may be transmitted through a rod with a polymer fiber optic cable from the light source to an entry area of the rod and then glass fibers through the rod itself, for example. Dimensions of the material used, attenuation properties, range of acceptable operating temperatures, among other criteria, may be considered when selecting fiber optic materials or any other materials that can achieve similar performance. With that in mind, it should be noted that the use of light sources other than those described herein for the various embodiments of the disclosure are also contemplated.

It is further contemplated that in other embodiments, the above systems for lighting rods may be used in combination with one another. That is, aspects of the various lighting systems described, such as system 10, 20, 30, and 40, may be used in combination with one or more of the others in lighting rods attached to a retractor in surgery. For example, a retractor may include a total of five rods, where two rods include an LED on a top surface of each respective rod to direct light through a body of the rod, as shown in FIG. 2A, while another three rods each include an LED in an LED pocket, as shown in FIG. 15. In such a configuration, a single external unit housing a battery may provide power to the LEDs of each rod. Similarly, other combinations of the systems described herein are contemplated, including arrangements where only some rods are configured for lighting and other arrangements where variants of the lit rods are employed. Variants may be different rod shapes, different lighting paths, different quantities of LEDs on a particular rod, and so on.

In each of the described lighting systems, including systems 10, 20, 30 and 40, for example, light intensity may be within a range between 10,000-40,000 lux. Additionally, for each embodiment of the system, such as the above described embodiments, a box may be used to bring all incoming power in on a single cord where two or more rods are configured for lighting, so that separate wires for each rod are only required from the box to the respective rod.

In any of the above described system embodiments, power may be supplied by a battery, a wall socket, or other AC power source. Further, any system may also employ wireless technology in place of traditional wire connections between a power source and an LED. Examples of wireless power transmitter technology that are contemplated include wireless power coils operating based on radiofrequency RF power, inductive power, microwave power and laser power, among others. In variants of the lighting system using wireless power coils, the power coils may be mounted on or in the rod structured for lighting. Coils mounted on rods or the retractor are receiving coils, while a transmission coil is positioned nearby to transmit power to the receiving coil. The receiving coils must completely loop around the rod or the retractor structure onto which they are secured. Power in the receiving coil is improved when the coil is on an exterior surface of the rod or retractor. To ensure power is received at the lighting device, e.g., LED, the rod also includes wires connecting the receiving coil to the lighting device. This method of bringing power to lighting elements is advantageous in that it reduces the space and clutter occupied by wire systems and thus provides room for other equipment in the surgical portal and outside of it, if needed.

In any of the above systems, the rods integrated with either an LED or fiber optic material may be structured as single use elements. Examples of disposable, single use rods include rods with injection molded fiber optic material within a hole of the rod. Surfaces of the rod are frosted, coated or masked where lighting is non-essential. In examples where an LED is attached to the rod, the LED may be overmolded onto the rod with associated wiring. Such an arrangement provides a fully integrated assembly. Frosting of non-essential areas and directional LED light may provide a glowing rod structure. Overmolding may be utilized in any manner deemed desirable as a matter of design choice to fix PCBs, LEDs, wiring and other accessories to the rod or to fix light pipe/bar to rod. In some examples, the power source, e.g., a battery, is built into the rod. In these examples, control of power to activate the LED(s) may be active of passive. For example, a switch or pull away tab may be used to turn on the battery, or a ball detent may be included on the rod that depresses on engagement with a retractor arm to turn on the battery.

In any one of the above system embodiments, one or more rods of a retractor may include neuromonitoring technology. Although the following examples describe neuromonitoring as applied to a single rod, it should be understood that such structures may be included in any number of rods attached to a retractor. In one variant, a rod is cannulated through its length and includes an electrode disposed therein. The electrode extends to an end of the rod distal to an attached retractor and exits from a surface of rod offset from its center. Alternatively, it may exit on a centerline of rod. To ensure any electricity flowing through the electrode is directed to the distal tip of the rod, the majority of the rod length is insulated with a polymer material, for example, while the tip includes an exposed metallic surface. In another variant, the rod does not include a separate cannulation for an electrode and instead the electrode is attached to a surface of the rod and independently insulated. Because the electrode is designed to transmit an electric charge to stimulate areas proximal to it in a surgical portal, other envisioned configurations include an electrode over the length of the rod that is exposed along the length of the rod, providing stimulation at locations in addition to the distal tip of the rod. As an alternative to having neuromonitoring on a rod, a wand may also be included which may be used in the same manner to stimulate nearby tissue including nerves. Other components in a rod with neuromonitoring include a separate electrode or electrodes proximal to the nerve or muscle of concern to function as a sensor and a computer system for sending stimulation signals to the rod and to receive data from the nerve response to the stimulation.

In another aspect, the present specification relates to lighting rod apparatuses. In one embodiment, lighting rod 120 and light pipe 160 are as shown in FIGS. 3-7B and as described above. In another embodiment, lighting rod 180 and light bar 190 are as shown in FIGS. 9-12 and as described above. A lighting rod may also be separate from a light pipe or light bar, or vice versa. Lighting rod structures may further be any other embodiment described in this specification in the system embodiments as a discrete structure, with or without an optic structure held therein.

In another aspect, the present disclosure relates to a method of assembling lighting rods for use in a retractor, such as rods 120, 180, including assembly as part of a system with power supplied to the rods. In one embodiment, rod 120 is assembled by placing light pipe 160 into hole 122 therein. Light pipe 160 fits within rod 120 through a slip fit, though in a variant, light pipe is press fit into the rod. Assembly of rod 180 is performed in a similar manner, where light bar 190 is slip fit or press fit into slot 182 of rod 180. In either of the above embodiments, an LED is attached to a top surface of the rod and a wire is connected thereto. The wire for the LED on each rod is then connected to a power source, if not already connected. In one variant, the power source is an external battery with a PCB, all disposed within a housing. In still other variants, other power sources are contemplated. To complete assembly as part of a retractor, each rod is secured to an arm of the retractor such as the arms shown in FIG. 1 or FIG. 16. Assembly as described above may be in the form of preassembly prior to distribution of the rods to an end user or the rod and optic structure may be provided to a user as separate components for assembly at the time of use.

In another embodiment, assembly of a rod is completed through attachment of an LED into a pocket 428 within the rod. This results in rod 420 as shown in FIG. 15. The LED is attached to a wire, which is run to an external battery such as that previously described. This method of assembly can be performed for one or more rods as needed to prepare all rods for attachment to a retractor. In other embodiments where lighting is channeled through fiber optics all the way to its destination, rods may be attached to arms of a retractor either prior to or after fiber optic cables from an external power source are run through a channel inside the rod to an opening toward a lower end of each rod, such as with rods 220, 320 as shown in FIGS. 13 and 14, respectively.

In other embodiments, the rods of the present disclosure are employed in a method of use whereby a surgical portal created through retraction of the rods of a retractor is lit using light directed from one or more rods. These methods may be employed in various surgical approaches, such as a lateral trans-psoas approach to the spine or in an anterior to psoas approach, i.e., a 45 degree angle approach, among others.

Figure 16:
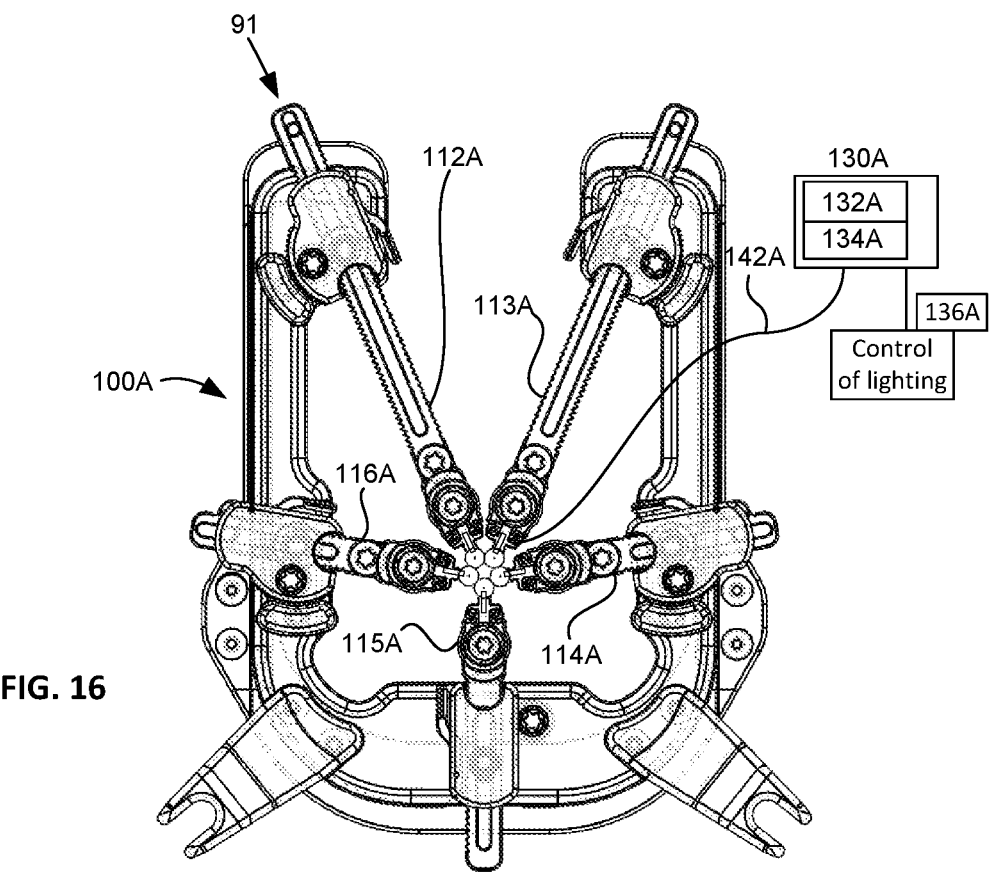
FIGS. 16-17 are top views of a retractor with a lighting system secured thereon in closed and open steps, respectively, of a method of use according to one embodiment of the disclosure.
Figure 17:
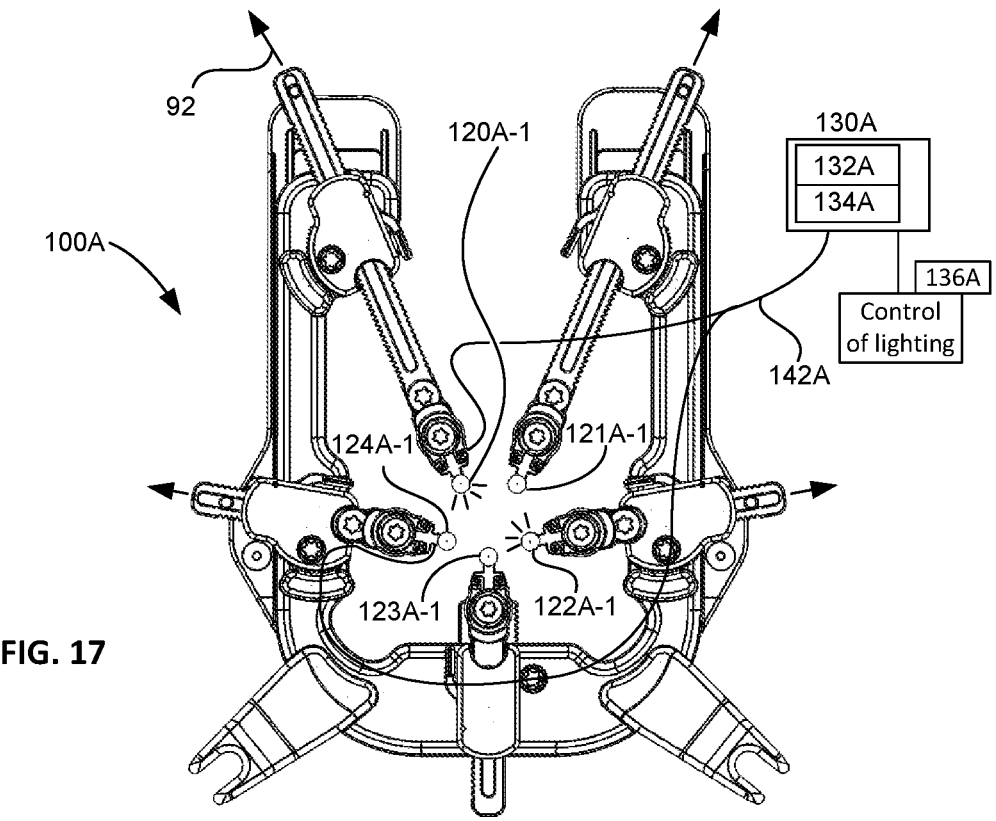

In one such embodiment, shown in part in FIGS. 16 and 17, a plurality of rods, each including a light source in the form of an LED, are attached to respective arms of a retractor 100A where the retractor is secured and docked in position. As shown in FIG. 16, these LEDs (one on each rod, not shown) are connected via wire 142A to an external unit 130A housing battery 132A. The arms are then moved in a direction shown by reference numeral 91 to ensure all rods 120A-1, 121A-1, 122A-1, 123A-1, 124A-1 are in a closed position. With rods secure and in the closed position, the closed rod structure is inserted into a body of a patient toward a target site based on a previously established alignment. Upon reaching a desired depth, arms 112A, 113A, 114A, 115A, 116A are once again manipulated and moved as shown by reference numeral 92 to retract rods to create an opening in the patient, as shown in FIG. 17. If necessary, a position of the arms may be adjusted to obtain a desired portal size.

At this time, or even prior to retraction, control of lighting on any one or combination of rods may be manipulated via an external control 136A, e.g., a switch, to create a desired lighting effect in the surgical portal within the patient. Alternatively, external control 136A may be configured so that lighting activates automatically upon a certain condition being satisfied, such as a certain amount of rod retraction or a ball detent mechanism on the rod that is depressed and thus activated upon engagement with a retractor arm. Upon activation, power is supplied from battery 132A to the LEDs either through wires 142A or a wireless connection. With rods 120A-1, 121A-1, 122A-1, 123A-1, 124A-1, lighting may emanate through an opening on a side of the rod if it is configured for inclusion of a light pipe therein, or over a length of the rod if it is configured for inclusion of a light bar therein. In this process, light originates with an LED and is then directed through the optic material of the light pipe or light bar so that it disperses through a side of the rod located facing the other rods, i.e., the surgical portal. In some desirable lighting configurations, two or three of the five rods are lit during the procedure. Lighting may be set in any number of ways as described above, with consideration given to external factors such as ambient lighting in the operating room. Thus, a wide range of lighting outcomes is possible through execution of this method. One advantage of this approach is that it reduces the time necessary to create a working portal having additional lighting needed to perform surgery. This is particularly relevant in the spinal surgery context, where a timeframe available to operate in the portal is typically only about fifteen minutes in duration.

When the procedure is complete, similar steps may be performed in reverse to shut down the lighting and to remove the retractor. Lighting may be deactivated in any number of ways, including automatically or through control by a user. Such deactivation may be at any time of the procedure deemed desirable. To remove a shim or bridge, a removal tool attached to the shim or bridge and described elsewhere in the application may be used or, where a cable is attached to the shim or bridge, such a device may also be employed for removal.

In variants of the method, the rods may channel lighting in any one or combination of the means described throughout the specification. For example, each rod may include a channel for a fiber optic cable therein. In another example, some rods may include an LED with light bar, while others may include a fiber optic cable therein. In further examples, appropriately sized rods may include fiber optic cables or a light pipe disposed therein, and, when desired, may be repurposed to incorporate the other light transmission structure. For instance, when a rod includes a light pipe disposed in a hole therein and the rod is attached to a retractor, the light pipe may be removed and fiber optic cables placed into the hole in place of the light pipe. The method of use remains the same in these varying combinations, although the manner in which light travels may vary. However, it is possible with certain combinations that additional equipment may be necessary to supply power to the rods, such as more than one power source.

In another embodiment, a preliminary step in the form of assembly of the rods as described above is performed initially prior to attaching the rods to the retractor. In this context, assembly includes connection of wires or fiber optic cables to the power source unless such step is performed after rods are secured to the retractor.

Figure 64:
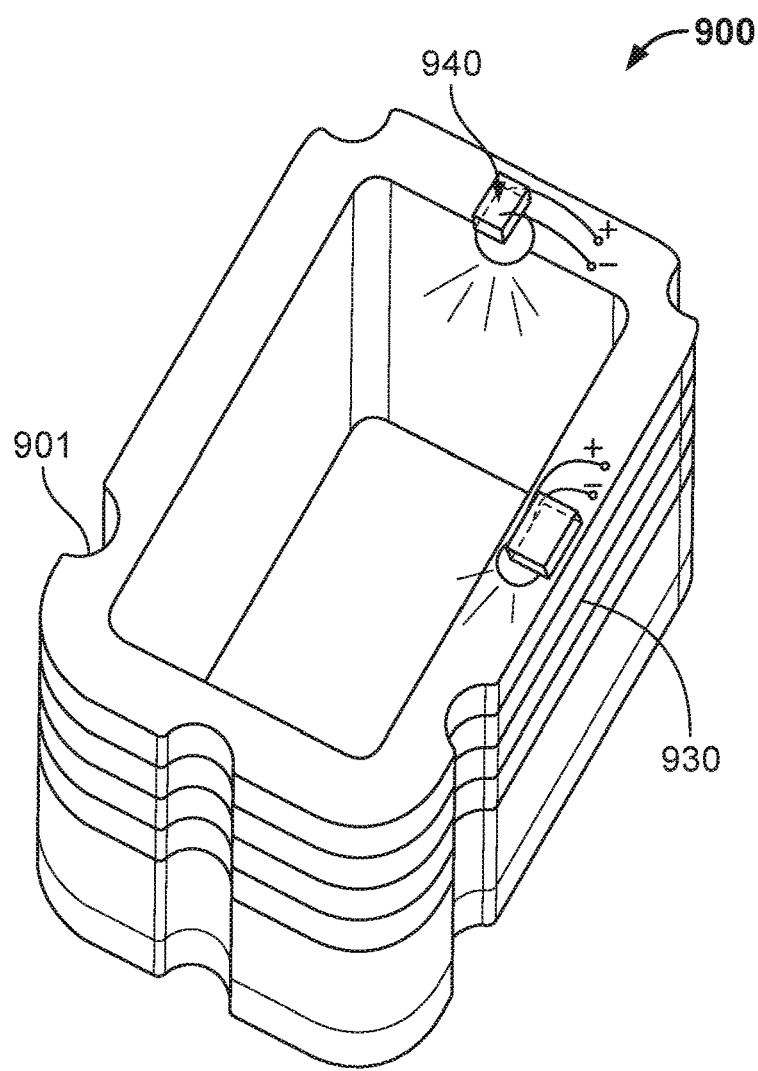
FIG. 64 is a perspective view of a retaining ring according to one embodiment of the disclosure.

In another embodiment, an open surgical portal held open by the rods may be supplemented by the insertion of one or more shims or bridges into the portal. A body clip of the shim or bridge may be slid over a rod and advanced as desired along the length of the rod. Rotation of the shim or bridge is generally prevented by the combination of the C-shaped clip of the shim or bridge engaged with the rod and the interference of the wings of the shim or bridge with the arm engagement portion of the rod if a force is applied to either wing. For example, comparing FIGS. 3 and 60, shim 600 inserted over rod 120 would be prevented from rotation by the presence of arm engagement portion 125. Alternatively, in some examples, some tolerance for a small amount of rotation of the shim or bridge may exist to reduce stress on the shim or bridge. In yet another alternative, the shim or bridge may freely rotate about a rod axis to reduce stress on adjacent tissue. For inserted shims, the shim may be advanced to a free end of the rod so that the pointed tip of the shim may engage a body surface such as a vertebral bone (not shown). When shims or bridges are inside the surgical portal, additional tissue is retained through their respective wing portions, i.e., wall structures. Additionally, where shims or bridges are configured with lighting, either through a wire or wireless connection, such lighting may be activated at a time desired by the user. Where rods include notches, grooves, or other features complementary to a bending clip of the shim or bridge, the shim or bridge may be snapped into place at a desired depth of the rod by resting within a notch, locking it in place. In the locked position, the finger on the free end of the bending clip engages the notch of the rod. Similar applications are contemplated for use of a ring, such as the ring shown in FIG. 64. In variants, any one rod may have a shim or bridge slid thereon followed by another shim or bridge. Thus, for example, a rod in a retracted position may have a shim on its distal end and a bridge at its middle depth. Depending on a length of the rod, more than two shims and/or bridges may be attached to a single rod, as desired.

In other embodiments, once a surgical portal is opened through retraction of the rods, a wand may be attached to a power source at one end, such as a battery, and a frame of the retractor at another end to direct light into the portal. In a variant, the wand may be secured to a rod, a shim or a bridge to direct light into the portal from those locations. In another application, the wand connected to a power source may simply be waved within the surgical portal to direct light as desired.

In still further embodiments, either the rod(s), shim(s), bridge(s), ring(s) or wand(s), or a combination of these, may include an electrode and other elements tailored to provide a neuromonitoring function when placed into the surgical portal. Particular elements and strategy for performing neuromonitoring may be chosen based on a surgeon's preference and/or particular circumstances surrounding the surgery. In one example where a rod is used for neuromonitoring, the rod may be rotated upon insertion to gather readings in multiple directions when the electrode is offset on the rod.

In any of the above embodiments, the lighting on the various rods and any shims or bridges inserted into a surgical portal can be manipulated in any number of ways through external control, e.g., via switches, to create a desired lighting effect. For example, brightness, color temperature and other variables can be controlled through the voltage supplied and the color and quantity of the LEDs as distributed over the various rods.

In another embodiment, rod lengths and/or rod types are selected prior to attachment to a retractor to customize the procedure. Where such selection is made, rods may be selected based on prepared modules having particular features ready for use. For example, a packaged module may include five rods and five light bars, so that a surgeon may open the module, assemble each rod, and then attach to the retractor.

In any of the above embodiments, assembly of rod components may occur prior to reaching an end user or at the time of surgery. Examples of assembly at the time of surgery include inserting a light pipe or light bar into a rod counterpart, or snapping in an LED to a pocket in a rod, such as with rods of system 40.

In any of the above embodiments, it is further contemplated that the order of steps performed may be altered as desired. For example, lighting may be activated prior to attaching the rods to the retractor. It should also be noted that the above methods may be performed with any of the systems, apparatuses and kits as described herein.

In the many aspects of the present disclosure, it is contemplated that structural features described for one embodiment may be included with similar structures found in other embodiments.

Panel Bridges

Figure 18:
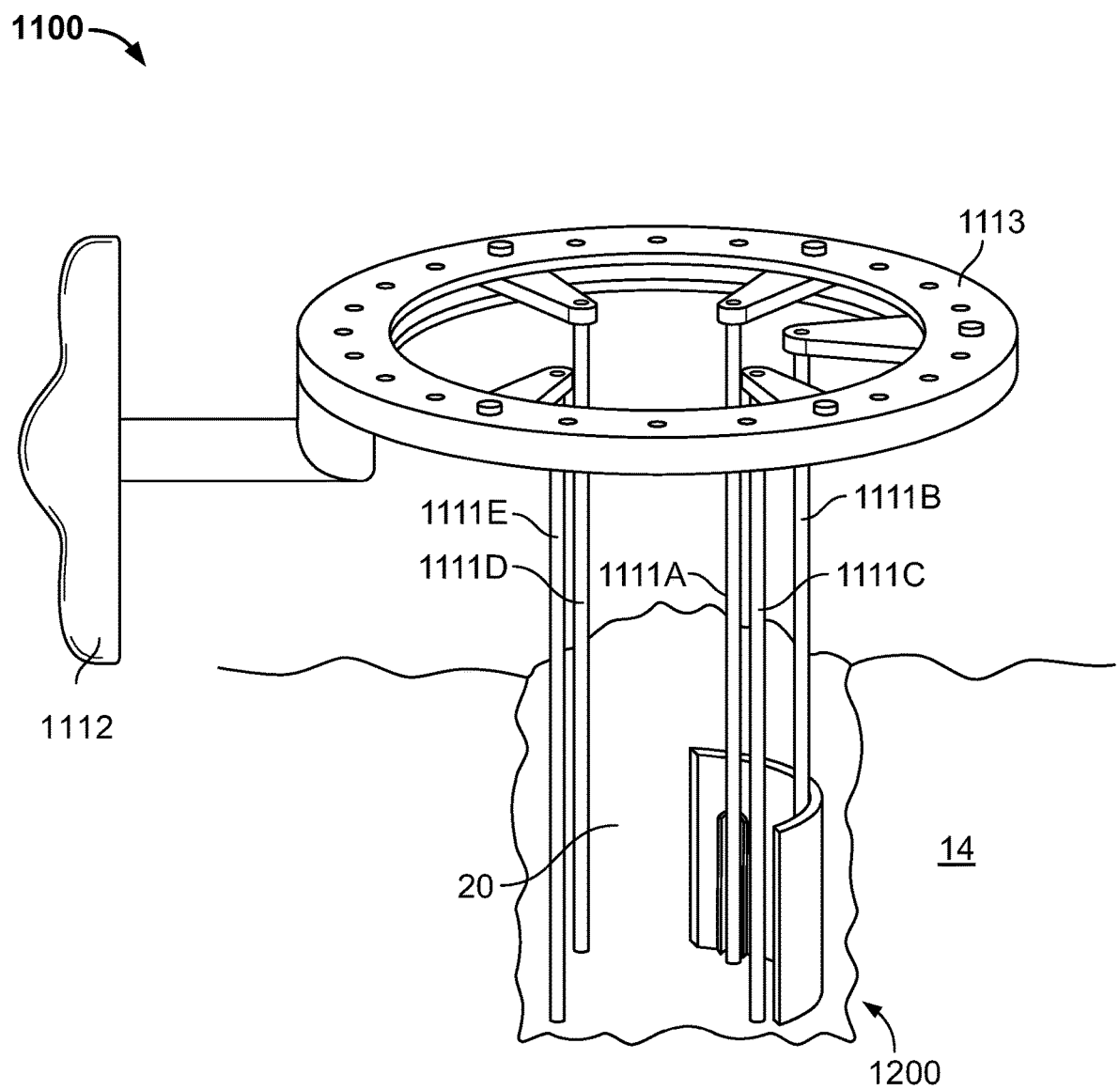
FIG. 18 is a perspective view of a retractor system with a bridge according to one embodiment of the present disclosure attached to an adjustable rod structure.

With a portal to a surgical site created in the body, further structures are often inserted to maintain the portal size and prevent tissue creep. Surgeons typically rely on external devices as a source of lighting which are brought to the surgical site separately from the retractor system and structures integrated with the retractor which are used for creation and maintenance of a portal in the body. Unlike known structures and devices, however, bridges as described herein, such as panel bridge 1200 shown in FIG. 18, are easy to use structural elements that can be inserted into a portal with a retractor in place and maintain a portal shape and size during surgery. Bridges provide securement or contact with one or more rods within the portal and span a surface area of a wall of the portal to abut tissue and otherwise prevent its entry into the portal. Bridge structures are advantageous in that they have a thin structure to minimize reduction of the portal size due to the physical space taken up by the bridge while also having strength to withstand loads from adjacent tissue. Bridge structures as described in the embodiments herein are also advantageous in that they can be modified to include in situ lighting which provides better lighting at the surgical site to differentiate muscle tissues and the like, uses less space within the portal, and also minimizes complications outside of the portal in the form of excessive wire and/or cable extensions and large and/or distant power supply requirements to support the lighting device.

Various aspects and embodiments of the present disclosure are now described as illustrations of how the above advantages are realized.

In one aspect, bridge structures are panel bridge structures of a variety of configurations. Panel bridges are structured to engage with rods of a retractor and, in some instances, extend between rods. Panels of the bridge are also, in some instances, sized and structured so that more than one bridge is stackable on a given rod. Panel bridges include features to clip onto or otherwise contact at least one rod of a retractor system and are sized to maintain a portal opening and to otherwise improve the surgical process when advanced a desired amount into a surgical portal. As with other bridge structures, among other functions, panel bridges hold back tissue and retract it. Typically, bridges are placed in three different ways: (1) behind rods, such as with offset bridge 1200 shown in FIGS. 19-20, (2) between rods, or (3) stacked over one another on a single rod.

Figure 19:
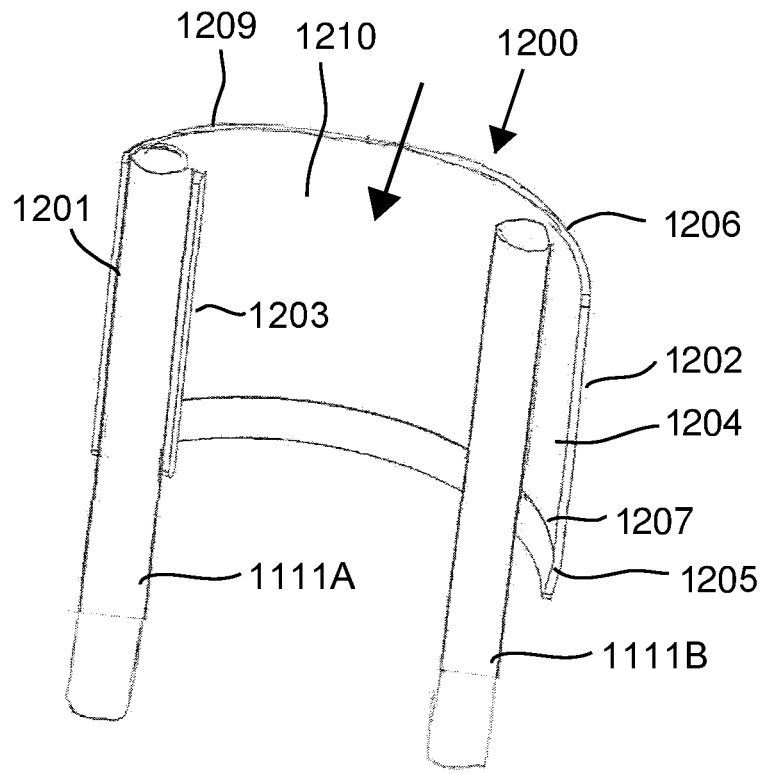
FIGS. 19-20 are perspective views depicting the use of an offset bridge according to one embodiment of the disclosure.
Figure 20:
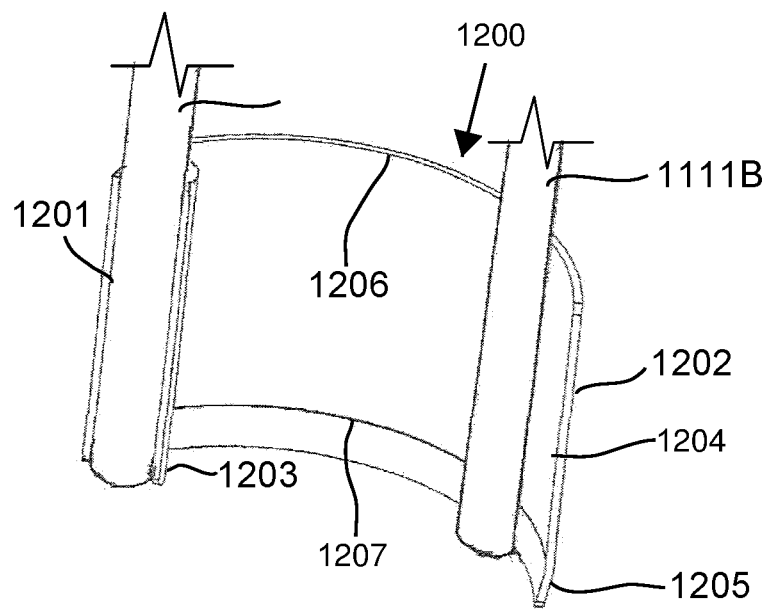

In one embodiment, an offset bridge 1200 is used to maintain the size of the tissue portal and prevent tissue creep as shown in FIGS. 19 and 20. As shown in FIG. 19, offset bridge 1200 includes a support structure in the form of a clip 1203, a main panel portion 1204, and an angled panel portion 1205.

Main panel portion 1204 includes a concave surface 1210 and a convex surface 1209. Main panel portion 1204 has a length between a top end 1206 and a bottom end 1207 and a width between a first side 1201 and a second side 1202. As shown in FIG. 19, the length of main panel portion 1204 is generally linear while the width is curved with a somewhat varying radius defining the curve. The length of the panel is driven by practical considerations for what may feasibly be inserted into a portal and also what length is necessary to obtain the desired effects of the bridge, i.e., retraction and withholding of tissue from the portal. The width of bridge 1200 is sufficient to encapsulate two rods 1111A-B, shown on concave surface 1210 of bridge 1200 in FIGS. 19 and 20, where rod 1111A is engaged with clip 1203 while rod 1111B is in contact with concave surface 1210. The curved width of bridge 1200 generally corresponds to a curved perimeter of the portal in an intended or actual surgical setting. This means the bridge shape mimics that of the portal so that the intrusion of the panel bridge into the portal is minimal.

Below main panel portion 1204 is angled panel portion 1205 extending across the width of offset bridge 1200 in concert with main panel portion 1204. As seen in FIGS. 19 and 20, angled panel portion 1205 is tapered away from convex surface 1209 toward a center of the portal when bridge 1200 is engaged with a rod within the portal. The taper of angled panel portion 1204 allows for a smoother insertion and minimizes tissue damage. In a fully advanced position at a distal end of a rod, angled portion 1205 provides a partial toe-in for the portal, and tissue behind the bridge may creep inward to an extent of the taper. A thickness of main panel portion 1204 and angled panel portion 1205 are selected so that offset bridge 1200 has capacity sufficient to retract rods during insertion of bridge 1200 and to protect a portal from tissue creep during surgery. Of course, thickness is considered in view of the material used for these components, described further below. This design also maintains the portal boundary, another important advantage of the panel bridge.

As alluded to above, convex surface 1209 is designed to be a tissue facing surface while concave surface 1210 is designed to be portal facing when offset bridge 1200 is inside the portal in the body of the patient. Put another way, concave surface 1210 defines part of an outer wall of the portal when in position within the portal. To enhance the function of bridge 1200 in view of its intended placement, convex side 1209 of main panel portion 1204 is smooth with low friction, particularly relative to concave side 1210. This surface property is shared among the panel bridges illustrated in FIGS. 19-23, and indeed, among at least some embodiments of the other bridge structures described in this disclosure. The smooth property of convex surface 1209 is advantageous in that it is configured to retract tissue upon advancement over a rod into a portal and further to aid in maintaining protection of the portal from tissue surrounding it. For example, the smooth surface keeps tissue from sticking to the bridge, thereby reducing the possibility that tissue may pull the bridge out of position and compromise the portal size and shape during surgery.

Clip 1203 is defined by a C-shaped channel and is positioned on concave surface 1210 adjacent and parallel to first side 1201 and extends over the combined length of main panel portion 1204 and angled panel portion 1205. A thickness and exact shape of clip 1203 are determined as a function of its ability to engage rods through friction, compression, or with the use of a key feature, among other engagement mechanisms. The position of clip 1203 on offset bridge 1200 shown in FIGS. 19 and 20 provides for a maximum available width of bridge 1200 on one side of clip 1203 so that bridge 1200 spans a distance greater than that between two rods in a retracted condition. In this manner, bridge 1200 is configured so that it may envelope a rod adjacent to a rod disposed in clip 1203, such as rods 1111A-B, where rod 1111A is engaged by clip 1203, as will be described in greater detail below. Clip 1203 is sized to securely engage a rod such as rod 1111A while allowing for the bridge 1200 to be rotated about the rod. This adjustability ensures bridge 1200 may be used with minimal damage to tissue while maintaining the intended size and shape of the surgical portal. Clip 1203 is also designed so that rod 1111A can easily be removed from clip 1203 when not in use. Clip 1203 is further configured so that a distance between a face of a rod when disposed in the clip and concave surface 1210 of the bridge is minimized to limit portal space taken up by the bridge. For instance, a thickness of the clip structure is minimized for this purpose, while still having structural capacity to retain rods. Moreover, the clip is sized, made of a material and secured to the main panel portion, or other portions of the bridge, in a manner so that it can easily be engaged to and removed from a rod of a retractor without compromising its structural integrity. In this manner, the clip is designed so that it will not crack or otherwise break from the main panel portion during use.

Panel bridges may be made of a metal material such as aluminum or titanium. Between these, aluminum is used when greater radiolucency is desired. Other than metals, other medical grade materials are also contemplated, such as stiff polymers including polycarbonate or polyether ether ketone ("PEEK"). Carbon fibers may be added to polymers to provide a structure with greater stiffness. A common characteristic of polymers, carbon fibers and other similar materials not specifically mentioned here is that such materials are inherently radiolucent and are designed to maintain stiffness under expected operating conditions, such as those existing in the spine. In some examples where plastic materials are used, a metal strip may be added for reinforcement of the bridge. Use of radiolucent materials for the surgical procedures as contemplated herein is advantageous in that it reduces obstructions that could otherwise appear in images generated during a fluoroscopy procedure. It is also contemplated to provide radiopaque markers within the radiolucent material, for identification of the positioning of the bridges on an X-ray or the like.

Figure 21:
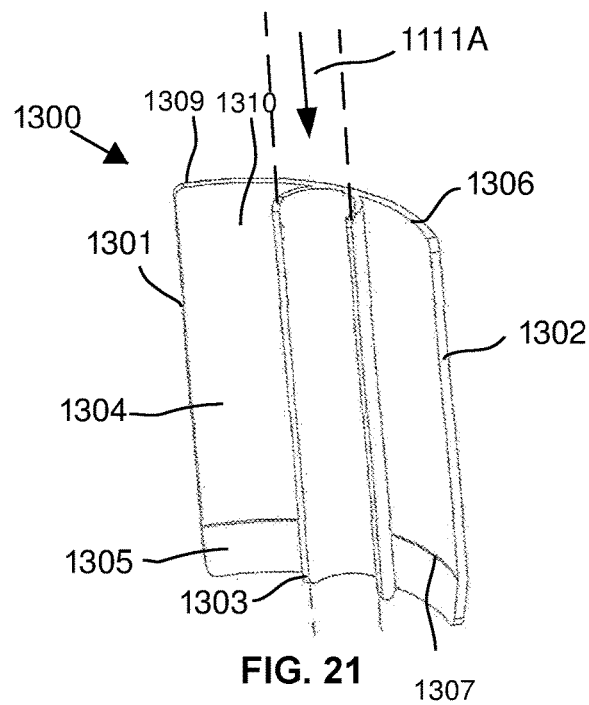
FIG. 21 is a perspective view of a centered bridge according to one embodiment of the disclosure.

In a variant, a centered bridge 1300 is shown in FIG. 21. Centered bridge 1300, along with the bridges shown in FIGS. 22 and 23, share many features in common with offset bridge 1200 and like reference numerals refer to like elements. For example, bridge 1300 includes a concave surface 1310. As with bridge 1200, centered bridge 1300 includes a clip 1303 on concave surface 1310 extending parallel to a length of bridge 1300. However, unlike bridge 1200, clip 1303 is positioned at an approximate center of the width of bridge 1300 midway between first side 1301 and second side 1302 so that portions of the width extending in both directions from clip 1303 are approximately equal. Centered bridge 1300 is configured for engagement with individual rods for the same purposes as outlined for bridge 1200, such as improving the definition of the portal opening.

Figure 22:
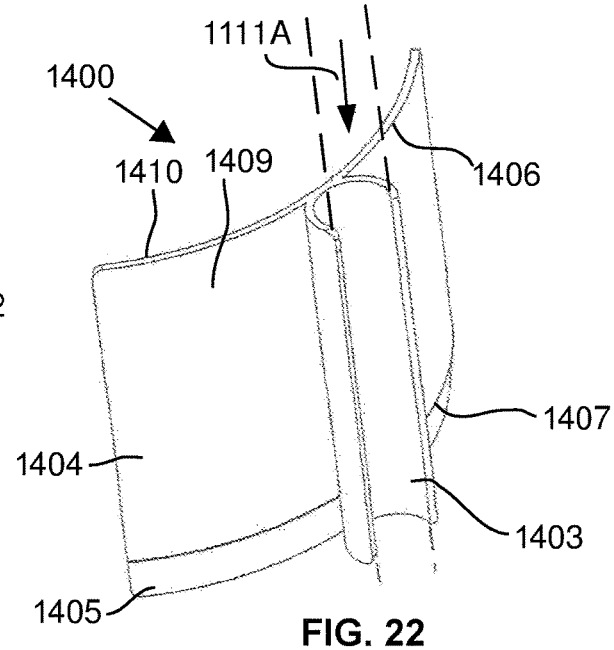
FIG. 22 is a perspective view of a reverse centered bridge according to one embodiment of the disclosure.

In another variant, the panel bridge appears as shown in FIG. 22. Reverse centered bridge 1400 includes a clip 1403 centered on a width of bridge 1400 as in bridge 1300. However, clip 1403 is positioned on convex surface 1409 of bridge 1400, unlike bridges 1200, 1300. Reverse centered bridge 1400 is configured to engage with rods of retractor assemblies, although the portal size may be smaller than with other bridges positioned in the same portal due to the position of clip 1403.

Figure 23:
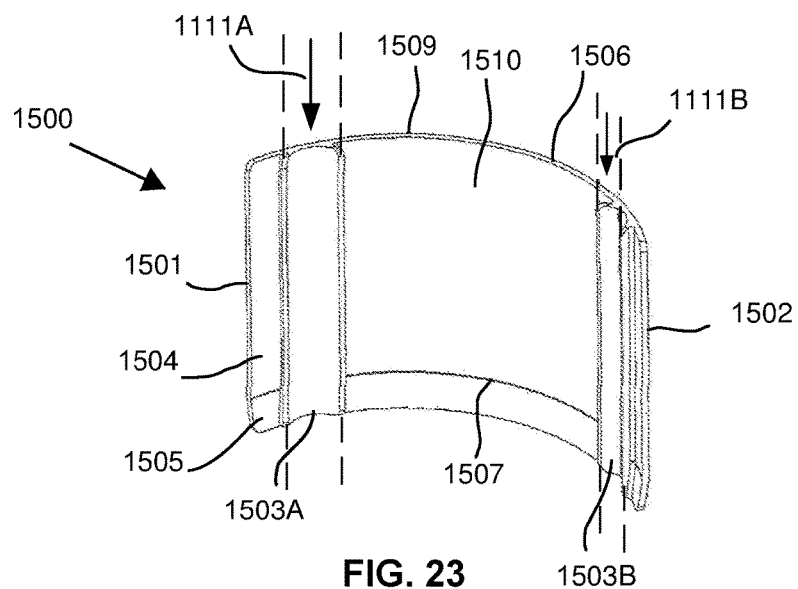
FIG. 23 is a perspective view of a dual engagement bridge according to one embodiment of the disclosure.

In yet another variant, the panel bridge appears as shown in FIG. 23. Again, dual engagement bridge 1500 shares many features in common with the other panel bridges described. However, bridge 1500 includes two clips 1503A-B on a concave surface 1510, both extending parallel to a length of bridge 1500. A first clip 1503A is adjacent to first side 1501 while a second clip 1503B is adjacent to second side 1502. As described in greater detail below, bridge 1500 is configured to engage with two rods of a distracted retractor assembly via clips 1503A-B. The inclusion of an additional clip further stabilizes the bridge within the portal thus further reducing the risk of misalignment of the bridge and any tissue damage or creep that could result from such occurrence. In one example, the dual engagement bridge is 20 mm in length, 28 mm wide, has a 22 mm outer envelope radius, and has a 4 mm clip radius. It is contemplated to orient clips 1503A and 1503B in a manner which provides for further distraction of the rods during insertion of the bridge.

Figure 46:
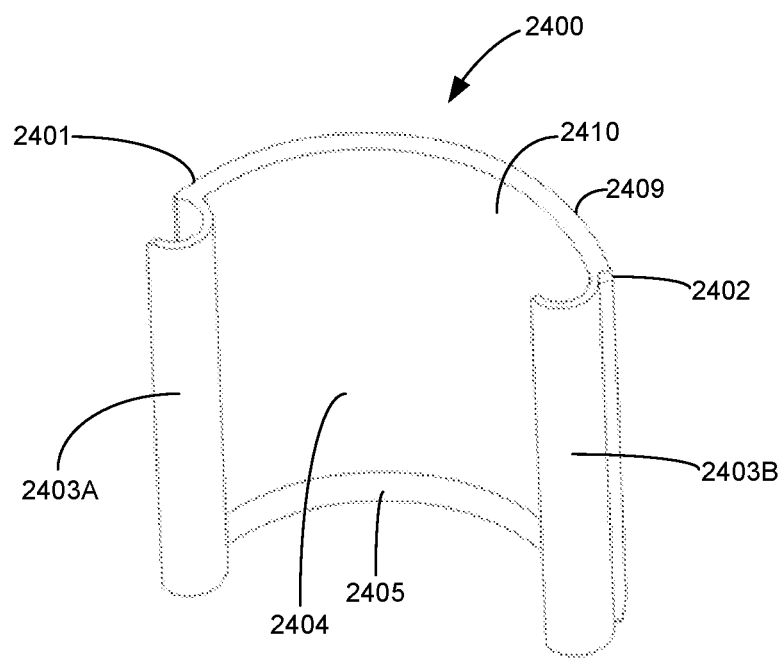
FIG. 46 is a perspective view of a dual engagement bridge according to one embodiment of the disclosure.
Figure 47:
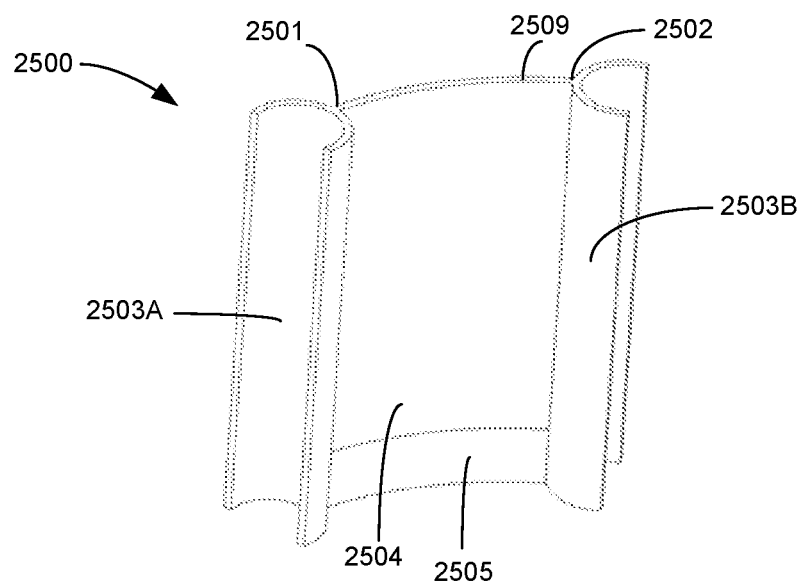
FIG. 47 is a perspective view of a dual engagement bridge according to another embodiment of the disclosure.

Additional panel bridge embodiments are illustrated in FIGS. 46-49. These panel bridges are similar to those shown in FIGS. 19-23, and like reference numerals refer to like elements. To the extent features of these bridges are not explicitly described, their characteristics may be as described for the previously mentioned panel bridge embodiments. FIG. 46 shows a dual engagement bridge 2400 with C-clips 2403A-B at each end 2401, 2402 of its width. The bridge has a convex outer surface 2409 designed to abut tissue upon insertion over rods disposed within a body of a patient. Each C-clip extends from an inner surface 2410 of the bridge and has an arc similar to the other, the C shape positioned so that its structure does not extend past a radius of the bridge structure. The unique positioning of clips 2403A-B is such that when engaged with rods of a retractor, the rods pull sides 2401, 2402 away from each other to create tension in panels 2404, 2405. Because of the tension in bridge 2400, the panels incur less deflection under load, leading to less physical incursion of the bridge into the portal space than would otherwise occur. Additionally, load on the convex surface of the panel causes clips to apply force to any rods engaged thereto, providing another means for holding open the rods. In a variant, a bridge may include only one of the two clips shown in FIG. 46, and the tension in the bridge may still be created when the end of the bridge remote from the clip is placed between a rod and tissue. FIG. 47 shows another dual engagement bridge 2500 with clips 2503A-B at its ends, though here, the clips face outward away from the bridge panels 2504, 2505. This bridge offers similar advantages as those described for the bridge shown in FIG. 46, though its incursion into the portal space is somewhat greater as panels 2504, 2505 extend along a centerline of the rods as they define a perimeter of the portal.

Figure 48:
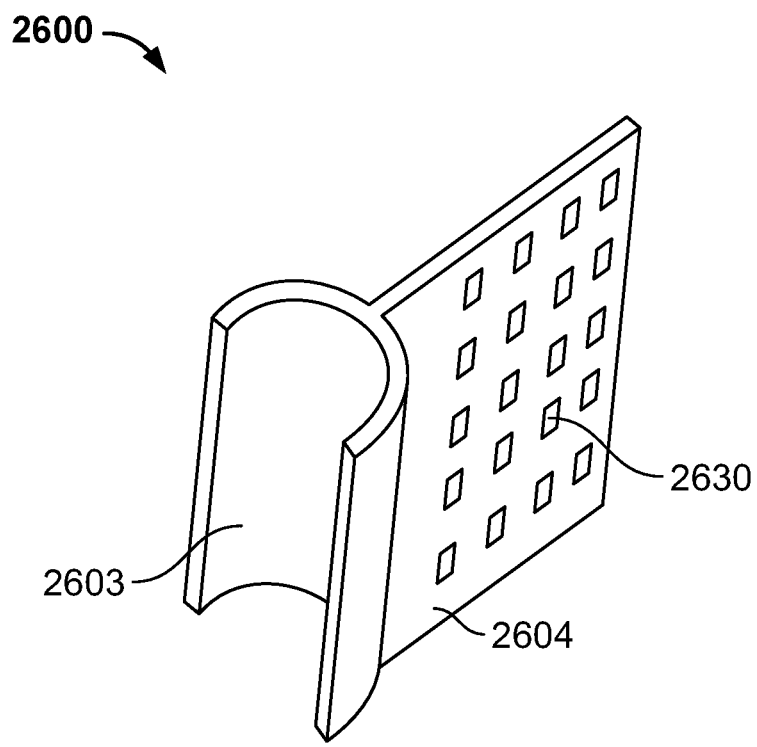
FIG. 48 is a perspective view of a saloon door bridge according to one embodiment of the disclosure.
Figure 49:
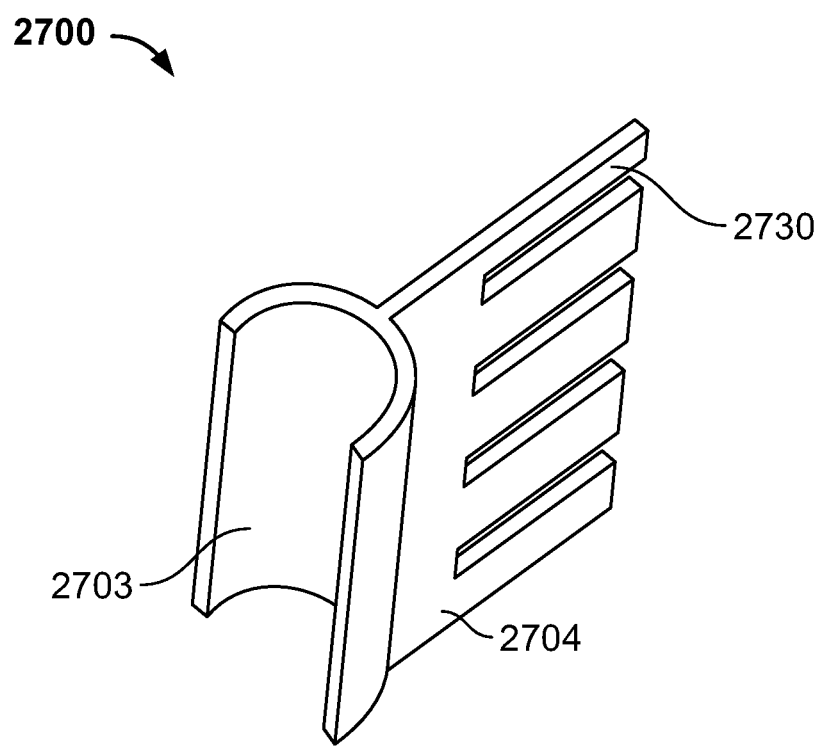
FIG. 49 is a perspective view of a saloon door bridge according to one embodiment of the disclosure.

FIGS. 48-49 illustrate embodiments of a saloon door bridge. In FIG. 48, bridge 2600 includes a clip 2603 extending from one end and a panel 2604 extending linearly and in a single plane from the clip. On one surface of the panel are teeth 2630. A distance of panel 2604 from the clip to its free end is less than an anticipated distance between rods in a retracted position in the body of a patient. Bridge 2700 shown in FIG. 49 is similar to bridge 2600 though instead of teeth, bridge 2700 includes a fork shaped extension 2730 from panel 2704. Each of these panel surfaces are configured to mate with a complementary surface on another saloon door bridge. Panel 2704 may extend from clip 2703 a distance less than that between fully retracted rods of a retraction system, but may also be longer than such distance.

Panel bridges may have a wide range of lengths, widths, thicknesses, and radii. In the context of lateral approaches to the spine, the length of the bridge (same direction as length of portal) may be between 1 mm and 80 mm. However, in the lateral approach and other applications, the length of the bridge can be as much as the length of the retractor rods. One exemplary bridge for placement adjacent to the psoas muscle has a length of 60 mm. In another example, the length of the bridge is the same as the length of the psoas muscle. The width of the bridge may range from about 6 mm to an entire perimeter of a surgical portal, i.e., where the bridge is a ring. A 6 mm width would be sufficient to extend beyond a 4 mm diameter rod and allow for the placement of two 1 mm wide LED lights thereon. A 20 mm width will typically span a distance between two retracted rods defining the portal perimeter. In an example where the bridge is a ring extending around a perimeter of the surgical portal created for the placement of a plate, the width of the bridge, i.e., around the perimeter of the portal, corresponds to the size of the portal opening, approximately 23 mm by 30 mm in dimensions. Typically for placement of spinal implants, a perimeter for the portal is somewhat smaller and may be 18 mm by 26 mm or 6 mm by 22 mm. In other spinal applications or applications outside of the spine, the dimensions of the opening may be much larger as required for the applicable procedure. As evident from the described embodiments, the bridge may be sized and positioned on a rod to protrude into the portal as little as 0 mm. Protrusion may increase by several millimeters where additional structures are added to the bridge, as described in greater detail below, or where a bridge thickness and/or clip is sized so that it protrudes into the portal. Although the radius of the bridges varies, to the extent there is a radius, a single engagement bridge configured to engage with one rod typically has a curved shape with a radius measuring 3 mm. The radius of the bridge is typically larger for bridges extending between two or more rods, and may be 100 mm in some cases.

The panel bridges can be varied in many ways. For example, the panel bridges may include a panel defined by a single radius or a varying radius. The panels may have a wave form shape or a flat shape. The panels may also be shaped with a series of flat surfaces adjacent to one another at angles in a direction of the width of the panel, i.e., measured in parallel with a perimeter of the surgical portal when in the portal. The panel bridge can also have a shape that is a portion of a round, oval, rectangular or square shape. In other examples, the bridge may have varying thickness along its width and/or its length. The bridge may be made up of multiple panels or may be monolithic. The overall width may be any portion of the portal perimeter, such as one quarter or one third of the perimeter. In some examples, as noted above, the bridge can encapsulate the entire perimeter of the portal and extend around it forming a ring. In this manner, the bridge may encapsulate any number of distracted rods, such as fix, six or more. In yet another example, the panel bridge may include a window therein on any given panel for placement of lighting or other accessories.

With regard to the angled panel portion, some variants of the bridge may include an angled panel portion longer or shorter relative to main panel portion than that shown in FIGS. 19-23. In some examples, the panel is formed from a main panel portion without an angled panel portion. In still others, angled panel portion may be toed out, extending away from the portal toward its lower edge at the leading end. In still further examples, angled panel portion may be curved or have another non-linear shape when measured over its length, the length being parallel to a rod when in position in the surgical portal. Also, more than one angled panel portion may be included. In others, any angled panel portion may be connected to main panel portion by a hinge or another similar connection that allows angled panel to rotate relative to main panel portion. This is described in greater detail below. Such rotating effect can be designed for manual activation via a switch or can be configured to occur automatically when main panel includes a ball detent mechanism, for example, that works with the rod so that it actuates when the bridge reaches a predetermined depth within the portal. When including such a feature, the panel bridge may have recessed surfaces or holes through its panels to accommodate the requisite accessories. Such variations in the panel bridge surface may also be included to incorporate other features, such as marking and Light Emitting Diode ("LED") lighting, the latter discussed in greater detail below. In other examples, the angled panel portion may include feet or teeth or may be complemented by a structure with feet or teeth attached to the bottom thereof. The feet or teeth can be designed for engagement with soft or hard tissue at a distal facing end of the bridge to minimize the possibility that the surgical portal will be compromised during surgery.

Figure 38:
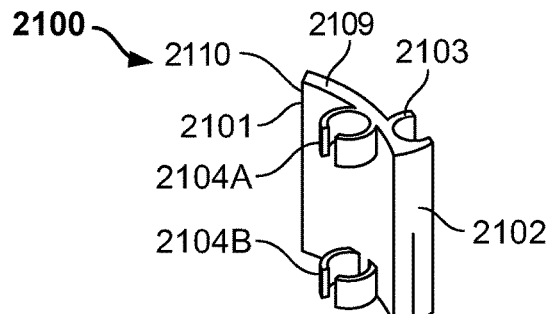
FIG. 38 is a perspective view of the use of an endoscope bridge according to one embodiment of the disclosure.
Figure 38:
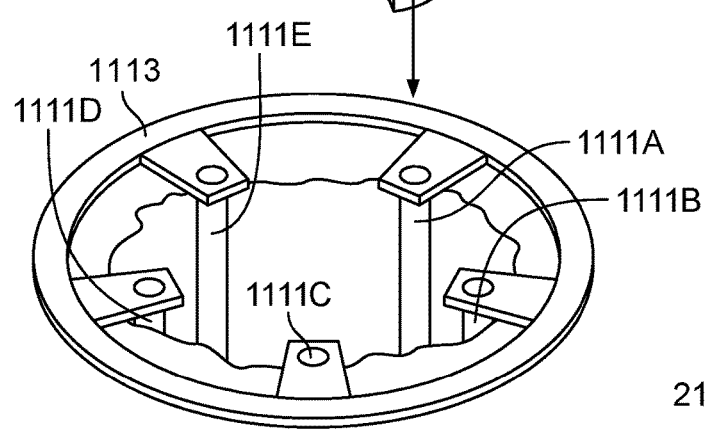

The clip may also be varied in many ways. For example, a bridge may have no clip so that the concave surface of the bridge is adapted to slide against retractor rods. In others, a bridge may have two or more clip structures, on either a portal facing or tissue facing side of the bridge. In another example, the portal facing side of the bridge may have a different number of bridges than the tissue facing side. The location of the clip on the panel in FIGS. 19-23 is merely exemplary and the clips can be placed at any location on the width of the bridge or relative to other clips, where two or more are included. Ultimately, the location of the clips is a matter of design choice. Of course, although the clip is shown as a C-shaped channel in FIGS. 18-23, the clip shape may be varied to accommodate any rod cross-sectional shape. In this manner, the clip may be any securement structure. For example, the securement structure can include a sequence of flat edges at angles with respect to one another extending from the bridge panel surface and forming a partial enclosure. In other examples, a dove tail connection, slidably engageable connection or ball detent mechanism can be used in place of a clip on the bridge. If applicable, two clips on a bridge may each have different shapes to accommodate different types of rods. This may be applicable if one rod is for retraction and the other for stability in the form of a fixation post. In still other examples, the clip may only extend over part of the bridge length. In some of these examples, two separate clips may be engageable with a single rod. One example of this is shown in FIG. 38, discussed in greater detail below. Further, in some examples, the clip may have a surface shaped to be larger than a rod to be disposed therein, providing a loose engagement with the rod. In this manner, such clips do not fully capture the rod. Rather, these clips are guided over the rod. Such guiding clips allow the bridge to self-adjust based on loads from adjacent tissue, similar to bridges with no clips, since the clip is not fixed relative to the bridge. This is in contrast to tightly conforming clips, which hold the bridge relative to the rod to maintain a predicable orientation of the bridge relative to the rod.

In yet another variant, the panel bridge may be a fabric mesh. The fabric can have strength and flexibility so that when subject to load, it can deflect an amount deemed small enough not to impede a physical space in the surgical portal while still allowing some tissue creep to place the fabric in tension. Put another way, the fabric mesh has a "tenting" effect when subject to loads. In one example, the fabric mesh extends between two rods and is engaged with each using any number of structures as contemplated throughout the disclosure. It is further contemplated that each of the above described variants and examples can be applied in combination.

In another variant, the panel bridge is elastomeric, made of a material such as rubber. The elastomeric panel bridge is sized to attach to a single rod or to span between two or more rods and also includes clips for attachment to any number of retractor rods. One example of the elastomeric panel bridge 4100 is shown attached to rods 4122-4124 of a retractor 4000 in FIG. 65 and includes a panel body 4102 with three clips 4112, 4114, 4116. Each clip is engageable with a respective rod. In some examples, the clips and the panel body are a single monolithic elastomeric structure. In other examples, the clips are separate elements that are attached to the panel body. In these instances, the clips may be elastomeric or may have other material properties as a matter of design choice. Adhesives or other connective structures as known to those of ordinary skill may be used to secure the clip to the panel body.

Figure 65:
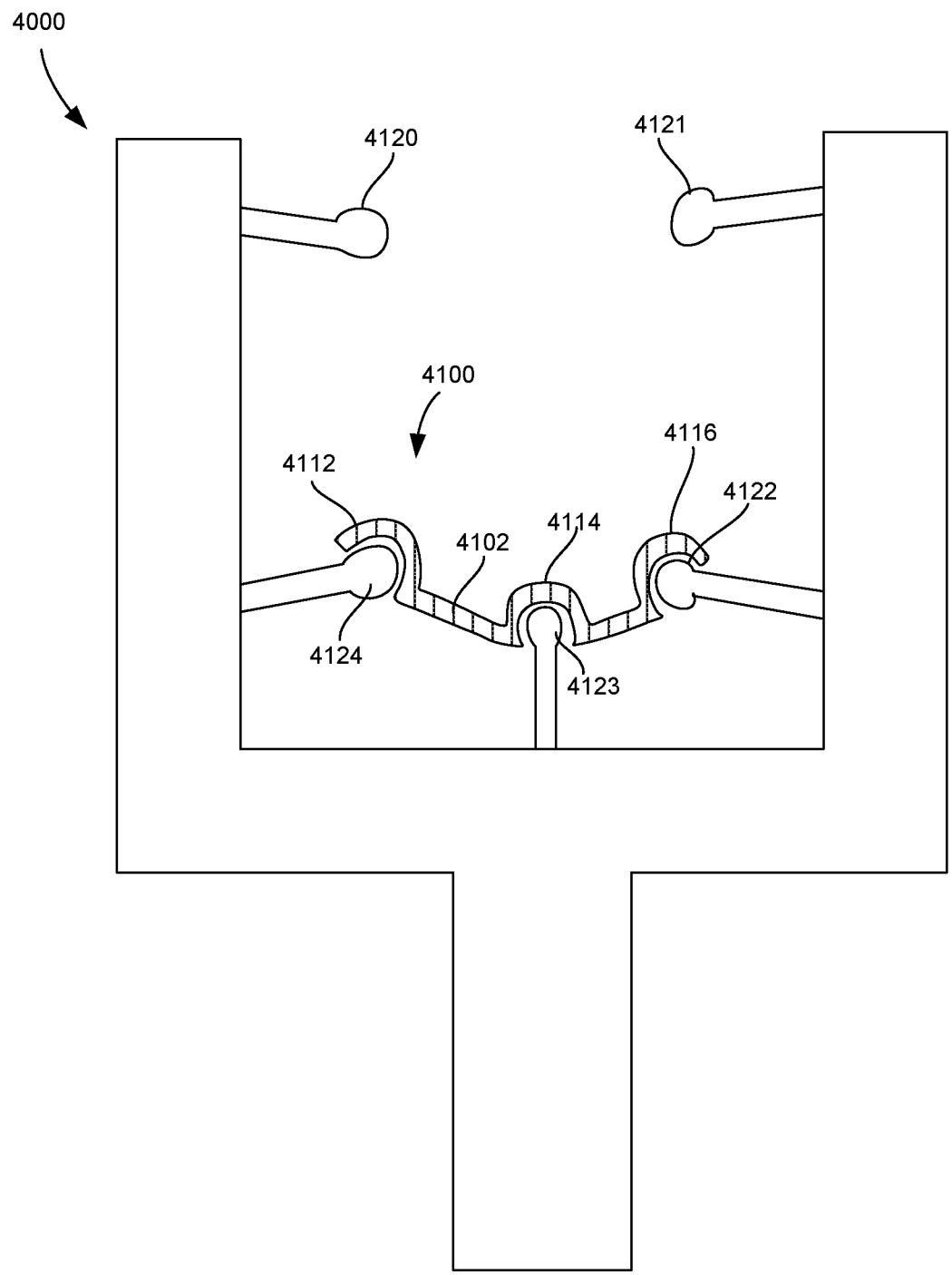
FIG. 65 is a top view of a retractor with an elastomeric bridge attached thereto according to one embodiment of the disclosure.

Because elastomeric panel bridge 4100 has elastomeric properties, clips 4112, 4114, 4116 are engageable to respective rods while the rods of a retractor, e.g., rods 4120-4124 of retractor 4000 shown in FIG. 65, are closed with respect to one another or while rods are retracted. Specifically, the properties of panel, and in some variants also the clips, allow the elastomeric panel bridge to deform to adapt to changes in spacing between the rods. In this manner, the elastomeric panel bridge is advantageous in that it can be engaged with one or more rods of a retractor at various stages in a surgical procedure and its engagement to the rods is preserved even when spacing between the rods changes. Moreover, the properties of the material, although exhibiting a certain degree of deformation when subject to loading, have sufficient load bearing capacity to retain tissue when in use. For the above reasons, the elastomeric panel bridge is sometimes referred to as a tissue fence.

The properties of the elastomeric panel bridge may also allow for light to travel therethrough, providing additional options to a surgeon for directing light into a surgical portal. In still further examples, the elastomeric panel bridge may also be modified to include attachments for lighting or, in some examples, cannulations or other adaptations for the placement of fiber optic cables therethrough.

Panel bridges may also have neuromonitoring elements which are built into panel bridges made of polymer. The use of polymer material for the bridge is advantageous in that it is a natural electrical insulator providing reliable insulation for a neuromonitoring element. Selection of a neuromonitoring element that is a good electrical conductor is desirable, therefore use of gold coated copper or aluminum or other similar materials represent some preferable options. The neuromonitoring element may be in the form of a single conductive surface on a tissue facing side of the bridge. In this configuration, the bridge is designed to neuromonitor in place of another element such as a rod. Neuromonitoring as an aspect of the procedures relevant here is discussed in greater detail in at least the '228 Publication.

In another aspect, panel bridges are employed in a method of maintaining the surgical portal size and also for providing further retraction of tissue. Although the embodiments herein are described in the context of lateral approaches to the spine, other approaches are also contemplated. These include, for example, anterior and posterior approaches. The choice of approach often depends on the type of implant being placed. For example, an anterior approach may be used for anterior lumbar interbody fusion implants. In addition to procedures involving the spine, the concepts described throughout the specification may also be employed outside of the spine.

In one embodiment, rods 1111A-E, in a closed position (not shown) and secured to retractor system 100, are inserted and advanced laterally through a previously created incision in the body of the patient toward a target site. To ensure accurate insertion, rods 1111A-E may be placed over a guidewire previously inserted to identify a path to the surgical site. Upon completion of advancement, rods 1111A-E are distracted to create a tissue portal 20, or path, to the surgical site, as shown in FIG. 18, for example. After the tissue portal is opened to a desired size, offset bridge 1200 is introduced to maintain portal 20 size. As shown in FIG. 19, clip 1203 of offset bridge 1200 is engaged with rod 1111A at a location outside of the body of the patient so that rod 1111B remains on the same side of concave surface 1210 as rod 1111A, e.g., as shown in FIG. 19. This represents one advantage of the method, as the bridge may be easily secured even prior to entering the portal. To ensure contact of bridge 1200 with both rods 1111A-B, bridge may be rotated about clip 1203. Bridge 1200 is then slid over rod 1111A to advance it into portal 20. During advancement, bridge 1200 pushes tissue obstructing the path of advancement and in at least this way further retracts tissue adjacent to the portal. The smooth low-friction convex surface 1209 improves the ability of bridge 1200 to do so. In the above steps, the bridge may be inserted and advanced manually by hand or with a tool adapted to hold the bridge. After bridge 1200 is advanced to a desired location in the portal, e.g., as shown in FIG. 20, further rotation of bridge is performed as necessary to align it with respect to rods, to ensure proper contact with rods (here, rods 1111A-B) and to prevent any undesired tissue creep. Additionally, rotation of the panel bridge ensures that it is in the position of lowest stress to minimize tissue damage and increase bridge performance while retaining tissue. When the panel bridge is attached to a rod, the bridge remains free to rotate, and thus can be rotated into a position of minimal stress on the adjacent tissue. In a variant, the bridge may be inserted from an interior facing side of the rod and then rotated into a desired position once the bridge is advanced to a desired depth within the portal. Surgery may then commence. Following completion of surgery, bridge is slid back out of portal 20 on the same path it entered and is removed by simply pulling it off the rod. In this manner, panel bridges with clips are releasably engagable with rods.

Panel bridges 1300, 1400 and 1500 are engaged and advanced in a manner similar to panel bridge 1200. However, considerations during adjustment of the bridges may be different due to differences in size and the number of securement structures, i.e., clips. For example, centered bridge 1400 need not be rotated to contact a second rod, as it is designed for engagement and contact with a single rod, and in some cases, additional rods. Use of bridge 1400 may be desirable where significant tissue creep into the portal has already occurred and damage to tissue would otherwise result if a bridge were inserted with a clip on an inside surface of the bridge. A slight difference in approach applies for dual engagement bridge 1500. Clips 1503A-B of dual engagement bridge 1500 are both engaged with respective rods 1111A-B prior to advancement into the portal, as shown generally in FIG. 23, but otherwise the method is as described for panel bridge 1200. With regard to bridges 2400, 2500 shown in FIGS. 46 and 47, placement into a surgical site is similar to that for Bridge 1500, though in many cases pressure is applied to adjacent rods as bridges 2400, 2500 are engaged, creating tension in the bridge panels, thereby limiting deflection when subject to loading.

Figure 50:
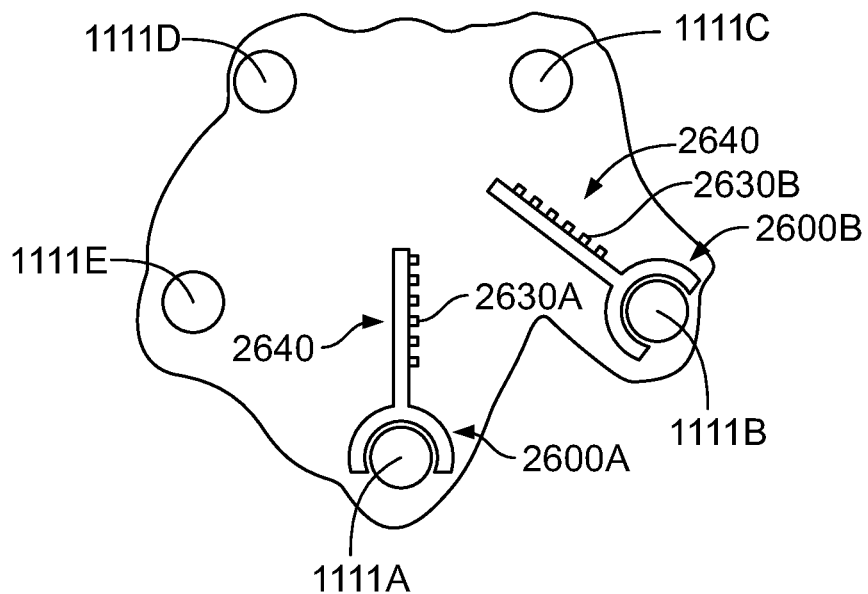
FIGS. 50-51 illustrate a top view showing a use of a pair of the bridge as shown in FIG. 48.
Figure 51:
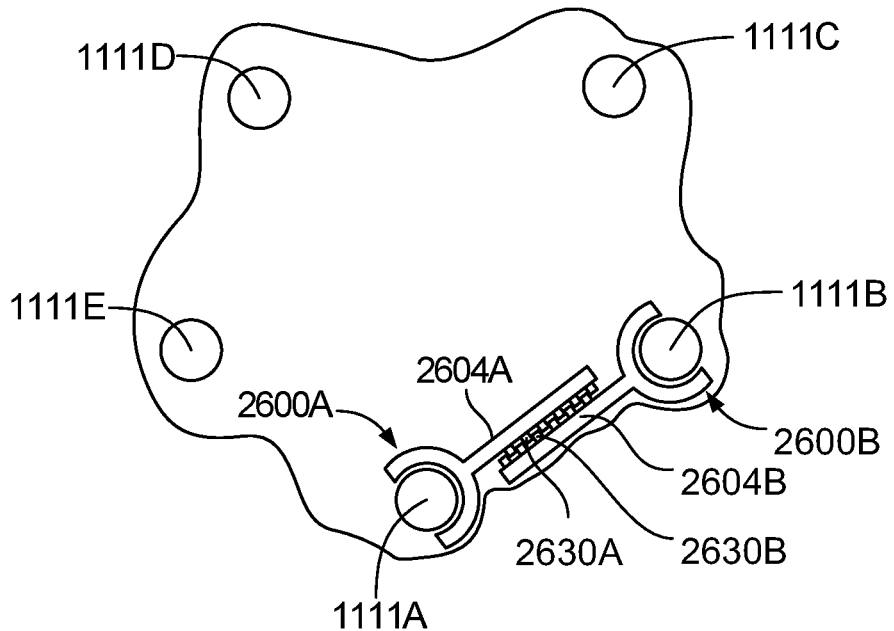

Saloon door bridge 2600 as shown in FIG. 48 is used in conjunction with at least one other bridge to retain tissue, as shown in FIGS. 50-51. Initially, two saloon door bridges 2600A, B are engaged to respective rods 1111A, B in a portal created by a retraction system with rods 1111A-E. Engagement and advancement of individual bridges 2600A, B is performed as with other panel bridges. Upon advancement to a desired position within the portal, each bridge 2600A, B is rotated toward one another as indicated by arrows 2640 in FIG. 50. Here, bridge 2600B is rotated ahead of bridge 2600A so that teeth 2630A, B of the respective bridges face one another. As each bridge is rotated, any tissue that has crept between rods 1111A and 1111B is pushed back by the panels of the respective bridges. When panels 2604A, 2604B approach one another, the teeth of the respective bridges engage to hold the bridge in a secure position, while also retaining any nearby tissue behind the respective bridges, as shown in FIG. 51. This method is similarly performed for the saloon door bridge shown in FIG. 49, where the forks 2630 of respective bridges engage one another as each bridge is rotated toward the other. Due to the shape of the forks, the panels of such bridges are not be parallel with one another when the forks are engaged, but still provide a secure connection to retain tissue.

Elastomeric panel bridge 4100 shown in FIG. 65 may be engaged onto one or more rods and then advanced into a surgical portal in a manner similar to panel bridge 1200. Typically, where a panel bridge such as panel bridge 1200 includes two or more clips, such engagement and advancement will be performed once the rods are retracted so that tissue may be retained while surgery is performed. With elastomeric panel bridge 4100, the bridge may be inserted after the rods are retracted or before they are retracted. If bridge 4100 is engaged and advanced before retraction, it will maintain its securement to the rods through clips 4112, 4114, 4116 while the rods retract as the panel 4102 deforms to adjust to the change in spacing between the rods. Meanwhile, the panel 4102 of the bridge will continue to retain tissue to prevent tissue creep and to maintain visibility into the surgical portal. In instances where the panel bridge 4100 is inserted before retraction, it may be engaged to one or more rods before the retractor is positioned over the patient for use or at any time thereafter during a surgical procedure.

In other variations of a surgical method, lighting may be directed through the elastomeric panel bridge 4100 to the target site or fiber optic cables may be inserted through a cannulation in the bridge to direct light into the surgical portal. This may be done at any step of a surgical procedure provided the elastomeric panel bridge 4100 is in place engaged to one or more rods of the retractor.

The method of advancing the panel bridge structure may be varied in many ways. In one variant, a panel bridge may be advanced with a rod separate from the retractor assembly without engaging with the rods of the retractor assembly. In this approach, the rod with bridge engaged thereon is advanced into the portal at a desired location typically between rods of the retractor assembly. Such rods may be held in place by placing the bridge behind a rod of the retractor assembly inside the portal while the new rod is secured to a clip of the bridge. Further securement of the rod may be achieved where the rod includes a pointed tip and the rod functions as a fixation post. In this example, the rod is securable to a surface at the bottom of the portal, such as a vertebral body or an intervertebral disc space. Additionally, in another example, the bridges used may be of a size so that more than one bridge is engaged and advanced over a single rod. Of course, this approach has greater practical application where the bridges used are shorter in length. In a particular variant of the method, the bridges may be advanced into the portal when engaged to a rod or rods through the use of an insertion tool. The variants and additional examples described above may operate in combination with each other and/or with the embodiments above. In this manner, a wide variety of approaches to bridge placement is envisioned. In another example, where the bridges are in the form of rings forming a perimeter around the portal, the ring can be advanced in between rods of a retractor where the rods are toed in to remove or decrease the toe-in or to create a toe-out for a portal when advanced to a distal end of the portal. In this manner, the rings maybe similar to those described in the application entitled "Expanders for Rod Retraction," filed concurrently herewith, which are also contemplated as being used with the structures and methods described in the embodiments of the present disclosure.

Lighting with Bridges and Other Structures in Portal

In another aspect, the present disclosure relates to bridge structures with lighting. Such structures provide many of the benefits of panel bridge structures as described herein, and also provide in situ lighting for surgical portals in a portable and minimally intrusive manner.

Lighting for the bridge structures of these embodiments can be any known lighting such as fiber optic lighting, LEDs, or lighting technologies developed by Lumitex®, Inc. When used, LED lights may include lights with a wide range of color temperatures. Furthermore, LED lights may be configured to have adjustable color temperature. This provides surgeons with the option to tailor the color of light directed to the surgical site. For example, a yellow, lower color temperature may be desirable or conversely a blue, higher color temperature may be desired. In many instances, a surgeon may wish to adjust lighting to correspond to the lighting in the room where the surgery is taking place. In some of those instances and in others, lighting may be adjusted to emphasize certain tissue within the surgical portal or to even the lighting within the portal. Adjustment may be desirable based on individual preferences and/or the condition of the patient undergoing surgery. Adjustable color temperature is realized in a number of ways. For example, multiple LEDs on a bridge or a series of bridges advanced into the surgical portal can be individually controlled so that the LEDs may be selectively activated or deactivated. By activating particular combinations of LEDs within a group of LEDs, the color temperature of the light within the portal can be tailored as desired. To provide a wide range of potential color temperatures, the group of LEDs may include individual LEDs covering a wide variety of color temperatures. For example, two bridges may be inserted into the surgical portal, each having five LEDs, where the first bridge includes two red and three yellow LEDs, while the second bridge includes three white and two blue LEDs. Individual LEDs can be at least as small as 1 mm in diameter, allowing for placement through and on a variety of locations in the various embodiments of bridges described throughout this disclosure.

Beyond individual LEDs, red blue and green ("RGB") LEDs can be used alone or in combination with individual LEDs. Because RGB LEDs include individually adjustable red, green, and blue light, such LEDs can similarly be incorporated into bridges and be adjusted to change color temperature. The color of RGB LEDs is adjustable using accompanying switches. To illustrate how a desired color is obtained with an RGB LED, one example involves production of a white light by applying low current, i.e., 10 mA, to each of the red, blue and green LEDs. In another example, production of a blue light involves applying a 10 mA current to the red LED and a 60 mA current to the blue and green LEDs. The change in current changes the wavelength value of the LED light, thus changing the perception of the light itself when viewed within the surgical portal.

Individual LEDs and RGB LEDs are also configured so that brightness is adjustable. For example, if a color temperature chosen during surgery is 3000 Kelvin, the brightness in lumens can be adjusted for that color temperature, for example, from 1000 lumens to 1200 lumens. One type of structure contemplated to provide adjustable brightness of LEDs involves the use of a potentiometer and resistors. In particular, each LED is accompanied by an LED battery switch, fixed position resistors, resistive circuits and a potentiometer. The potentiometer provides a means for a user to adjust the resistance in the circuit, thus controlling the brightness of the LED. One example of such a structure is a series potentiometer with a resistance range between 0-1000 k Ohms. The series potentiometer is specified for operation at 2.95-3.0 Volts and is powered by a 3V CR2 Lithium-ion battery. The potentiometer or an adjustable selection of fixed resistors are connected in series with the LED and battery to limit current to the LED. In other examples, one of ordinary skill will appreciate that other methods to control resistance to the current or even voltage may be used to control brightness of the LEDs. LEDs with adjustable brightness allow lighting to be used in a manner that can dramatically increase the lifespan of the LEDs. In one example, LEDs with adjustable brightness may continue to emit light over a period of days.

The use of LEDs for lighting is advantageous in that it provides a cooler light with less heat than traditional forms of light. Further, because the lighting is positioned very close to the surgical site, it is highly efficient. Moreover, LEDs use less power for the same output when compared to other forms of lighting. It is contemplated that the above described features of LED lights can be applied to all embodiments involving lighting as described herein.

In one embodiment, lighting bridge 1600 includes a concave surface 1610A-C, a convex surface 1609, a lighting portal 1604, two storage volumes 1613A-B, a plurality of cover plates 1611A-C, and a plurality of mounting holes 1612A-D. Bridge 1600 is designed so that concave surface 1610A-C is a portal facing surface and convex surface 1609 is a tissue facing surface.

Figure 24:
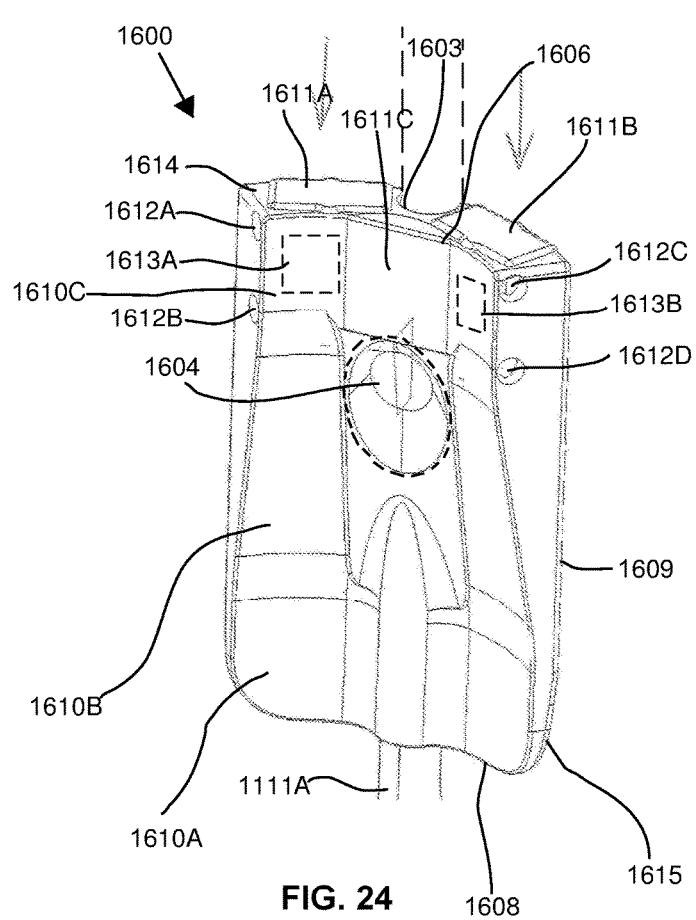
FIG. 24 is a perspective view of a lighting bridge according to one embodiment of the disclosure.

Concave surface 1610 has a length between a top end 1606 and a bottom end 1608 designed to provide a working boundary within the portal. The concave surface includes three portions, an upper portion 1610C, a tapered portion 1610B and a lower portion 1610A, as shown in FIG. 24 and is made of a reflective material to maximize light projected into a surgical site when in use. As will be described in greater detail below, a principal function of tapered surface 1610B is the direction of light to a surgical site in the portal. In a central area of tapered portion 1610B of the concave surface is a lighting portal 1604 designed for the engagement and mounting of a lighting fixture therein, such as an LED (not shown) with properties as described above.

Convex surface 1609 is a smooth surface with a length between top end 1606 and bottom end 1608. As with the portal bridges, and as is a common design feature among the bridges described in this disclosure, convex surface 1609, as the tissue facing surface, is a smooth, low friction surface, and is low friction relative to concave surface 1610A-C. In this manner, convex surface 1609 is designed to prevent tissue creep while minimizing soft tissue damage during advancement and while positioned within the surgical portal in the patient body, among other advantages. Convex surface 1609 also includes a groove 1603 that extends throughout the length of lighting bridge 1600. The recess is sized for engagement of a rod for a retractor assembly thereto and includes features to ensure such engagement is secure, such as a friction promoting surface. Groove 1603 is sized and positioned in bridge 1600 to minimize an overall depth of bridge between the concave and convex surfaces. This ensures the least amount of physical space consumed by the bridge in the portal. Convex surface 1609 is also configured to include a switching structure configured to activate upon contact with an object, such as a rod of a retraction assembly. In one example, the switch may be a button on groove 1603 that is pushed down by a rod as it passes over it, turning the light on due to interconnection of the button with a lighting feature. The light toggles back off when rod is removed and the button returns to its original position.

Towards a lower extent of bridge 1600, convex surface 1609 includes a tapered portion 1615 to ease advancement of bridge 1600 into portal, as with the above-discussed panel bridges. In the depicted embodiment, the taper has a "toe-in" effect, making the portal smaller at the base (i.e., at lower end 1608) of lighting bridge 1600.

As shown in FIG. 24, lighting bridge includes mounting holes 1612A-D on sides of the bridge between concave and convex surfaces 1610C, 1609. These mounting surfaces are designed for securement of lighting accessories or even for securement of light emitting devices, such as LEDs, depending on the particular circumstances of the surgical procedure at issue. Storage volumes 1613A-B encompass the internal space between upper portion 1610C of the concave surface and convex surface 1609 and are in communication with lighting portal 1604. Lighting portal 1604 is shaped so that a light, e.g., an LED, is disposable thereon. The LED may be mounted onto the portal in one of a variety of ways so that light from the LED is directed in a desired direction. Storage volumes 1613A-B are cavities that provide space for power cells, i.e., batteries, electrical power connections, e.g., wiring, and other components necessary for lighting so as to eliminate the need for wiring extending outside of the portal when the bridge is disposed therein. The power cell and wiring are further interconnected with the aforementioned switch to toggle the lighting element (not shown). In this manner, all components for lighting, including, notably, the power source, are fully integrated with the bridge structure. Cover plates 1611A-C enclose storage volumes 1613A-B to keep the electrical components powering the light source from extending outside of storage volumes 1613A-B. Cover plate 1611C is on upper portion 1610C of concave surface and cover plates 1611A-B are located on a top surface 1614 of lighting bridge 1600. Although it is envisioned that storage volumes 1613A-B minimize the space consumed by the electrical lighting components, it is contemplated that some wires may extend outside of lighting bridge 1600 without compromising the utility and effectiveness of the lighting bridge.

Figure 25:
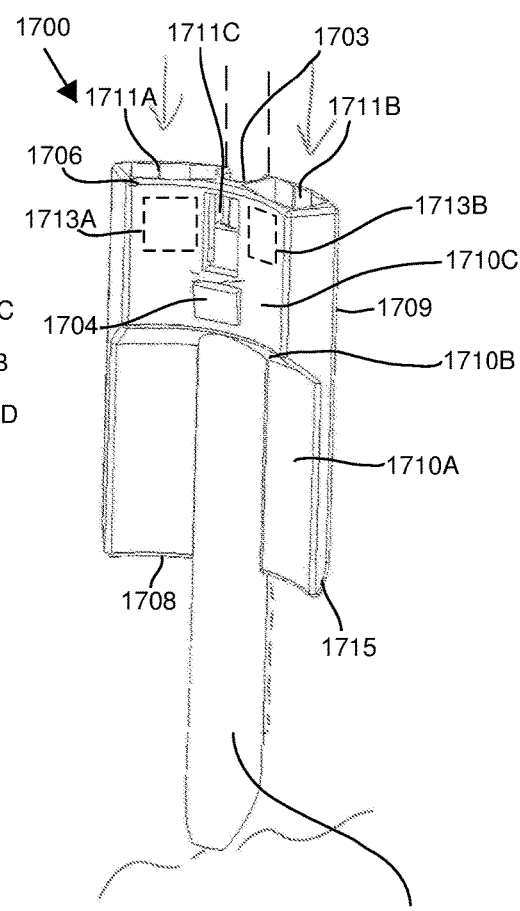
FIG. 25 is a perspective view of a lighting bridge according to another embodiment of the disclosure.

In another embodiment of a lighting bridge, shown in FIG. 25, lighting bridge 1700 is modified to include a fixation post 1721. The structure of lighting bridge 1700 is similar to that of lighting bridge 1600 and like reference numerals refer to like elements. Lighting bridge 1700 includes a concave surface 1710A-C, a convex surface 1709, a plurality of openings for cover plates 1711A-C, a mounting element 1704, and two storage volumes 1713A-B. Concave surface has several sections including a lower portion 1710A, an angled portion 1710B and an upper portion 1710C. Mounting location 1704 is located on upper portion 1710C, and is shaped and structured so that a light emitting device, such as an LED, is mountable thereon (not shown). As with lighting bridge 1600, storage volumes are in the upper portion of bridge 1700, as shown on FIG. 25. Angled portion 1710B functions similarly to tapered portion 1610B and directs light to an intended location such as a surgical site. Extending from immediately below mounting element 1704 in a downward direction beyond a lower end 1708 of a body of lighting bridge 1700 is fixation post 1721. Fixation post 1721 is designed to engage with a surface proximal to the surgical site, such as an intervertebral disc, when the bridge is in its intended location during surgery. Similar purpose fixation posts are discussed as separate elements in the '228 Publication.

Lighting bridges 1600, 1700 are preferably made out of a polymer material such as polycarbonate or PEEK in order to maintain radiolucency and flexibility while reducing neural and tissue stress. Alternatively, bridges 1600, 1700 may be a rigid material such as polycarbonate for the recessed surface intended for engagement with rods and polypropylene for the remainder, the polypropylene providing flexibility which is advantageous when tissue retraction is desired. In yet another alternative, lighting bridges 1600, 1700 as described are made of metallic materials for structural support and may include polycarbonate or similar light transmitting material to enhance the effects of lighting. Other considerations for the material of the lighting bridges are similar to those described for the panel bridge embodiments. In a variant, the materials and/or surface finishes of one or more lighting bridges or panel bridges may be one of the materials and surface finishes or a combination of the materials and surface finishes described for the ring structures in the '228 Publication.

Figure 52:
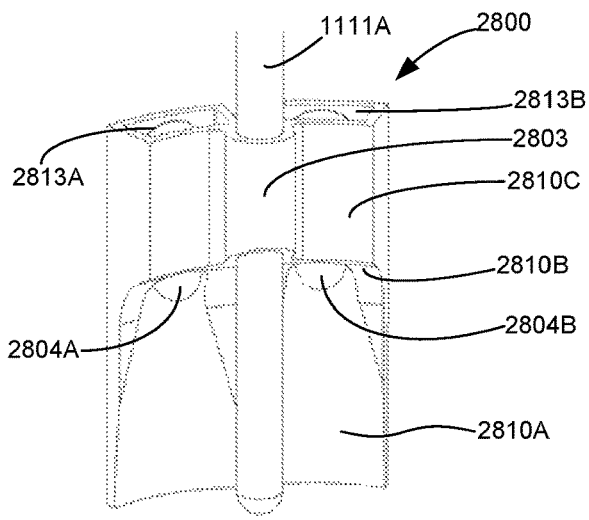
FIG. 52 is a perspective view of a lighting bridge according to one embodiment of the disclosure.
Figure 53:
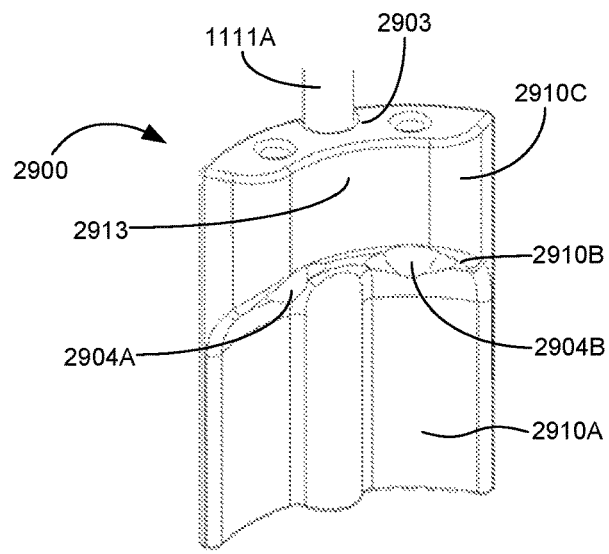
FIG. 53 is a perspective view of a lighting bridge according to another embodiment of the disclosure.

Additional lighting bridge embodiments are illustrated in FIGS. 52-57. These lighting bridges are similar to those shown in FIGS. 24-25, and like reference numerals refer to like elements. To the extent features of these bridges are not explicitly described, their characteristics may be as described for the previously mentioned lighting bridge embodiments. FIG. 52 shows a lighting bridge 2800 structured to accommodate two LEDs 2804A, B, one on each side of clip 2803, which is centered on the bridge. Each LED mounting location is located directly below a respective storage cavity 2813A, B for placement of a battery and other wiring therein, so that that the lighting is powered without external wire connections. LEDs 2804A, B are mounted on a downward facing surface 2810B of the bridge, protruding from a lower surface 2810A below, so that light is directed toward a target below the bridge and is not impeded by the structure of the bridge. Clip 2803 extends inward relative to the storage volumes so that when inserted over rod 1111A, the body of bridge 2800 is behind the radius of the portal near the rod. This ensures protrusion of the bridge into the portal is minimized. FIG. 53 also shows a two-LED lighting bridge 2900, with LEDs 2904A, B, one on each side of groove 2903. In this design, groove 2903 is set back from a concave surface 2910C of the bridge body so that at least some of the bridge extends into the portal. Such a configuration may be advantageous where it is difficult to retract tissue immediately behind a rod.

Figure 54:
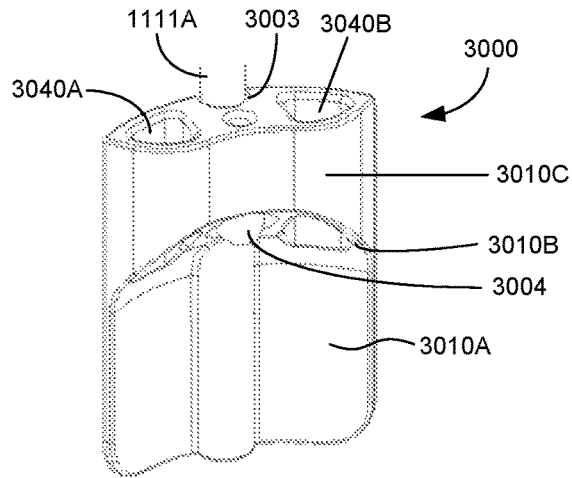
FIG. 54 is a perspective view of a lighting bridge according to another embodiment of the disclosure.

In FIG. 54, a bridge 3000 is shown that includes two viewing portals 3040A, B symmetrically positioned about a groove 3003 sized for rod 1111A. An LED 3004 is mounted on a downward facing surface 3010B near the center of the bridge between the viewing portals. Here, although the bridge protrudes at least minimally into the portal, viewing portals 3040A, B provide additional visibility toward a distal end of the portal. Additionally, the viewing portals may be used to advance equipment used during surgery.

Figure 55:
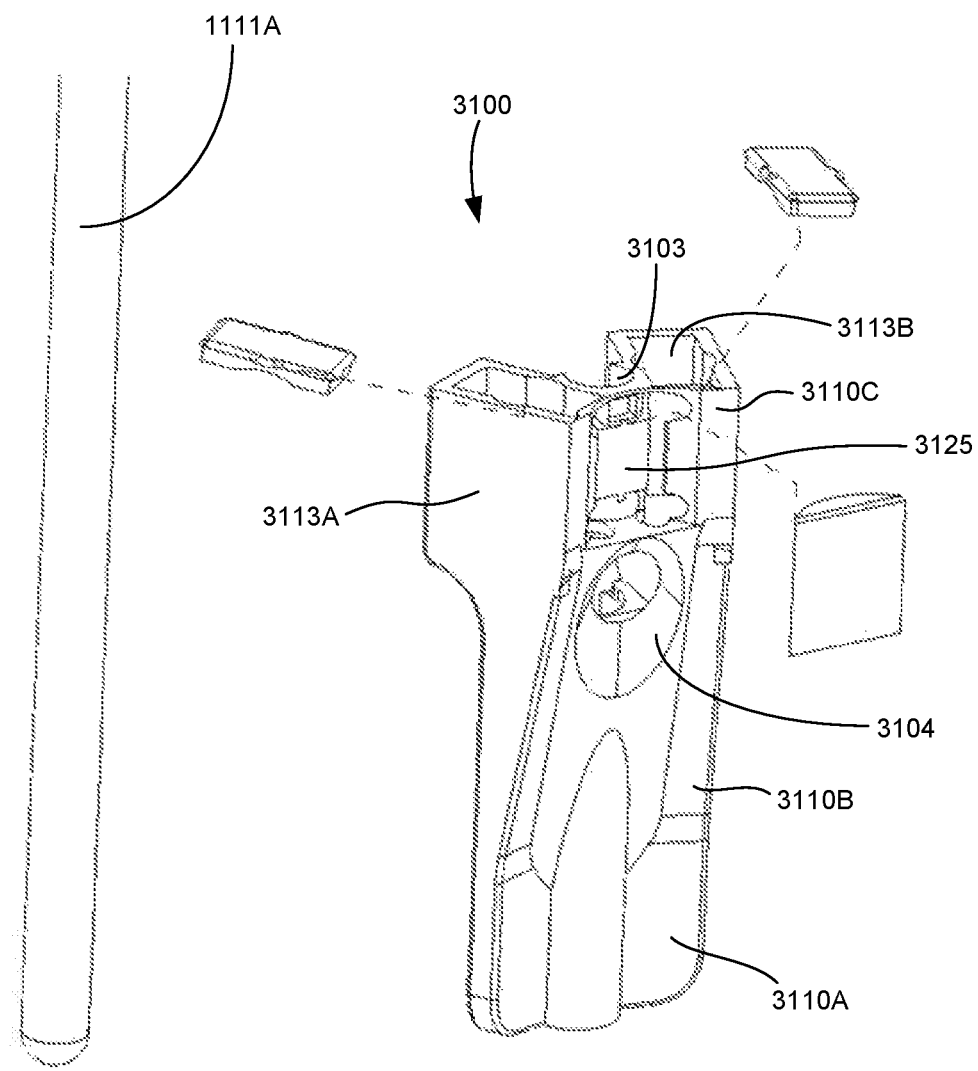
FIG. 55 is a perspective view of a lighting bridge according to yet another embodiment of the disclosure.

FIG. 55 illustrates another embodiment similar to the lighting bridge of FIG. 23. Here, lighting bridge 3100 includes storage volumes 3113A, B for placement of batteries and a third volume 3125 in between the storage volumes and a mounting portal 3104 for wiring, switches or other equipment and accessories needed to operate a self-sustaining lighting system for the bridge, with an LED or other light mounted at mounting portal 3104. A length of lighting bridge 3100 may be sufficient so that narrower portions corresponding to surfaces 3110A, 3110B traverse an entire portal depth. In this manner, intrusion of the bridge into the portal or the tissue behind the portal may be minimized as the upper structure corresponding to storage volumes 3113A, B may remain outside of the portal during use of the bridge. A length of lower portion 3110A may vary to accommodate varying portal depths as desired to keep the larger upper structure outside of the portal.

FIGS. 56 and 57 show two embodiments of a particularly narrow lighting bridge 3200, 3300. Bridge 3200 includes groove 3203 for placement of a rod 1111A therein, and includes a structure that extends in an inward direction from groove 3203 via upper surface 3210C. A single LED 3204 is mounted on downward facing surface 3210B. Light generated by LED 3204 is unimpeded by lower surface 3210A. This bridge provides lighting in a minimally intrusive manner by only occupying a small fraction of the portal cross section when placed over a rod. Lighting bridge 3300 includes a clip 3303 with an outer surface running parallel to a rod 1111A disposed in the clip, thus minimizing intrusion into the portal. LEDs are mountable adjacent to the clip on each side of it on intermediate surface 3310B at mounting locations 3304A, 3304B, facing an open space below unimpeded by lower surface 3310A. Where rod 1111A is 4 mm in diameter, a width of bridge 3300 may be as narrow as 6 mm, with 1 mm on each side of clip 3303 to accommodate placement of LEDs.

Considerations for the size of the lighting bridge are largely as described for the panel bridge embodiments. In one example, the lighting bridge depicted in FIG. 24 has a length of 60 mm. For lighting bridges in particular, a length of the bridge typically falls within a range between 20 and 80 mm, although may be much greater. A lighting bridge may have a width as small as 6 mm to accommodate an LED on each side of a rod when engaged thereto, and may be as wide as space around a portal perimeter permits. A thickness of the lighting bridge may be such that the bridge protrudes into the surgical portal between 0-5 mm or more where the bridge includes accessory equipment therein, such as lights or an endoscope. In the other direction, the bridge may protrude into the soft tissue adjacent to the portal between 0-10 mm to accommodate a cavity in the bridge holding batteries, other similar accessories, or lighting components. Each of the above protrusion ranges is measured from a rod edge. The radii of the lighting bridge may vary in the same manner as with portal bridges. To the extent certain dimensions are not described for the lighting bridge, dimensions may be as described for other bridges in the disclosure.

The lighting bridge may be varied in many ways. For example, the lighting bridge may be any number of shapes or include any variety of components as described for other bridge structures throughout this disclosure. In some examples, lighting may be placed on or within any number of lighting portals or mounting elements to allow for the use of multiple light sources. For example, the lighting bridge may include four light sources, each equidistant from the center curved groove. Of course, such variants would be accommodated by varying shapes and quantities of lighting portals and/or mounting elements. The lighting portals or mounting elements may be aimed in a variety of directions to customize a focus of the light as desired for a particular type of surgical application. These possibilities also necessarily contemplate having light placed at particular locations and/or from smaller areas on the portal facing surface. For example, one LED may be placed on each side of a groove through a center of a bridge, with each LED pointed toward a common point below the bridge.

The lighting bridge may be made up of any number of materials, including transparent materials that conduct light through fiber optic light conduction. In this way, an overall effect of light transmitted from the light bridge is enhanced. The lighting bridge may be constructed with cost-efficient materials to allow for its use as a disposable and single use bridge.

In another embodiment, lighting is provided in situ at the surgical site using bridges other than lighting bridges and other structures placed in the surgical portal. For example, lighting may be placed on panel bridges, rods and structures tailored to hold an LED, as shown in FIGS. 26-29. The exact location and quantity of the lights is not limited by any consideration other than practical limitations during surgery. Lighting can also be internal to the bridge structure, so that an entire bridge can illuminate light. This type of lighting is enhanced when the bridge is made of a clear material. Provided that the size of the bridge is sufficient, such a variant is possible for any of the bridges described herein.

Power for the lighting can be portable and included with the lighting on the object it is disposed on or it can be supplied from outside the portal, as described in greater detail below. The lighting is designed to activate in a variety of ways ranging from manual to automatic.

Figure 26:
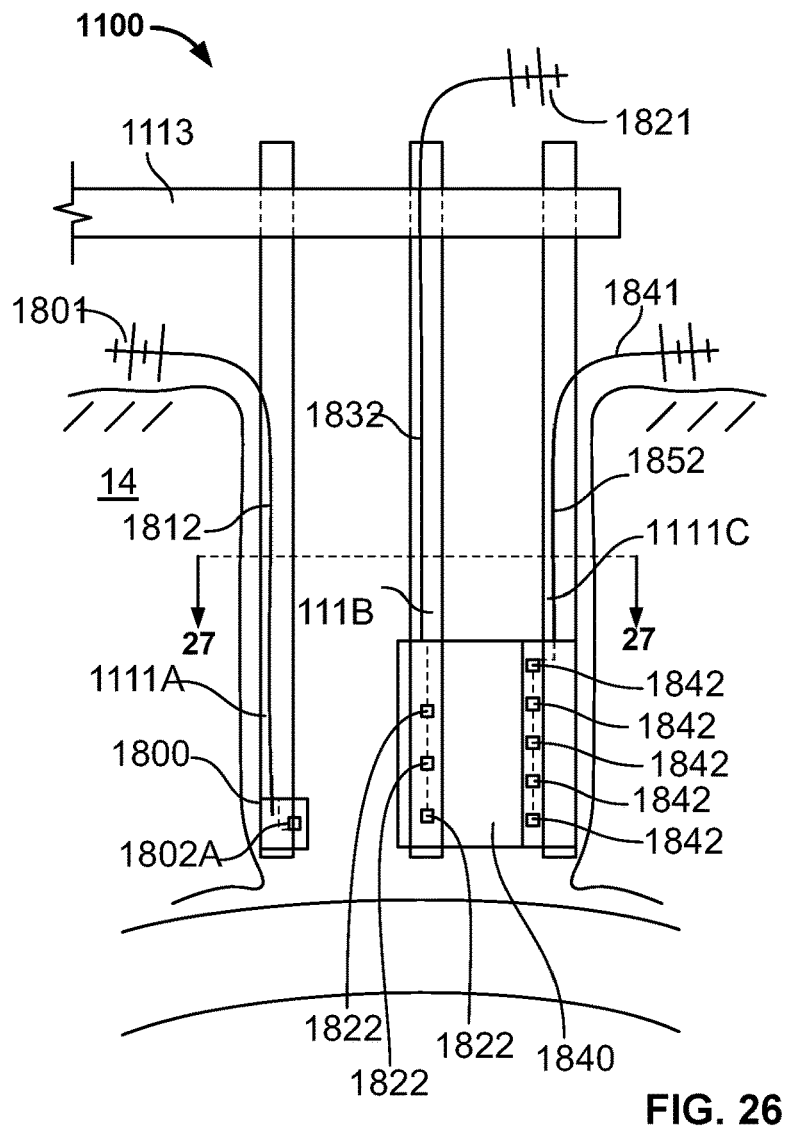
FIGS. 26-27 are side and section views, respectively, of lighting according to one embodiment of the disclosure as applied to bridges and rods.
Figure 27:
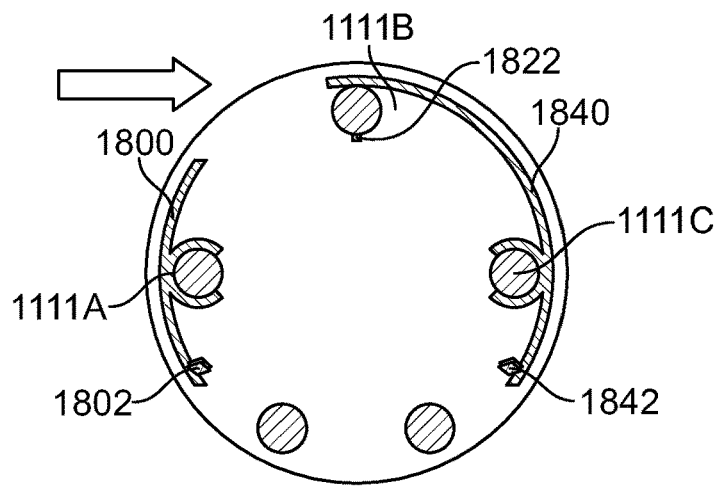

The lighting and its associated features permit its placement on a variety of surfaces and objects present during surgery. FIGS. 26-29 show some of the ways the lighting of this embodiment can be placed in situ within the surgical portal. In FIGS. 26 and 27, panel bridges 1800, 1840 both include LED lighting 1802, 1842, respectively. Panel bridge 1800 is of a much shorter length than bridge 1840, and only includes one LED while bridge 1840 includes five, as best shown in FIG. 26. The LEDs are mounted on a portal facing or concave surface of the bridges to direct light into the portal and to minimize any potential for damage to tissue. As depicted, the LEDs are supplied with power via wire 1812, 1852 extending out of the portal to a battery 1801, 1841, respectively. Structure for securement of the LEDs to the bridges and the wire used to carry power are a matter of design choice. For example, the LEDs may be attached to the bridges by adhesive tape, glue, or magnetic means. The LEDs can also be attached to the bridges with a clipping mechanism. Another way lighting is used is by securement onto a rod of a retractor. Three LEDs 1822 are secured onto rod 1111B as shown in FIGS. 26-27 to provide lighting in the portal. As with the panel bridge lighting, power is supplied from an external source 1821. Each of these forms of lighting enable visualization of the surgical site. Lighting may be toggled in a number of ways described in greater detail below. The number of LEDs for a bridge or rod as shown in FIGS. 26 and 27 is merely exemplary and may vary as a matter of design choice.

Figures 28, 29:
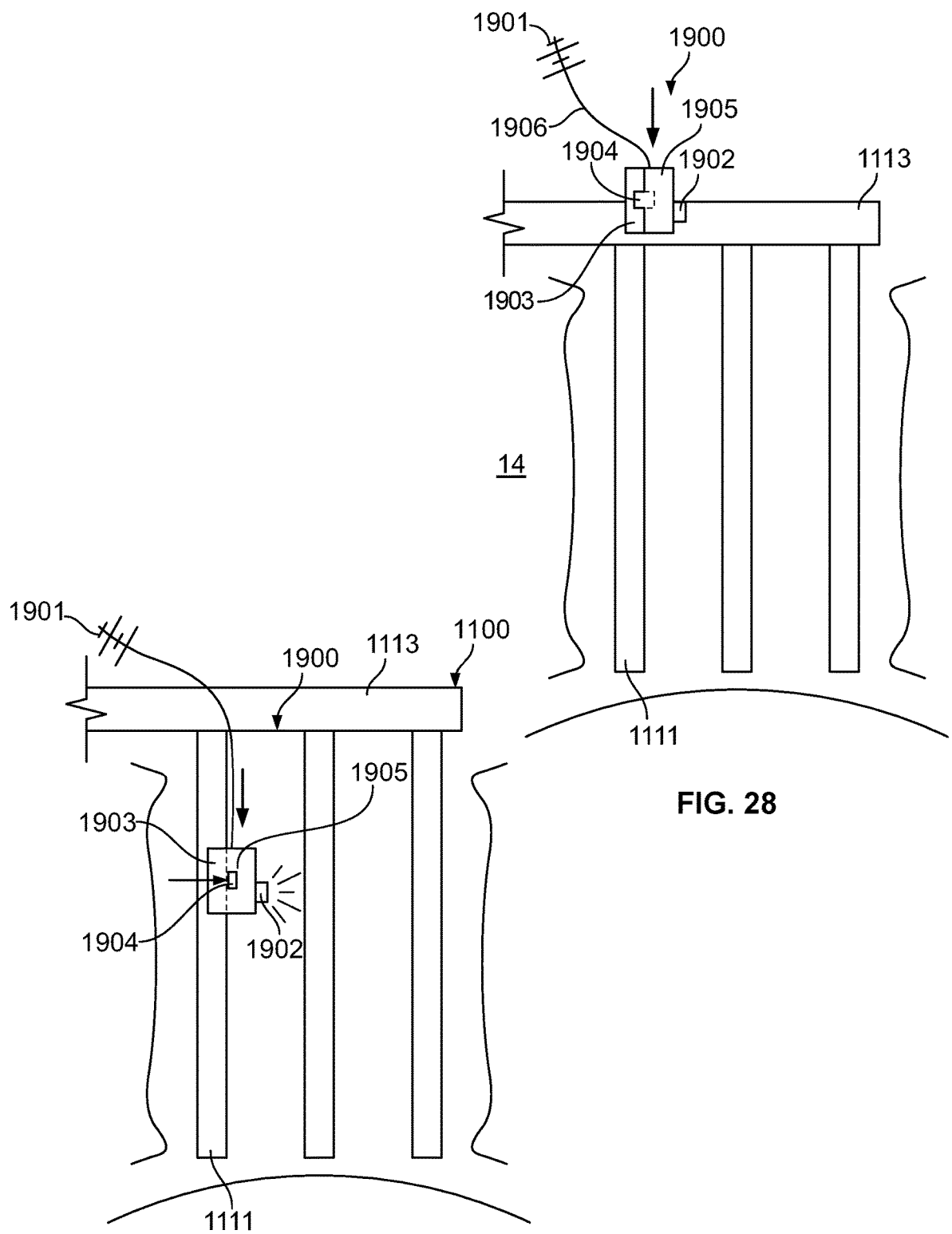
FIGS. 28-29 are side views depicting methods of employing a lighting device according to one embodiment of the disclosure.

In another embodiment, lighting is placed on a tailored light activation structure, such as lighting device 1900. As shown in FIGS. 28-29, lighting device 1900 is designed to illuminate automatically upon contact with a solid surface, such as a rod of a retractor assembly. The side profile of lighting device 1900 can be seen in FIG. 28 before lighting device 1900 is active and FIG. 29 shows lighting device 1900 after activation. As shown, lighting device 1900 includes an external battery 1901, wire 1906, clip 1903, switch 1904, and light 1902. Switch 1904 is a button disposed within clip 1903. Upon engagement of lighting device 1900 with an object, such as a rod, the button is depressed which forms the necessary electrical connection to toggle light 1902 into the on position. In this manner, activation of lighting is automatic with engagement of the holder with a rod during surgery. This is advantageous in that it simplifies and streamlines surgery.

The lighting may be varied in a number of ways. For example, lighting may be toggled on an off using a number of mechanisms. In addition to a switch on a groove or clip as described above which provides one form of automatic lighting, a photocell circuit can also be integrated with the bridge to provide automatic lighting toggled by whether a photo-resistor detects light. This circuit includes an LED, battery, resistors, transistor and photo-resistor. When light is detected, the light is off. However, when light is blocked from the photo-resistor, light is emitted. The circuit is designed so that photo-resistor resistance drops to a very low value when the photo-resistor is exposed to light and conversely the resistance dramatically increases when it is exposed to darkness. This configuration may be employed with only the LED and photo-cell placed into the portal, with remaining components such as the battery being positioned outside of the portal. Additionally, a potentiometer may be used in lieu of a set-value resistor to allow for the adjustment of light intensity and time duration of the light source based on the light input detected by the photoresistor.

Manual structures for toggling lighting include an electrical barrier in the form of a tab attached to the bridge. Until the barrier is removed, the light remains off. Once it is removed, the light turns on and remains on until its power source depletes. This manner of lighting is disposable and single use, and is advantageous in that no wire is needed to connect to a battery supply. Other forms of manual toggling of lighting include traditional switches requiring user actuation. Such mechanisms may be built into the bridge or may be located at the end of the wire so that lighting can be activated from outside of the surgical portal. In other examples, the lighting component for a bridge can be modified to include two LEDs on a single circuit. This provides better light intensity although it consumes more power from a power source. Each of the above mechanisms provides structure to provide lighting while minimizing the space needed outside of the surgical portal to facilitate such lighting. To the extent wiring is needed between a bridge in a surgical portal and an external location, it is small and minimally intrusive. Another advantage of these approaches is that battery power removes the risk of electrical shock with wall outlets.

In addition to color temperature and brightness, lighting may also be modified to include UV lighting. Such UV lighting may also be incorporated in a manner so that it can be modified during use of the bridge. In other variants, a conductive material may be used for the bridge when lighting is incorporated into the bridge. In this way, the small amount of heat generated by the LED will be drawn away from the bridge when in use because the rod acts as a heat sink and draws away heat. Lighting may further be modified for particular purposes. For example, the components for the lighting may be modified so that the LED begins emitting a blue light if the battery starts to deplete. Additionally or alternatively, the light may vary depending on its proximity to a nerve structure as detected by a neuromonitoring device. Further, the light may be flashed on and off in any manner. For instance, the light may be configured to activate and deactivate in rapid succession for two repetitions if the battery is almost depleted.

In another aspect, methods of directing light within a surgical portal are contemplated. In one embodiment, lighting bridge 1600 is employed in a method of maintaining the portal size while providing lighting to a surgical site. Lighting bridge 1600 is used to maintain the desired portal size by preventing tissue creep, protecting soft tissue by establishing a portal boundary, and providing a lighting source within the portal. The method of engaging and advancing lighting bridge is the same as described for the portal bridges such as that shown in FIGS. 19 and 20. Additionally, however, groove 1603 is engaged with rod 1111A prior to being advanced into the portal, a button for lighting attached to bridge 1600 is depressed, and the bridge lights up. This light remains on while bridge 1600 is engaged to rod at various depths in the portal. When bridge is advanced to a location close to the surgical site, the light is directed toward the surgical site via tapered portion 1610B of the concave surface and the reflective surface of concave surfaces 1610A-C in general, to enhance the lighting at the surgical site. The surgeon may make any adjustments to color temperature or brightness at this time, as deemed appropriate. After surgery is complete and bridge is retrieved from the portal, either with retractor assembly or otherwise, it is removed from rod 1111 and the light deactivates. Lighting bridge 1700 is used according to a similar method, although when inserted with a rod separate from the rod assembly, it also involves a step of inserting fixation post 1721 into a surface within the patient upon full advancement and rotating a body of bridge to place it behind a rod of the rod assembly (e.g., rod 1111A adjacent to the rod with which it is engaged. In this manner, lighting bridge 1700 is secured in the surgical site. Lighting bridges as shown in FIGS. 52-57 may be used in a manner similar to that described for lighting bridge 1600.

In other embodiments, lights are incorporated into panel bridges and other structures for use in surgical procedures. Again, the bridges shown in FIGS. 26-27 are used in the same manner as that described for panel bridges such as that shown in FIGS. 19-20. Lights 1802, 1822, 1842 are actuated either manually by toggling a switch or automatically via means such as those described above. When a dual engagement bridge includes lighting, the lighting can be positioned on a panel of the bridge to direct it in a particular direction. The direction of lighting is maintained during use as the bridge is secured between two rods. Conversely, when lighting accompanies a bridge with a single clip or no clip, the bridge may be rotated within the portal to change to direction of the lighting, as desired. Lighting device 1902 shown in FIGS. 28 and 29 includes automatically toggled lighting 1902 based upon engagement with a rod, as shown in FIG. 29. Other forms of toggling the lighting are also contemplated. Through advancement of each modified bridge or other structure with lighting to a surgical site, a highly efficient form of lighting for surgery is obtained.

Rotating Panel Bridge

Figure 30:
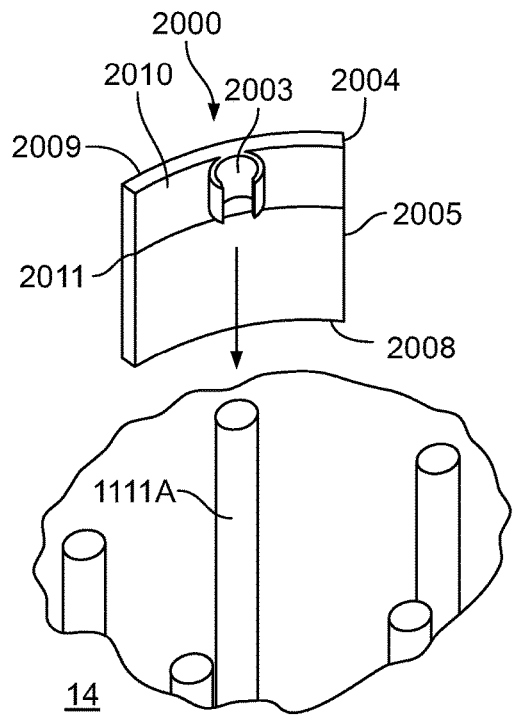
FIGS. 30-31 are perspective and side views, respectively, depicting the use of a rotating panel bridge according to one embodiment of the disclosure.

In another aspect, the present disclosure relates to rotating panel bridge structures. These bridges are designed to be minimally intrusive upon entry into a surgical portal but also include rotatable components to modify the portal to toe-in or toe-out, depending on the design. In one embodiment, rotating panel bridge 2000 includes an upper panel 2004, skirt panel 2005, hinge 2011, and a clip 2003. As shown in FIG. 30, rotating panel bridge 2000 is designed so that a concave surface 2010 extending over upper and skirt panels 2004, 2005, respectively, is portal facing, while convex surface 2009, also extending over the upper and skit panels, is tissue facing when the bridge is inside the body of a patient. As with other bridge embodiments, the tissue facing convex surface 2009 is a low friction surface. As depicted, clip 2003 is disposed on concave surface 2010 toward a middle area of upper panel 2004. Here, clip is only on upper panel, the reasons for which are described in greater detail below. Upper panel 2004 and skirt panel 2005 are joined by hinge 2011. As shown, rotating panel bridge 2000 is monolithic, and hinge 2011 is a thin, flexible hinge known as a live hinge. In a variant, and as described in several examples below, the components of the rotating panel bridge may be modular. Hinge 2011 is designed so that skirt panel 2005 is rotatable relative to upper panel 2004, as shown, for example, in FIGS. 35-37 and described in greater detail below. In other respects, rotating panel bridge 2000 is similar to panel bridges shown in FIGS. 18-23.

The rotating panel bridge may be varied in a multitude of ways. For example, the rotating panel bridge may be any number of shapes such as the examples described for the panel bridges shown in FIGS. 18-23. Similarly, the clip may be positioned at any location on the panel or multiple clips may be used. In some hinge designs, disposal of the clip only on the upper panel may be advantageous to reduce the force necessary to rotate the skirt panel. Where it is desired to have a "toe-in" rotating panel bridge, the clip may be placed on the tissue facing surface of the panel so that the attached rod does not interfere with the skirt panel as it rotates into the portal. In other examples, the rotating panel bridge may be a monolithic (as described above) or modular component structure. Where the bridge is monolithic, it may be formed by a single injection mold with a plastic polymer material. Examples of a modular design include separate components for the upper and skirt panels.

In other examples, the relative size of the upper and skirt panels may vary from that shown in FIG. 30. For example, the upper panel may be longer than the skirt panel, providing a smaller length of bridge for "toeing out." Additionally or alternatively, the skirt panel may rotate about an axis parallel to the portal rather than one transverse to it. For example, the skirt may rotate about an axis parallel to the rod. In this example, the axis of rotation may be along the skirt panel, for example, adjacent to the clip or adjacent to the edge of the skirt panel. The total number of panels included in the rotating panel bridge may also vary. For instance, the tissue retraction bridge may include two skirt panels and two hinges, one hinge between the upper panel and the first skirt panel, and a second hinge between the skirt panels. In this configuration, a varying toe-in" or "toe-out" is possible, as the portal may taper at a first angle over the length of the first skirt panel and then over another, typically larger angle over the length of the second skirt panel. This type of design may also be customized so that each of the two hinges have different properties, making each of the skirt panels rotate away from the panel immediately above a different amount. Such an effect of varying toe-in or toe-out may also be achieved through the use of different materials in each panel. For example, through use of materials having a first weight in one panel and a second weight in another panel. In other examples, the rotating panel bridge may include a fixation post that allows for full or partial engagement with a vertebral body or intervertebral disc to provide greater stability.

In still further examples, the function of the hinge may be achieved through use of a spring or a pin connection between panels that allows for rotational movement. When a coil spring is used, the rotating panel bridge is configured to be in a closed, i.e., compressed position when held and then released when the bridge is let go, causing the skirt panel to rotate relative to the upper panel. This is one example of an automatically rotating bridge. Others may be designed for manual rotation when advanced to a desired position in the surgical portal. For instance, a worm drive, rack and pinion mechanism, or a series of teeth may be used to control rotation of the skirt panel relative to the upper panel. In these manual constructions, the mechanism may include an exposed access point so that a tool may be used to cause the mechanism to operate and thereby rotate the skirt panel, e.g., by pushing it. For example, a screw driver or ratchet may be used to operate the mechanism. It is also envisioned that the bridge may be structured so that rotation of the panel is caused through a manual effort on the part of a surgeon without the use of any tools. Through the same principles described above, the hinge of the rotating bridge may also be structured to "toe-in" upon actuation as an alternative to or in addition to being structured to "toe-out."

Figure 31:
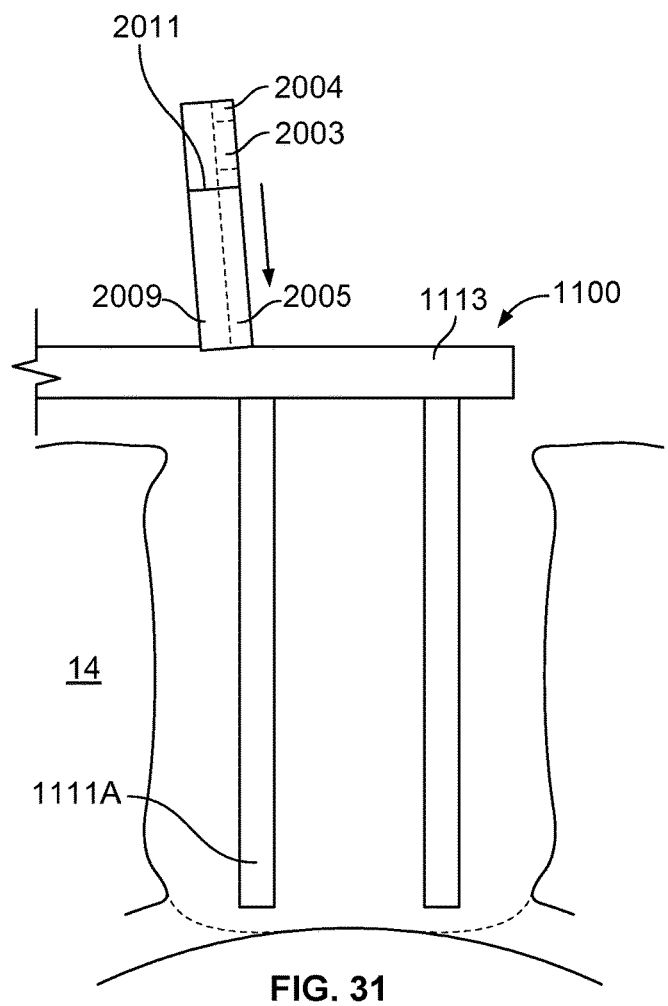
Figure 32:
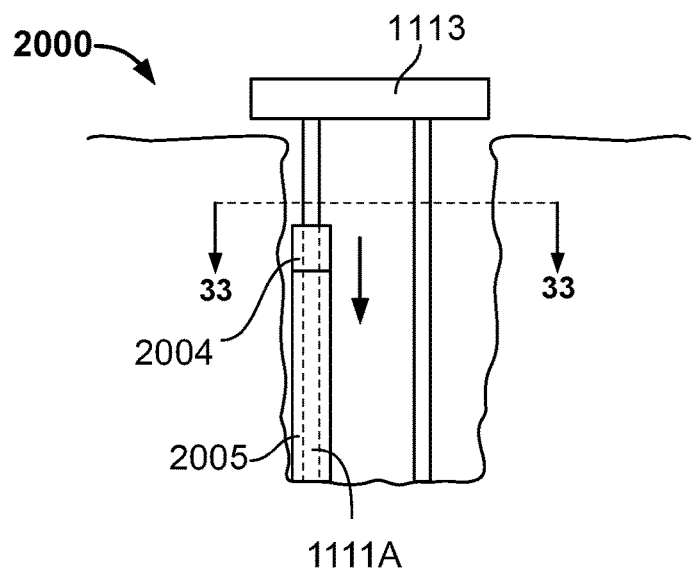
FIGS. 32-34 are side, top, and perspective views, respectively depicting the use of the rotating panel bridge of FIGS. 30-31.
Figure 33:
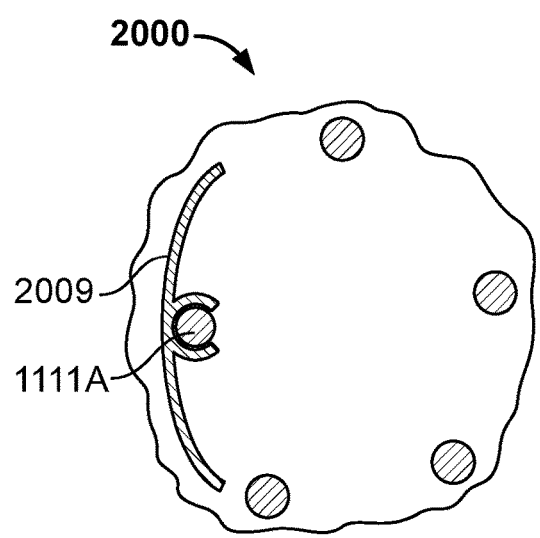
Figure 34:
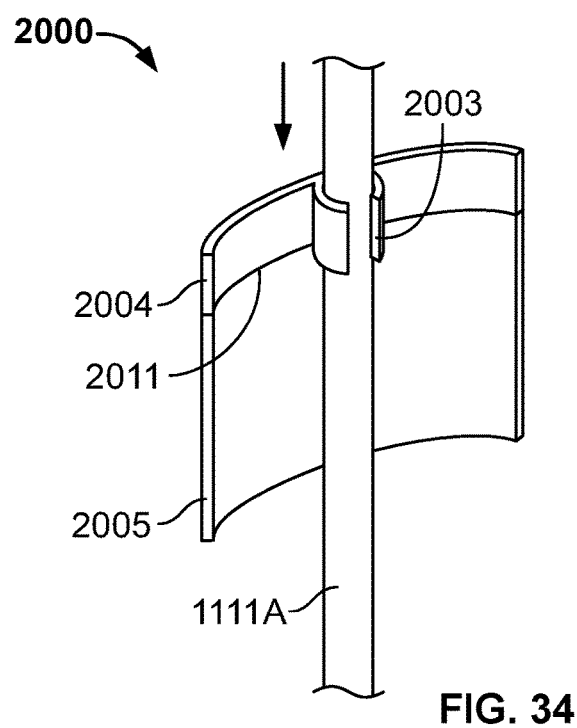

In another aspect, rotating panel bridge 2000 is employed in a method of surgical portal expansion. Initial portal creation including insertion and distraction of rods may be using techniques as described in other embodiments of the disclosure. In one embodiment, rotating panel bridge 2000 is retrieved in a pre-rotated position such that skirt panel 2005 is parallel to upper panel 2004, as shown in FIGS. 30-31. Rotating bridge panel is then advanced toward rod 1111A of retractor system 1100, as shown in FIG. 31, and clip 2003 is engaged with rod 1111A, similar to the methods of engagement for panel bridges as described above. Rotating panel bridge 2000 is then advanced into the surgical portal while engaged to rod 1111A until it reaches an intended destination within the portal, as best shown in FIG. 32. As shown in FIGS. 33 and 34, rotating bridge structure 2000 remains linear in length at this point and tissue displacement during advancement has been minimized by keeping panel on a periphery of the portal throughout.

Figure 35:
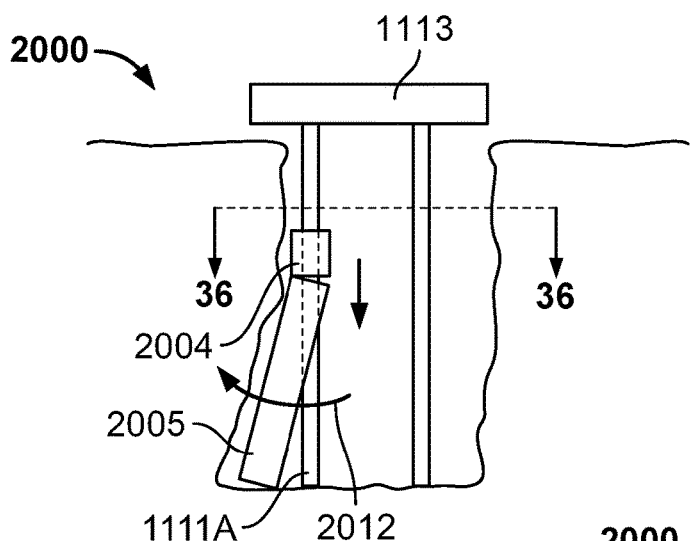
Figure 36:
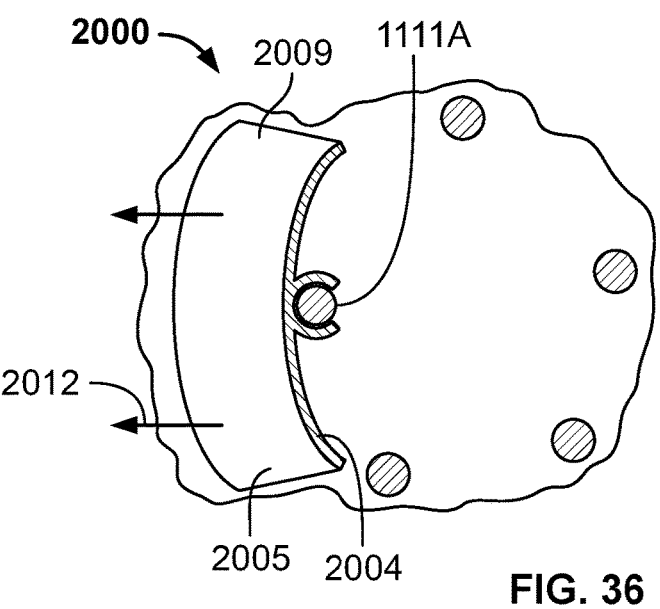
Figure 37:
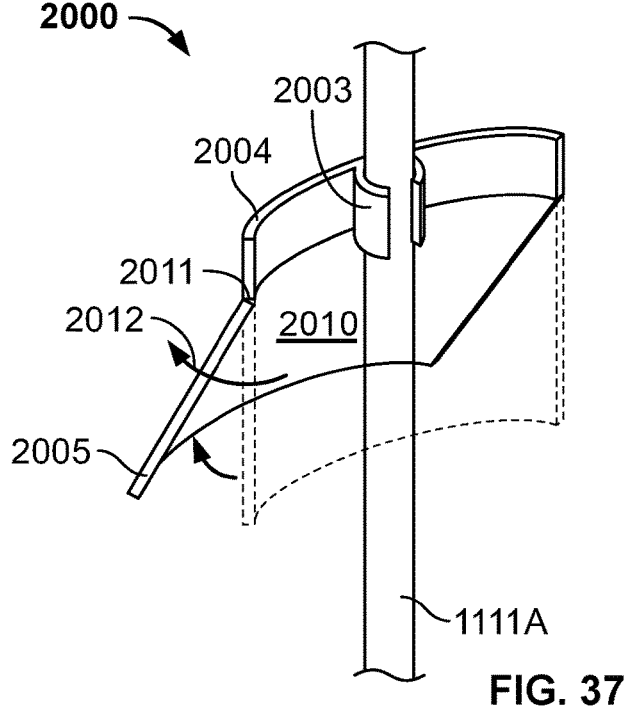

Once rotating panel bridge 2000 is at a desired depth, rotating panel bridge 2000 is actuated to create a "toe-out" in the portal. To do so, hinge 2011 is actuated so that skirt panel 2005 rotates 2012 about an axis through hinge 2011 toward the tissue facing direction. This rotation 2012 is best shown in FIGS. 35-37. As seen in particular in FIGS. 35 and 36, the rotation of skirt panel 2005 toward the tissue adjacent to the portal causes skirt panel 2005 to displace such tissue, creating the desired "toe-out" at the base of the portal, as seen in particular in FIG. 35. During this process, upper panel 2004 remains secured to rod 1111A via clip 2003, and thus provides stability to the hinge so that it doesn't disengage or otherwise shift from its position relative to the rod. The actuation of the hinge is accomplished through use of mechanisms as known to those of ordinary skill in the art. For example, the skirt panel rotates about hinge 2011 when a temporary securement on one side of the hinge is removed, leaving only the hinge, which has a tendency to cause the skirt panel to rotate in the tissue facing direction. The expanded portal size provides a surgeon greater freedom to work within the surgical portal while expanding the portal in a single desired direction. The tissue retraction bridge 2000 is removed in a similar manner to that described for other bridges as described herein.

Endoscope Bridge

Figure 40:
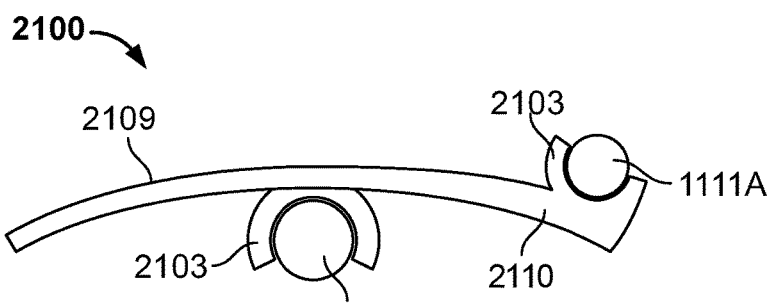

In yet another embodiment, endoscope bridge 2100 is used to provide hands-free endoscopic access to the working portal while still maintaining the size of the working portal and preventing tissue creep. Endoscope bridge 2100, as best shown in FIGS. 38 and 40, includes a panel with a concave surface 2110 and a convex surface 2109, and clips 2103, 2104A-B. Clip 2103 is disposed on the tissue facing, convex surface 2109 while clips 2104A-B are disposed on the portal facing, concave surface 2110. In the particular embodiment shown, endoscope bridge 2100 has a width extending from a first side 2101 to a second side 2102, and clip 2103 is positioned adjacent to second side 2102 while clips 2104A-B are parallel on the width and at an approximate midpoint of the panel. In other respects, bridge 2100 is similar to the panel bridges described above. Clips 2104A-B are offset somewhat from clip 2103, as best shown in FIG. 40, providing additional space for an endoscope probe 2105 to be engaged with clips 2104A-B without interference from rods 1111A-E. Clip 2103 is designed so that endoscope bridge 2100 is rotatable about rod 1111A. Clips 2104A-B are designed to engage endoscope probe 2105 to provide effective endoscopic access in the surgical portal. Endoscopes used with bridge 2100 are any contemplated for use in minimally invasive surgery, such as those described in the '228 Publication.

The Endoscope bridge may be varied in a number of ways including those described for the other bridge structures of this disclosure. For example, the clip designed for endoscope probe engagement may be modified to accommodate a variety of endoscopes. In other examples, endoscope bridge may incorporate lighting.

Figure 39:
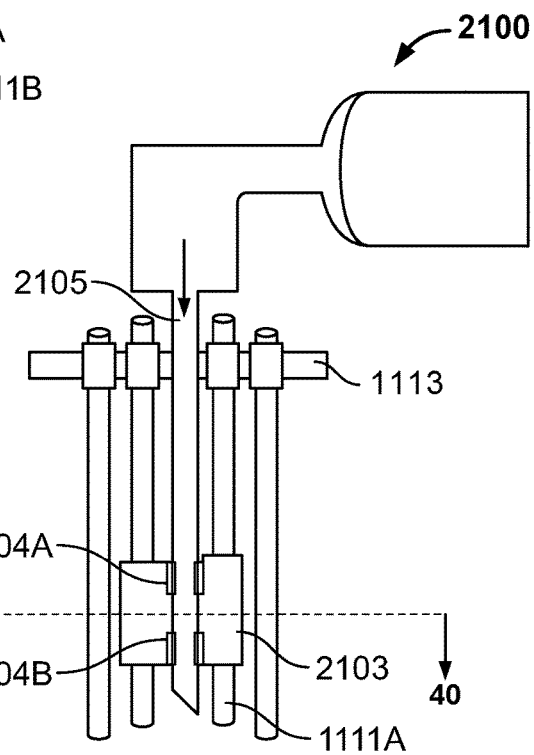
FIGS. 39-40 are side and top views, respectively, depicting the use of the endoscope bridge of FIG. 38.

In another aspect, the present disclosure relates to a method of using an endoscope bridge. In one embodiment, the surgical portal is prepared and an endoscope is retrieved. Clips 2104A-B of endoscope bridge 2100 are then engaged to an endoscope probe 2105 outside of the portal (not shown). Prior to insertion into the working portal, the surgeon selects the location within the working portal that will give the desired view. In the depicted embodiment, rod 1111A is chosen, as shown in FIGS. 39-40. Endoscope grooves 2104A-B are engaged with endoscope 2105 to ensure endoscope bridge 2100 remains stable as shown in FIG. 39. Endoscope bridge 2100 is then partially advanced into retractor system 1100 to engage clip 2103 with rod 1111A. Endoscope bridge 2100 is then advanced over rod 1111A with probe 2105 and the remainder of the endoscope attached into the working portal to a desired depth as shown in FIG. 39. In this position, the surgeon is able to view the desired portion of the working portal through the endoscope. The position of the endoscope probe 2105 can be rearranged by rotating bridge 2100 about rod 1111A to give the desired view. Another advantage of this approach is that it allows use of the endoscope hands free. After the surgery is complete, endoscope bridge 2100 can be withdrawn from the working portal by first removing the endoscope 2105 followed by bridge 2100 or vice versa, and then the retractor system 1100. In a variant, the endoscope bridge may be engaged with a rod of the retraction system and advanced into the portal prior to engaging an endoscope probe with the bridge.

Spring Bridge

Figure 41:
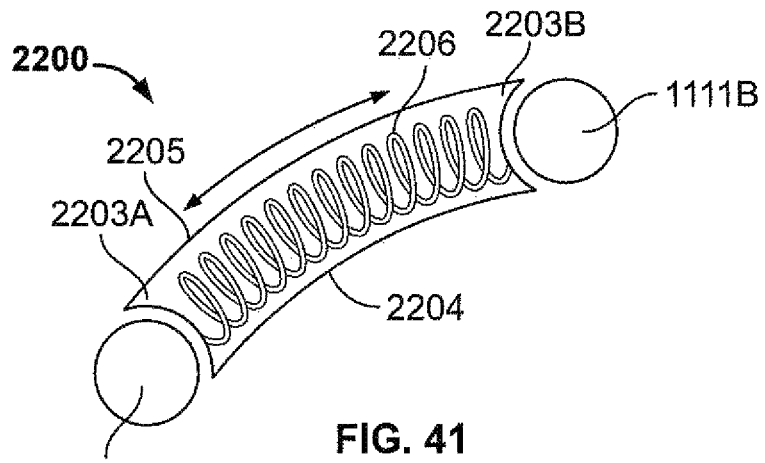
FIG. 41 is a top view of a spring bridge according to one embodiment of the disclosure.

In yet another embodiment, the present disclosure relates to spring bridge structures, which can provide greater stability in maintaining the size of the working portal while also providing greater stability between the rod structure within the portal. In one embodiment, spring bridge 2200 is as shown in FIG. 41 and includes an inner surface 2204, an outer surface 2205 and a spring 2206 spanning a width of bridge 2200 between a first side 2203A and a second side 2203B. Spring bridge 2200 is configured to compress upon loading at either or both sides 2203A, 2203B, and in this way is variable in shape to accommodate different spacings between rods of a retractor system. Moreover, once in place between rods, spring 2206 has a tendency to expand, creating pressure between sides 2203A-B and rods 1111A-B, thus enhancing the securement of bridge 2200 to the rods and mitigating the risk of tissue creep. Spring bridge 2200 is also designed to change in shape based on varying loads, such as load from tissue, and is therefore advantageous in that it is adaptable to different surgical conditions.

Figure 42:
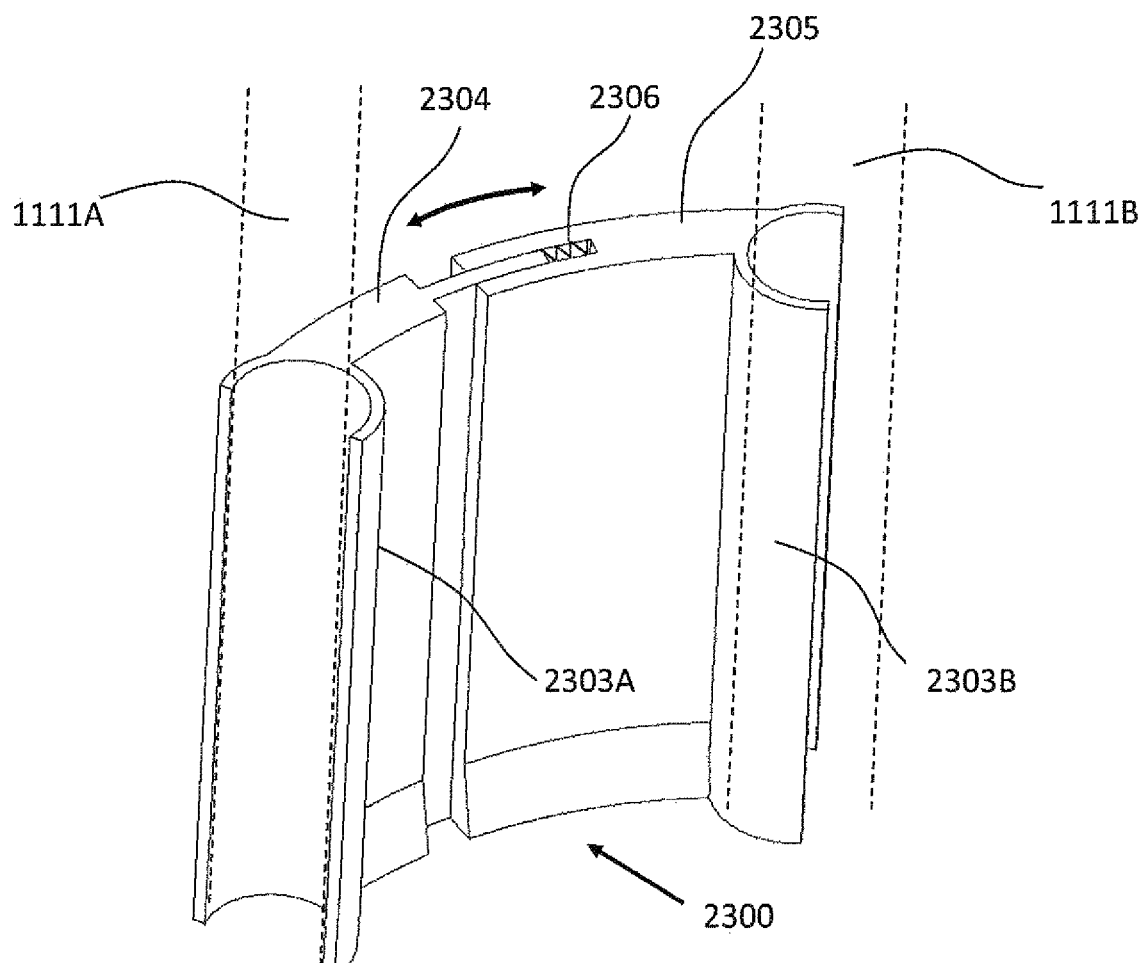
FIG. 42 is a perspective view of a spring bridge according to another embodiment of the disclosure.

In another embodiment, spring bridge appears as shown in FIG. 42 and includes a first portion 2304, a second portion 2305, clips 2303A-B, and a spring 2306. Clips 2393A-B are included at respective ends of spring bridge 2300 and are sized to engage with rods 1111A-B. Spring 2306 is disposed internally within bridge 2300 and compresses when load is applied to sides of the bridge, as in the aforementioned spring bridge. Here, however, first and second portions 2304, 2305 do not change in shape when spring is compressed. Rather, first portion 2304 slides over second portion 2305, decreasing an overall width of spring bridge 2300.

The spring bridge may be varied in a number of ways such as through incorporation into bridges described elsewhere in the description. For example, as variants of the panel bridge, the lighting bridge, and the rotating panel bridge. Thus, for instance, a spring feature providing an adjustable width can be incorporated into a lighting bridge such as that described above. Further, the spring bridge may include a locking mechanism to allow the surgeon to fix the position of the spring bridge once the spring is fully compressed or expanded. After one clip of the bridge has engaged a rod, the surgeon may activate a switch to release the spring bridge, thus allowing the panel adjacent the other clip to be released and engage a second rod. In another example, the spring may be substituted with a slot and pin or other mechanism allowing for the movement between two connected panels to alter a width of the bridge.

Figure 43:
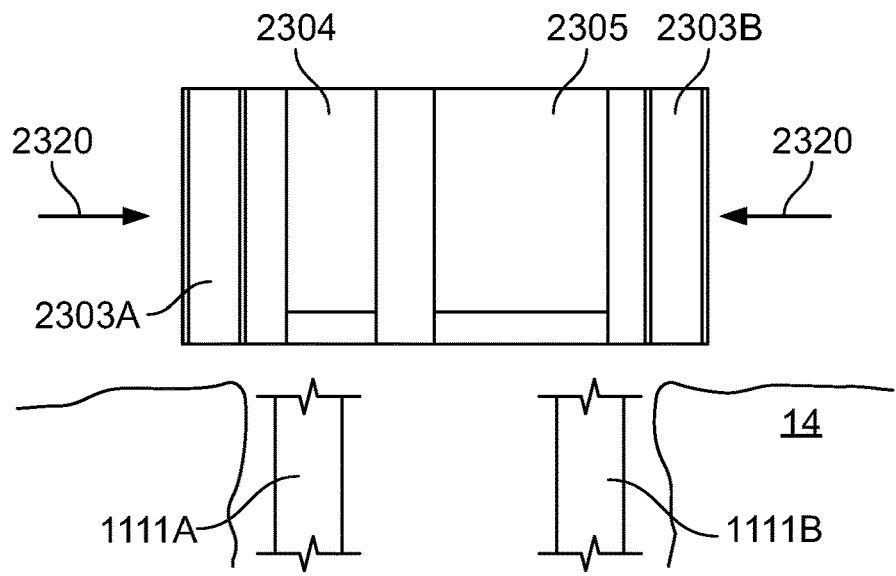
FIGS. 43-45 are a side views depicting the use of the spring bridge of FIG. 42.
Figure 44:
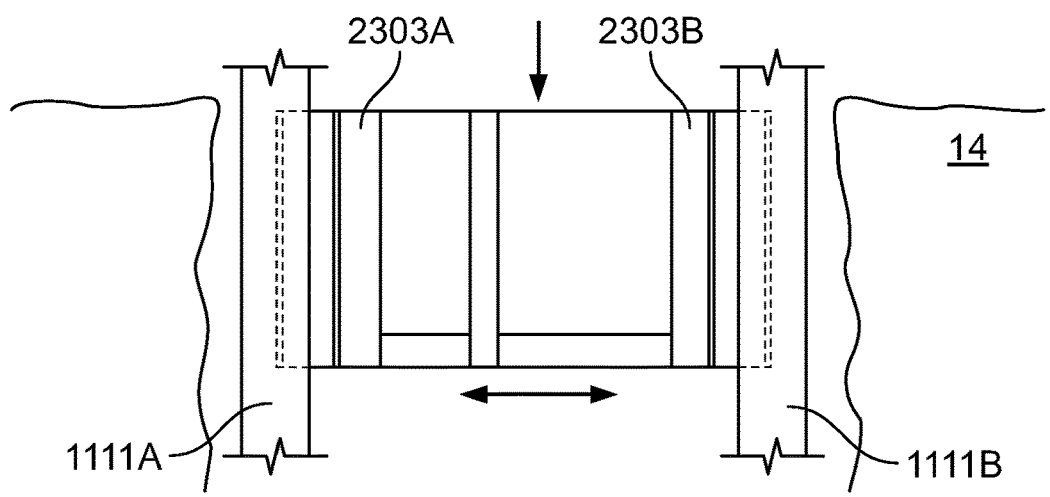
Figure 45:
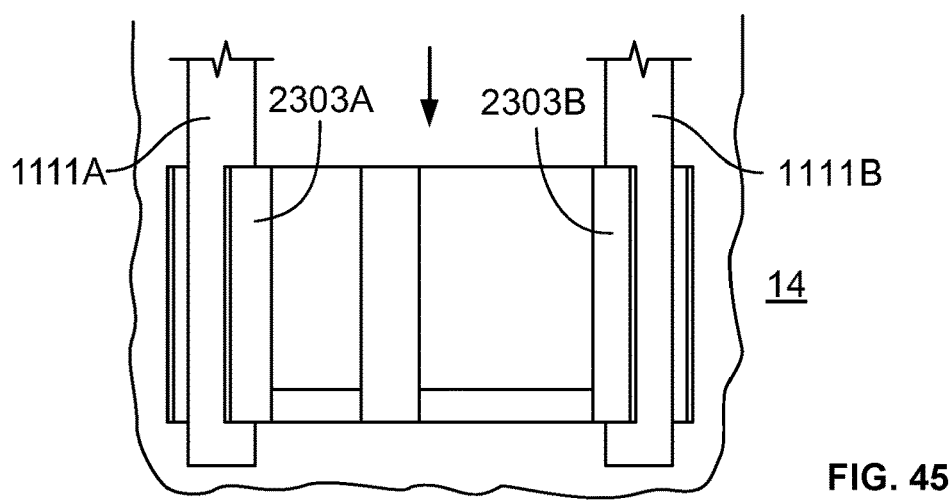

In another aspect, the present disclosure relates to methods of using spring bridges. In one embodiment, spring bridge 2300 is compressed prior to advancing into the surgical portal by applying pressure on each side of the bridge 2320 at clips 2303A-B as shown in FIG. 43. Once the spring bridge 2300 is compressed to a width capable of fitting between rods 1111A-B, spring bridge 2300 is advanced into the surgical portal as shown in FIG. 44. Once advanced sufficiently to be between target rods 1111A-B, the compression on spring bridge 2300 is slowly released by decreasing the pressure applied at clips 2303A-B at an incremental pace to allow for the spring bridge 2300 to expand in a controlled manner. Once clips 2303A-B expand to contact the rods, clip 2303A will engage with rod 1111A while clip 2303B will engage with rod 1111B. If alignment of the bridge is off, the bridge may be rotated about an end engaged with one of the rods to align the other end with the second rod. Upon each groove 2303A-B engaging respective rods 1111A-B, spring bridge 2200 is advanced further into the portal to a desired depth. The constant tension from spring 2306 provides a more secure working boundary while further stabilizing the rod structure within the retractor system.

Shims

In another aspect, the present disclosure relates to shims, sometimes referred to as spikes, and bridges, both sized and otherwise configured for attachment to and sliding on rods of a retractor, such as rod 120. Shims and bridges as described herein serve many functions, including, for example, holding back tissue in a retracted surgical portal and providing lighting in the surgical portal. Shims serve an additional purpose of anchoring the retractor to a bone of a patient via a spiked tip of the shim.

In one embodiment, shim is as shown in FIGS. 58-60. Shim 600 extends from a top end 604 to a pointed tip 602. The shim depicted includes a central portion 601 with a "C" shaped cross section, designed for securement to a complementary cylindrical rod. A cylindrical surface 605 defines one side of a central portion 601 of shim 600 running the course of its length. Central portion 601 defines a body clip, in that an interior surface of central portion 601 is structured to engage with a retractor rod. At a tail end of central portion is a flat end surface 604, while at a leading end is pointed tip 602. Pointed tip 602 is shaped so that it forms an anchorage when applied to a surface within the body, such as a vertebrae or an intervertebral disc. Central portion 601 further includes a cut out portion with a bending clip 606 extending from central portion 601 into the cut out, as shown in FIG. 59. At a free end of bending clip 606 is an inward facing protrusion in the form of a finger 608. Bending clip 606 is structured to extend from central portion 601 so that it is flexible at its free end corresponding to finger 608. Put another way, the bending clip is elastically deformable. This allows bending clip 606 to be pulled away from cylindrical surface 605 and, when released, bending clip 606 returns into its natural position. Clip 606 is advantageous in that it constitutes a locking feature that can hold onto a notch or groove of a rod, for example, such as notch 124A shown in FIG. 3. This prevents shim 600 from detaching from rod, which is particularly important when the rod is inside a patient during a surgery.

Extending from opposite sides of central portion 601 are wings 610A-B. Wings 610A-B are contoured to minimize size while also defining a curved outer perimeter. In this manner, when shim 600 is in position over a rod among a plurality of rods that are holding open a surgical portal in a patient, convex surfaces 626A-B of shim 600 have structural strength sufficient to hold back tissue while preserving space within the surgical portal. As shown in FIGS. 59 and 60, each wing also includes a concave surface 620A-B. Convex surfaces are generally smooth to promote ease of insertion of shims when slid over a rod and abutting a surface, such as human tissue. This surface also has the advantage of retracting and maintaining protection of tissue when positioned adjacent thereto. Additionally, sides of convex surfaces 626A-B are chamfered to ease passage of shim over a surface, such as during insertion over a rod and into a patient. On convex surface 626A-B side of shim 600 are cutouts defining grooves 614, 616, respectively, in the shim surface, as best shown in FIG. 60. These grooves 614, 616 extend over at least a portion of shim 600 length and provide space for disposal of LEDs, e.g., 640A-B, wiring, and potentially batteries therein. On the concave side of wings 620A-B, and extending over cylindrical surface 605, are conical cuts 622A, B. Such cuts are shaped to direct light from a location near the top of the cut downward toward pointed tip 602 and inward.

Central portion 601 provides for engagement of shim 600 to a rod while at the same time allowing shim to be slid longitudinally over rod. Shim is configured so that it may be locked relative to a rod using finger 608 of bending clip 606, described in greater detail in the method below.

Shim 600 is constructed of clear optic materials such as polymers so that light from an LED may pass through the shim. Other non-limiting examples of materials include those having radiolucency, such as aluminum or titanium. Others include stiff polymers such as polycarbonate or PEEK in order to maintain radiolucency and to maintain a desired stiffness. Carbon fiber may also be used. In other examples, materials may be used in combination. For example, an upper part of shim may be a transparent material while the tip may be carbon fiber to provide stability and to provide a radiopaque quality. Indeed, radiolucency may be tailored such that only certain areas of the shim are radiopaque, such as the spiked portion of the shim. In still further examples, tantalum markers may be included in the shim to monitor its location during surgery.

Shim 600 is sized and shaped to accommodate disposal of LEDs and other structural components thereon so that it may function as a lighting device. As shown in FIG. 60, LEDs 640A, 640B are disposed in respective grooves 614, 616 in the wings. LEDs may be secured to shim using means known to those of ordinary skill, such as through the use of adhesives. Wiring (not shown) leading to the LEDs may also be disposed within grooves and extend out of and away from top surface 604 of shim 600 to a power source, such as a battery. In one variant of shim 600, a battery may be disposed within grooves 614, 616 where a battery is available that fits therein. This makes the shim an entirely self-contained lighting device. In another variant, a shim may include a body clip and a single wing on one side, such as wing 610A. In yet another variant, a shim may be built into a distal end of the rod so that it is monolithic with the rod but also rotatable between a closed and open position to reveal a spiked tip for engagement with a vertebral disc or other internal surface of a patient.

In another embodiment, a bridge configured for attachment to a rod is as shown in FIGS. 61 and 62. Generally, reference numerals of bridge 700 refer to like elements of shim 600. Unlike shim 600, bridge 700 includes flat end surfaces 702, 704 on both ends of its length. Additionally, a middle portion along its length is recessed as shown in FIG. 62, and is defined by surfaces 724A-B. Through this region of bridge 700, cylindrical surface 705 is absent, creating a central void 774 in bridge 700. This divides central portion 701 into first and second parts 771, 772 at respective ends of the bridge. As shown in FIG. 62, each part of the central portion is interconnected through wings 710A, 710B. However, bending clip 706 does extend from a lower portion of cylindrical surface 705 similar to shim 600, and includes finger 708 engageable to a notch in a rod, such as notches 124A of rod 120. Recessed regions 724A-B are dimensioned so that two LEDs 740A-B attached at an upper end of such recessed regions, when activated, direct light in a downward and inward direction toward a free end of rod. Materials of the bridge may be any already described for shim above.

The shim or bridge can be varied in many ways. For example, the attached lighting may be modified to accommodate a particular working volume. For instance, where the working area measures 14 mm by 22 mm in dimensions on the disc space to be operated on and a depth to be accessed is 40 mm from a surface of a body of a patient, the shim or bridge size and LED quantity and layout can be arranged to ensure the working volume has sufficient light. For example, LEDs may be included on surfaces 620A-B on shim 600. In other examples, the shim or bridge may incorporate any number of features from the various embodiments of this disclosure. In some examples, the central portion, or body clip of the shim or bridge may have a square cross-section, a rectangular cross-section, an oval cross-section, or any other cross section necessary to clip onto an applicable rod of a retractor. In this manner, body clip may be square shaped, and so on.

In another example, the shim may include a lengthwise protrusion sized to complement a dovetail groove running along a length of a rod onto which shim is designed for securement. This form of securement is advantageous where it is desirable to limit rotation of the shim or bridge while attached to the rod, as rotation of the shim relative to the rod is minimized. In some examples featuring a lengthwise protrusion, the body clip of shim is an internal dovetail groove, in contrast to the external C-clip of the depicted shim and bridge embodiments. In other examples, the bending clip may be structured for one of passive or active engagement with a rod. Similarly, bending clip may have a shape other than that shown in FIGS. 58-59 and 61-62.

In other examples, LEDs may be attached at any location as desired on a surface of shim or bridge. Although the embodiments depicted in FIGS. 58-62 each include two LEDs, it is contemplated that the shim or bridge may have a greater number of LEDs in total. Indeed, one way a lit shim or bridge may have a higher maximum brightness is through the inclusion of a greater number of LEDs. In further examples, the shim or bridge may include neuromonitoring elements built into its structure. In these cases, shims or bridges made of polymers complement neuromonitoring in that such materials are a good insulator for the neuromonitoring element. The neuromonitoring element may be gold coated copper, aluminum or another electrical conductor.

In still further examples, the shim or bridge may include gripping features designed to engage with a removal instrument. Such instrument may be lowered to shim while shim is attached to a rod, engage with the shim, and then bring the shim out of the working portal. In other variants, a cable may be connected to the shim so that while the shim is in the portal, the cable remains accessible outside of the surgical field. Thus, in the event the shim becomes displaced, the shim is retrievable with the cable.

Figure 63:
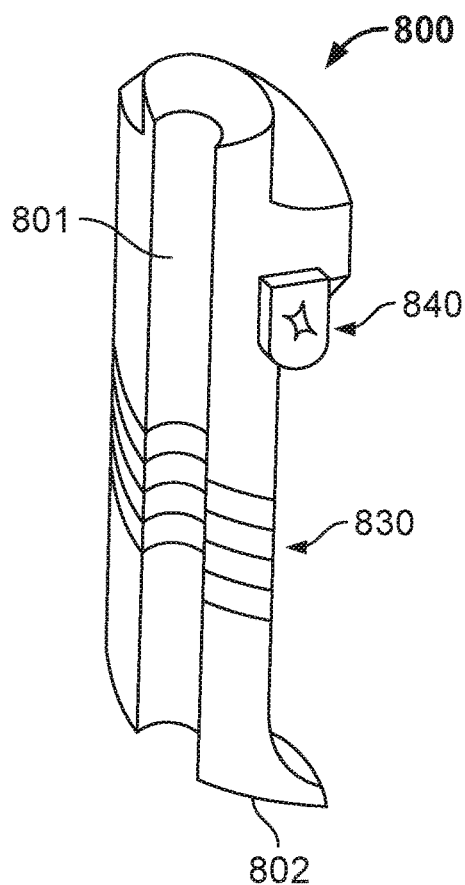
FIG. 63 is a perspective view of a bridge according to another embodiment of the disclosure.

In other examples, the shim or bridge may include a receiving coil or other device so that power may be transmitted to the shim or bridge wirelessly and LEDs of the shim or bridge may operate without a battery or wires secured thereto. The wireless technology contemplated for these examples is the same as described above for the rods. One example of a bridge receiving power wirelessly is shown in FIG. 63, where a bridge 800 includes LED 840 attached thereto in addition to a receiving power coil 830 around body clip 801. Bridge 800 wirelessly receives power through power coil 830 and coil in turn, through its connection to LED 840, sends any received power to LED 840. The principles described for bridge 800 can also be applied to other supporting structures configured to be positioned within a surgical portal created through retraction of the rods attached to a retractor. For example, a ring 900 disposable in between the rods of a retractor and engageable with rods through grooves 901, as shown in FIG. 22, may include a receiving power coil 930 to wirelessly power a plurality of LEDs 940 attached to ring. In this manner, with ring 900 disposed between rods at a desired depth within a surgical portal, a variety of lighting configurations may be employed by selectively activating LEDs on the ring.

Kits

Another aspect of the present disclosure relates to a kit including one or more items, such as a set of rods with complementary light pipes. In one embodiment, a kit includes one rod and a light pipe sized to fit in the rod or, similarly, one rod and a light bar sized to fit in the rod. In another embodiment, a kit includes a number of rods matching a number of arms on a retractor, where each rod is structured to accommodate a light pipe therein, and the kit further includes a matching light pipe for each rod, the light pipes being disposable in the rods. In a variant, a kit includes light bars in place of light pipes where the rods are structured with a slot for disposal of the light bars therein. In another variant, a kit includes only one of rods, light pipes, or light bars.

In another embodiment, a kit includes one or more shims, bridges or rings. In a variant, a kit includes any combination of shims, bridges or rings. In variants, such a kit may further include one or more wands (not shown), either rigid or flexible, designed to clip onto a rod, a shim, a bridge, or the retractor frame. The wand contemplated provides another means for directing light in a customized manner within the surgical portal as it may be held and swept around an interior of the portal. In yet another embodiment, any combination of rods, such as those described for the above kits, may be included in a kit with any combination of shims, bridges, rings or wands.

In yet another embodiment, a kit includes any combination of the above elements along with a battery enclosed in a housing structure such as the housing of system 10, 30 or 40, shown in FIG. 2A, 14 or 15, respectively. Similarly, a kit may be a light-box structure such as the one included in system 20, shown in FIG. 13. In any one of these kits, sets of wires and/or fiber optic cables may be included, as applicable. In variants, such kits may include more than one battery, and may comprise different types of batteries in one kit. For example, some external units may include a battery and PCB, while others may include a battery, PCB and LED(s). In other embodiments, the kits including one or more batteries may include any combination of rods, shims, bridges or rings, in addition to one or more wands. In other embodiments, a retractor and frame structure may be included in any of the above contemplated kits.

In any one of the above embodiments, the kit or individual items and combinations thereof may be disposed within a packaging or a plurality of packages. For example, all of the items of the kit may be disposed within a single packaging. In another example, all of the rod and lighting pipe/bar combinations may be in one packaging while all of the shims, bridges and/or rings in another. In further examples, each individual light pipe, light bar or rod is separately sterilized and packaged. Sterilization may be through techniques including autoclave steam, gamma irradiation, or chemical sterilization, among other known approaches. It is contemplated that the elements of a given kit may be sorted into any subgroups desired, where each subgroup may be packaged separately. Of course, each item of a kit may also be individually packaged. For example, each rod and light pipe in a kit may be packaged separately. Through packaging each item in the kit separately or in different combinations, sterility of each item within the kit in the preparation for surgery is promoted.

In other embodiments, the bridges described in the disclosure may be incorporated into customizable kits or others that may be produced at volume. Some kits may include single use bridges, such as those with lighting activated for a single use. Bridges in the kits may include panel bridges, lighting bridges, and others as described herein, and each may include those of varying widths and lengths, varying rod connection options and varying degrees of material rigidity, among other design characteristics. Rigidity is a function of thickness and material properties, so those are potential variables for the bridges in the kit as well. In addition to bridges, the kits may also include instrumentation used to place implants or other structures for the surgeries contemplated herein.

Other Considerations

In any of the above aspects and embodiments of the present disclosure, the advantages of employing bridge structures to improve surgical portal maintenance may be enhanced through use of retractors with blade or rod structures that include at least some capacity for flexure when subject to loading. In this manner, the blades or rods will withstand a certain amount of deflection under loading. An example of rods having such properties is described in the '228 Publication. The bridges of the various embodiments of the present disclosure may also be used or otherwise be modified for use with the Stryker® ARIA and Stryker® Phantom Retractor systems. In any of the above embodiments of the bridge, the bridge can be engaged with a rod separate from the retractor and be advanced separately from the retractor system into the body of the patient. Thus, where a surgical portal is already created with a retractor system, a separate bridge may be advanced into that portal for purposes such as endoscopy, lighting, and any other function deemed pertinent under the circumstances.

Variations

Each bridge or shim described above may vary in shape as a matter of design choice. Bridges or shims may have linear, curved, irregular, jagged or other shapes as a matter of design choice and surgical application. Additionally, a length of each bridge or shim may vary to suit design needs for each of the contemplated embodiments. Materials as described for certain embodiments may also be used in others as a matter of design choice.

Lateral Access Alignment Guide and Rigid Arm

The structures, systems and methods as described herein may be used in surgical settings where a retractor holding rods intended for expansion is supported by the rigid arm or frame of the '780 Application. Additionally, alignment to determine an insertion location for inserting the same rods into the body may be performed using an alignment guide described in the '780 Application.

Independent Rod Suspension

The structures, systems and methods as described herein may be used in surgical portals bounded by rods of a retractor where at least one rod varies in shape in response to changes in loading on the rod. Details of such rods forming part of a retractor assembly are described in the '841 Application.

Expanders for Rod Retraction

The structures, systems and methods as described herein may be part of a surgical procedure where at least some of the steps involved in distracting rods of a retractor involve the insertion of expanders such as those described in the '847 Application in between the rods, thereby increasing a surgical portal size in between such rods.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A tissue retaining device sized for attachment to a rod of a retractor comprising:
  a body comprising:
    a central portion having a first outer surface and a first inner surface opposite the first outer surface, a groove on the first outer surface complementary to a portion of the rod such that the central portion is configured to clip onto the rod, and an arm with a protrusion at a free end of the arm configured to engage with a complementary recess in the rod; and
    a wing adjacent to the central portion, the wing having a second outer surface and a second inner surface opposite the second outer surface,
    wherein the first inner surface of the central portion protrudes relative to the second inner surface of the wing and an entirety of the arm is on one side of an axis through a width dimension of the wing, the width dimension being perpendicular to a longitudinal dimension of the rod when the central portion is clipped onto the rod.

2. The device of claim 1, wherein the first inner surface of the central portion is convex and terminates in a pointed tip.

3. The device of claim 1, wherein the arm is a bending clip, the bending clip being elastically deformable.

4. The device of claim 1, further comprising at least one of a power cell or a light emitting diode disposed in a pocket recessed in the second outer surface of the wing.

5. The device of claim 1, wherein the central portion is divided into first and second parts separated by a central void, the first and second parts being interconnected through the wing.

6. The device of claim 5, wherein the arm is entirely in between the first and second parts.

7. A surgical portal system for use in a body of a patient comprising:
  two or more rods adapted for use with a retractor assembly; and
  a panel and a first clip attached to the panel, the panel having an outer surface and an inner surface,
  wherein the inner surface of the panel is concave and has a first radius when measured in a plane perpendicular to a longitudinal direction of the two or more rods, and
  wherein the first clip has a rod engaging surface that is concave and has a second radius smaller than the first radius when measured in the plane, the first clip sized such that a first rod of the two or more rods is releasably received therein,
  wherein when the first clip is engaged to the first rod, the two or more rods are disposed on a single side of the panel and the first clip is movable along a length of the first rod, and
  wherein the panel is of a thickness and is made of a material with a capacity to withstand loads from tissue bearing on an outer surface of the panel, the outer surface being opposite the inner surface.

8. The system of claim 7, wherein the first clip is a C-shaped channel.

9. The system of claim 7, further comprising a second clip attached to the panel, the second clip sized such that a second rod of the two or more rods is releasably received therein.

10. The system of claim 9, wherein one of the first clip and the second clip is attached on the inner surface of the panel and the other of the first clip and the second clip is attached on the outer surface of the panel.

11. The system of claim 9, wherein the panel has a width orthogonal to a direction of the first rod received in the first clip, the width extending from a first lateral end to a second lateral end, the first clip being attached to the panel at the first lateral end.

12. The system of claim 9, wherein the first and second clips are disposed at a common location on a length of the panel so that when the first rod is engaged to the first clip and extends over the length of the panel, the first rod does not contact the second clip.

13. The system of claim 7, wherein the panel further comprises a skirt panel attached at a leading end of the panel, the skirt panel being pivotable relative to the panel about an axis along a joint between the panel and the skirt panel.

14. The system of claim 7, further comprising a spring element configured so that a width of the panel changes in conjunction with expansion or compression of the spring element.

15. A tissue retraction panel configured for use with a rod associated with a retractor assembly, the tissue retraction panel comprising:
  a body with a first surface and a second surface opposite the first surface, the body having a cavity therein, wherein the first and second surfaces extend from a first end of the body to a second end of the body opposite the first end; and
  a groove recessed relative to the first surface of the body, the groove sized to receive the rod so that the tissue retraction panel is slidable over the rod when the tissue retraction panel is engaged to the rod, the groove extending from the first end of the body to the second end of the body;

a light emitting device disposed on the second surface of the body; and a power cell disposed in the cavity of the body, wherein the light emitting device is configured to emit light when supplied with power from the power cell.

16. The tissue retraction panel of claim 15, further comprising a button on the groove of the body of the panel, the button configured to operate as a switch connected to the light emitting device so that when the button is depressed, the light emitting device emits light and when the button is not depressed, the light emitting device does not emit light.

17. The tissue retraction panel of claim 15, further comprising an electrical barrier on the body of the panel, the electrical barrier configured to cause the light emitting device to emit light upon its removal.

18. The tissue retraction panel of claim 15, wherein a portion of the body including the second surface is made of a transparent material.

19. The tissue retraction panel of claim 15, further comprising wiring to connect the power cell with the light emitting device, the wiring being entirely disposed within the body.

20. The tissue retraction panel of claim 15, further comprising a fixation post attached to the body, the fixation post configured for engagement with a soft tissue surface.

* * * * *